(12) United States Patent
Josel et al.

(10) Patent No.: US 10,718,769 B2
(45) Date of Patent: *Jul. 21, 2020

(54) COMPOUNDS COMPRISING ONE OR MORE HYDROPHOBIC DOMAINS AND A HYDROPHILIC DOMAIN COMPRISING PEG MOIETIES, USEFUL FOR BINDING CELLS

(71) Applicant: Roche Diagnostics Operations, Inc., Indianapolis, IN (US)

(72) Inventors: Hans-Peter Josel, Weilheim (DE); Dieter Heindl, Munich (DE); Thomas Froehlich, Penzberg (DE); Stefanie Froehner, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/186,578

(22) Filed: Jun. 20, 2016

(65) Prior Publication Data

US 2017/0146533 A1 May 25, 2017

Related U.S. Application Data

(63) Continuation of application No. PCT/EP2014/078758, filed on Dec. 19, 2014.

(30) Foreign Application Priority Data

Dec. 20, 2013 (EP) .................................... 13006038

(51) Int. Cl.
*C07J 17/00* (2006.01)
*C07J 9/00* (2006.01)
(Continued)

(52) U.S. Cl.
CPC ..... *G01N 33/56972* (2013.01); *C07D 311/04* (2013.01); *C07D 311/82* (2013.01);
(Continued)

(58) Field of Classification Search
CPC ... G01N 33/558; G01N 33/94; G01N 2800/52
See application file for complete search history.

(56) References Cited

U.S. PATENT DOCUMENTS

2005/0208644 A1 9/2005 Takiguchi et al.
2017/0363624 A1* 12/2017 Josel ................ G01N 33/56972
2018/0141935 A1 5/2018 Josel et al.

FOREIGN PATENT DOCUMENTS

EP 1489167 A1 12/2004
JP 2005-312377 A 11/2005
(Continued)

OTHER PUBLICATIONS

Baha, Takeshi et al., Induction of cell membrane protrusions by biotinylated PEG-cholesterol, Japan Society for Cell Biology, 2001, p. 59, vol. 54.
(Continued)

*Primary Examiner* — Shafiqul Haq
(74) *Attorney, Agent, or Firm* — Roche Diagnostics Operations, Inc.

(57) ABSTRACT

The present invention relates to novel compounds comprising one or more hydrophobic domains and a hydrophilic domain comprising PEG moieties, useful for binding cells, as well as uses and compositions related thereto. The compounds are useful for immobilizing and/or stabilizing cells.

8 Claims, 41 Drawing Sheets

(51) Int. Cl.
G01N 33/58 (2006.01)
C07D 311/04 (2006.01)
C07D 311/82 (2006.01)
G01N 33/569 (2006.01)
C07J 51/00 (2006.01)
C12N 11/06 (2006.01)
G01N 33/50 (2006.01)
G01N 33/543 (2006.01)
C07D 495/04 (2006.01)

(52) U.S. Cl.
CPC .............. C07D 495/04 (2013.01); C07J 9/00 (2013.01); C07J 17/00 (2013.01); C07J 51/00 (2013.01); C12N 11/06 (2013.01); G01N 33/5005 (2013.01); G01N 33/54353 (2013.01); G01N 33/56966 (2013.01); G01N 33/582 (2013.01)

(56) References Cited

FOREIGN PATENT DOCUMENTS

| JP | 2008-81486 A | 4/2008 | |
|---|---|---|---|
| JP | 2011-185874 A | 9/2011 | |
| WO | 1996/010399 A1 | 4/1996 | |
| WO | 2000/051572 A1 | 9/2000 | |
| WO | 2001/007011 A1 | 2/2001 | |
| WO | 2002/076428 A1 | 10/2002 | |
| WO | 2003/074691 A1 | 9/2003 | |
| WO | 2008/073458 A2 | 6/2008 | |
| WO | 2008/147438 A2 | 12/2008 | |
| WO | 2009/103753 A1 | 8/2009 | |
| WO | 2010/047793 A2 | 4/2010 | |
| WO | WO-2010141069 A2 * | 12/2010 | .......... C08G 65/329 |
| WO | 2011/011055 A1 | 1/2011 | |
| WO | 2012/065751 A1 | 5/2012 | |
| WO | 2012/094642 A2 | 7/2012 | |
| WO | 2013/148579 A1 | 10/2013 | |
| WO | 2013/188763 A1 | 12/2013 | |

OTHER PUBLICATIONS

Thomas, Colin R. and Zhang, Zhibing, The Effect of Hydrodynamics on Biological Materials, Advances in Bioprocess Engineering II, 1998, 137-170.
Wikipedia, Unified atomic mass unit (Dalton), downloaded from https://en.wikipedia.org/wiki/Unified_atomic_mass_unit, Feb. 10, 2017, 5 pages.
International Search Report dated Feb. 5, 2015, in Application No. PCT/EP2014/078758, 4 pages.
Jensen, Tor W. et al., Lipopeptides Incorporated into Supported Phospholipid Monolayers Have High Specific Activity at Low Incorporation Levels, Journal of the American Chemical Society, 2004, pp. 15223-15230, vol. 126.
Kato, Koichi et al., Immobilized culture of nonadherent cells on an oleyl poly(ethylene glycol) ether-modified surface, BioTechniques, 2003, pp. 1014-1021, vol. 35, No. 5.
Kato, Koichi et al., Rapid Protein Anchoring into the Membranes of Mammalian Cells Using Oleyl Chain and Poly (ethylene glycol) Derivatives, Biotechnology Progress, 2004, pp. 897-904, vol. 20.
Kuhn, Phillip et al., A facile protocol for the immobilisation of vesicles, virus particles, bacteria, and yeast cells, Integrative Biology, 2012, pp. 1550-1555, vol. 4, No. 12.
Michaels, James D. et al., Protection Mechanisms of Freely Suspended Animal Cells (CRL 8018) from Fluid-Mechanical Injury. Viscometric and Bioreactor Studies Using Serum, Pluronic F68 and Polyethylene Glycol, Biotechnology and Bioengineering, 1991, pp. 169-180, vol. 38.
Miura, Suguru et al., Encapsulation of islets with ultra-thin polyion complex membrane through poly(elthylene glycol)-phospholipids anchored to cell membrane, Biomaterials, 2006, pp. 5828-5835, vol. 27.
Palomares, Laura A. et al., Evidence of Pluronic F-68 direct interaction with insect cells: impact on shear protection, recombinant protein, and baculovirus production, Enzyme and Microbial Technology, 2000, pp. 324-331, vol. 26.
Ramirez, Octavio T. and Mutharasan, R., The Role of the Plasma Membrane Fluidity on the Shear Sensitivity of Hybridomas Grown under Hydrodynamic Stress, Biotechnology and Bioengineering, 1990, pp. 911-920, vol. 36.
Sowana, D. D. et al., Studies of the shear protective effects of Pluronic F-68 on wild carrot cell cultures, Biochemical Engineering Journal, 2002, pp. 165-173, vol. 12.
Tomeczkowski, J. et al., Effect of cholesterol addition on growth kinetics and shear stress sensitivity of adherent mammalian cells, Enzyme & Microbial Technology, 1993, pp. 849-853, vol. 15.
Zhao, Bo et al., Nanotoxicity comparison of four amphiphilic polymeric micelles with similar hydrophilic or hydrophobic structure, Particle and Fibre Toxicology, 2013, 16 pps., vol. 10, No. 47.
Endocytic vesicle, Royal Society of Chemistry, 2019 (retrieved from the internet May 20, 2019), at www.rsc.org/publishing/journals/prospect/ontology.asp?id=GO:0030139&MSID=c1sm06846f, 1 p.
Xiao, Kai et al., PEG-oligocholic acid telodendrimer micelles for the targeted delivery of doxorubicin to B-cell lymphoma, Journal of Controlled Release, 2011, pp. 272-281, vol. 155.
Teramura, Yuji et al., Control of cell attachment through polyDNA hybridization, Biomaterials, 2010, pp. 2229-2235, vol. 31.

* cited by examiner

Fig. 3

| 30min | target: 300.000 WBC | | MW | STD | Mean % | STD % |
|---|---|---|---|---|---|---|
| well | | | | | | |
| a1 | well treated | 61470 | | | | |
| a2 | well treated | 67259 | | | 21,64 | 2,71 |
| a3 | well treated | 74951 | | | | |
| a4 | well treated | 55956 | 64909 | 8131,2 | | |
| b1 | untreated | 55575 | | | | |
| b2 | untreated | 32017 | | | 9,89 | 6,56 |
| b3 | untreated | 17166 | | | | |
| b4 | untreated | 11481 | 29059,75 | 19683,1 | | |
| c1 | WBC treated | 213072 | | | | |
| c2 | WBC treated | 237475 | | | 77,28 | 4,39 |
| c3 | WBC treated | 243445 | | | | |
| c4 | WBC treated | 233327 | 231829,75 | 13176,7 | | |

| 90min | target: 300.000 WBC | | MW | STD | Mean % | Mean % |
|---|---|---|---|---|---|---|
| well | | | | | | |
| a1 | well treated | 124492 | | | | |
| a2 | well treated | 143548 | | | 47,62 | 4,33 |
| a3 | well treated | 154212 | | | | |
| a4 | well treated | 149208 | 142865 | 13000,28 | | |
| b1 | untreated | 46601 | | | | |
| b2 | untreated | 29206 | | | 9,32 | 4,58 |
| b3 | untreated | 21199 | | | | |
| b4 | untreated | 14882 | 27972 | 13732,98 | | |
| c1 | WBC treated | 237185 | | | | |
| c2 | WBC treated | 252944 | | | 83,12 | 2,72 |
| c3 | WBC treated | 254697 | | | | |
| c4 | WBC treated | 252559 | 249346,25 | 8160,72 | | |

| 120min | target: 300.000 WBC | | MW | STD | Mean % | Mean % |
|---|---|---|---|---|---|---|
| well | | | | | | |
| a1 | well treated | 167671 | | | | |
| a2 | well treated | 177678 | | | 57,02 | 6,37 |
| a3 | well treated | 192194 | | | | |
| a4 | well treated | 146708 | 171062,75 | 19104,5 | | |
| b1 | untreated | 46402 | | | | |
| b2 | untreated | 35669 | | | 9,74 | 4,88 |
| b3 | untreated | 20989 | | | | |
| b4 | untreated | 13798 | 28214,5 | 14633,3 | | |
| c1 | WBC treated | 256949 | | | | |
| c2 | WBC treated | 268552 | | | 86,23 | 2,43 |
| c3 | WBC treated | 258291 | | | | |
| c4 | WBC treated | 250979 | 258692,75 | 7300,9 | | |

Fig. 6B
crude product:
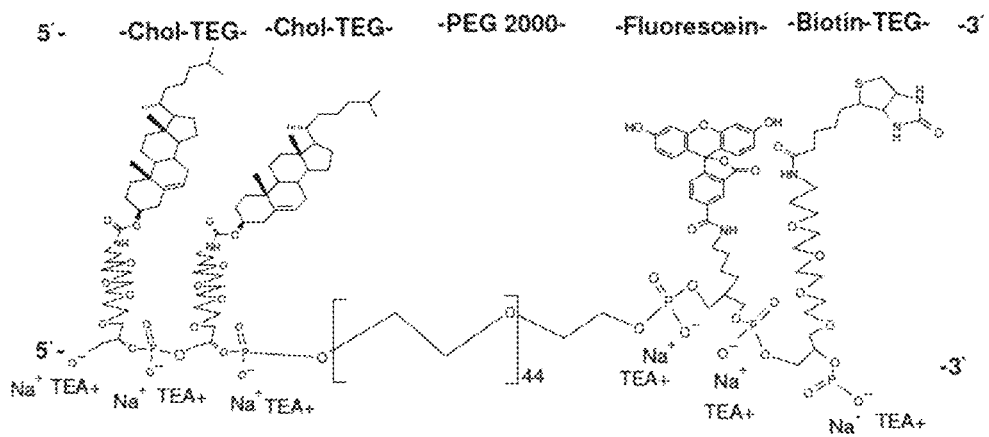
side product 1:
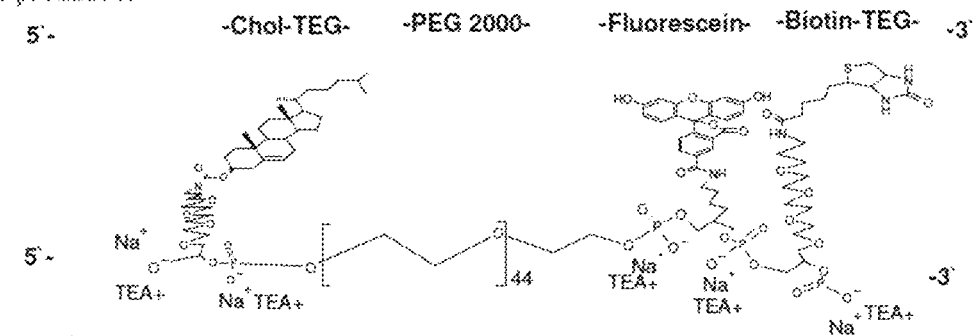
side product 2:
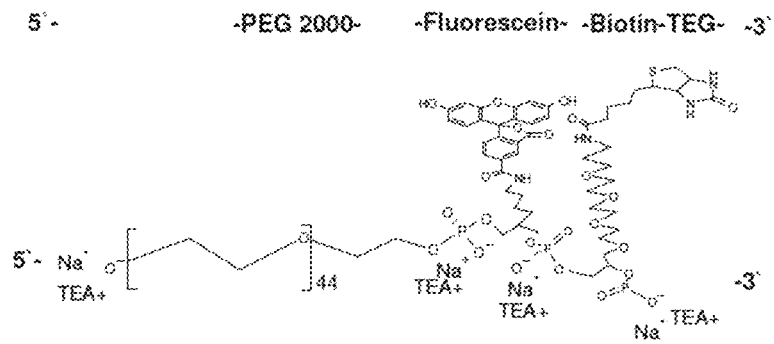
side product 3:
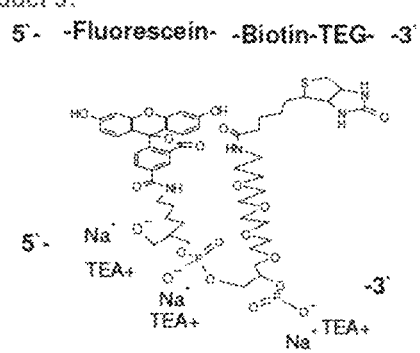
side product 4:
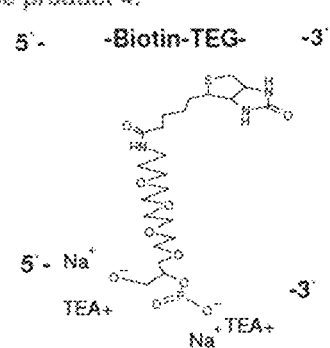

Fig. 6C
crude product:
5'- -myristic acid- -myristic acid- -PEG 2000- -Fluorescein- -Biotin-TEG- -3'
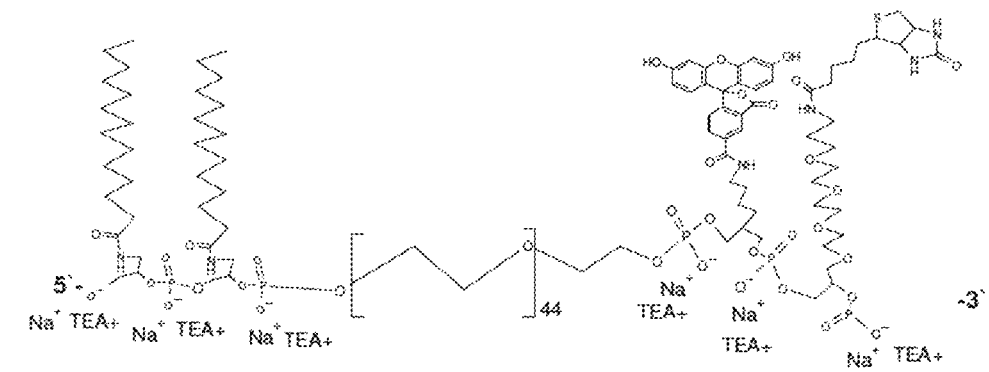
side product 1:
5'- -myristic acid- -PEG 2000- -Fluorescein- -Biotin-TEG- -3'
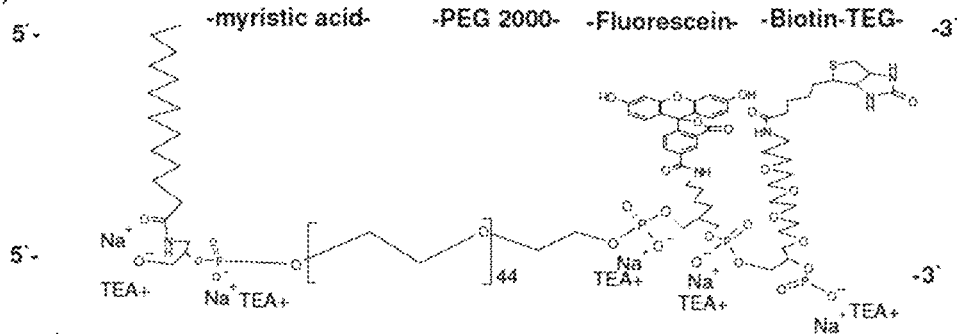
side product 2:
5'- -PEG 2000- -Fluorescein- -Biotin-TEG- -3'
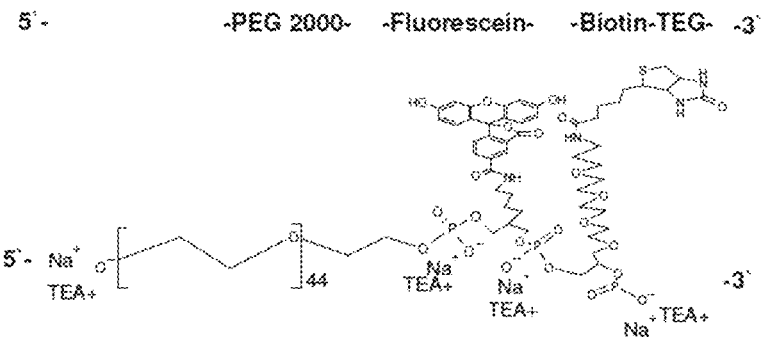
side product 3:
5'- -Fluorescein- -Biotin-TEG- -3'
side product 4:
5'- -Biotin-TEG- -3'
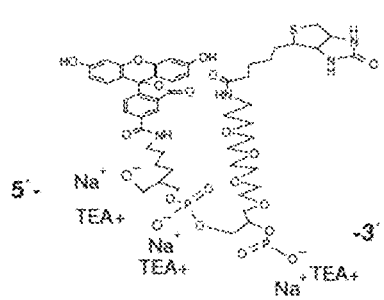
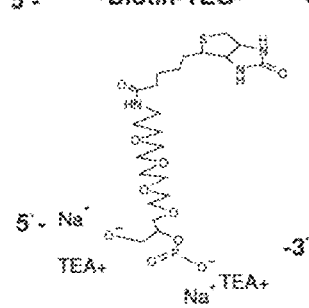

Fig. 6C (continued)
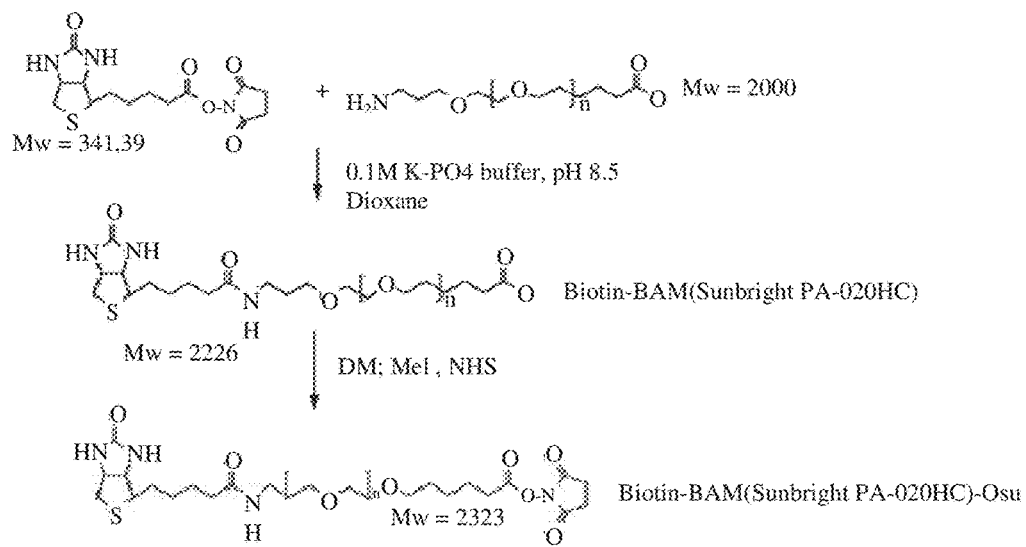
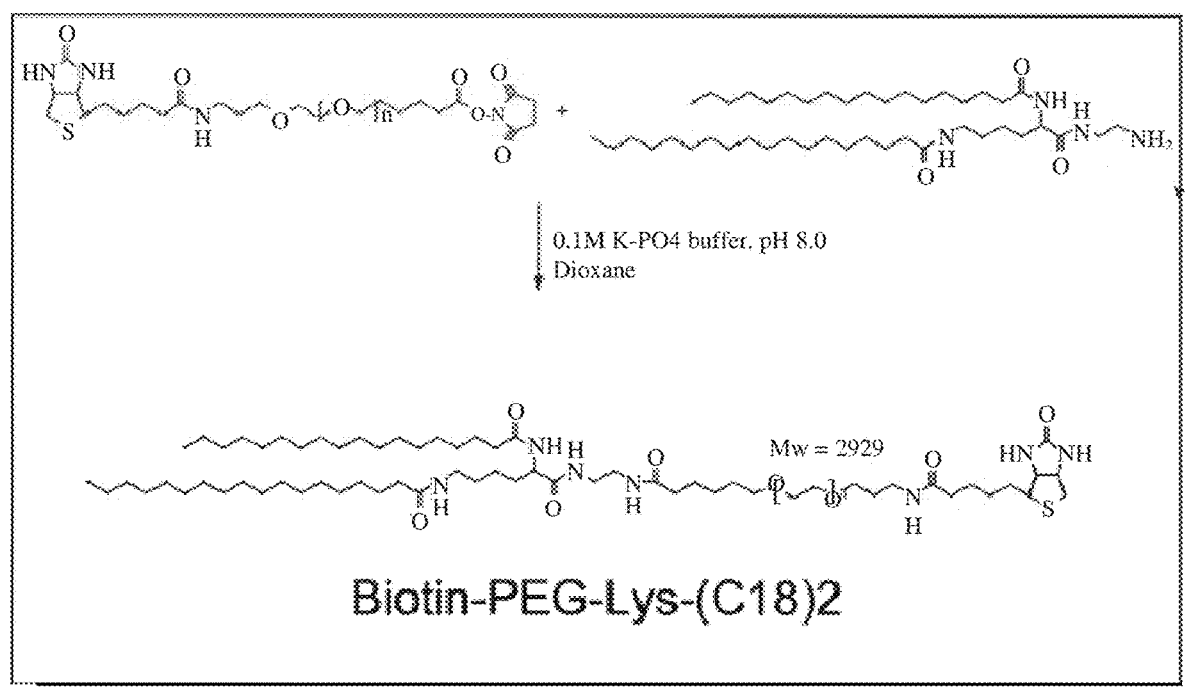

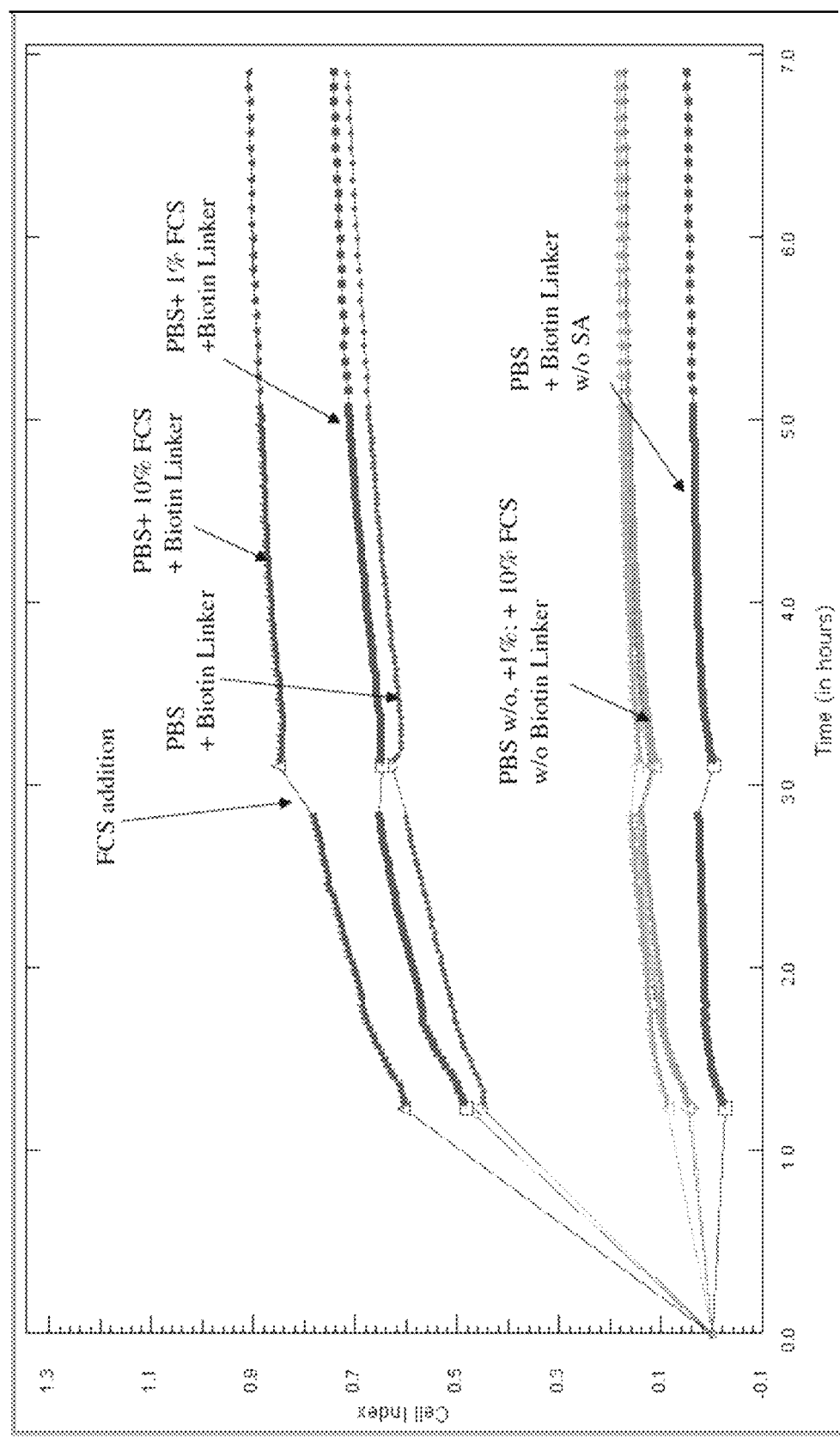

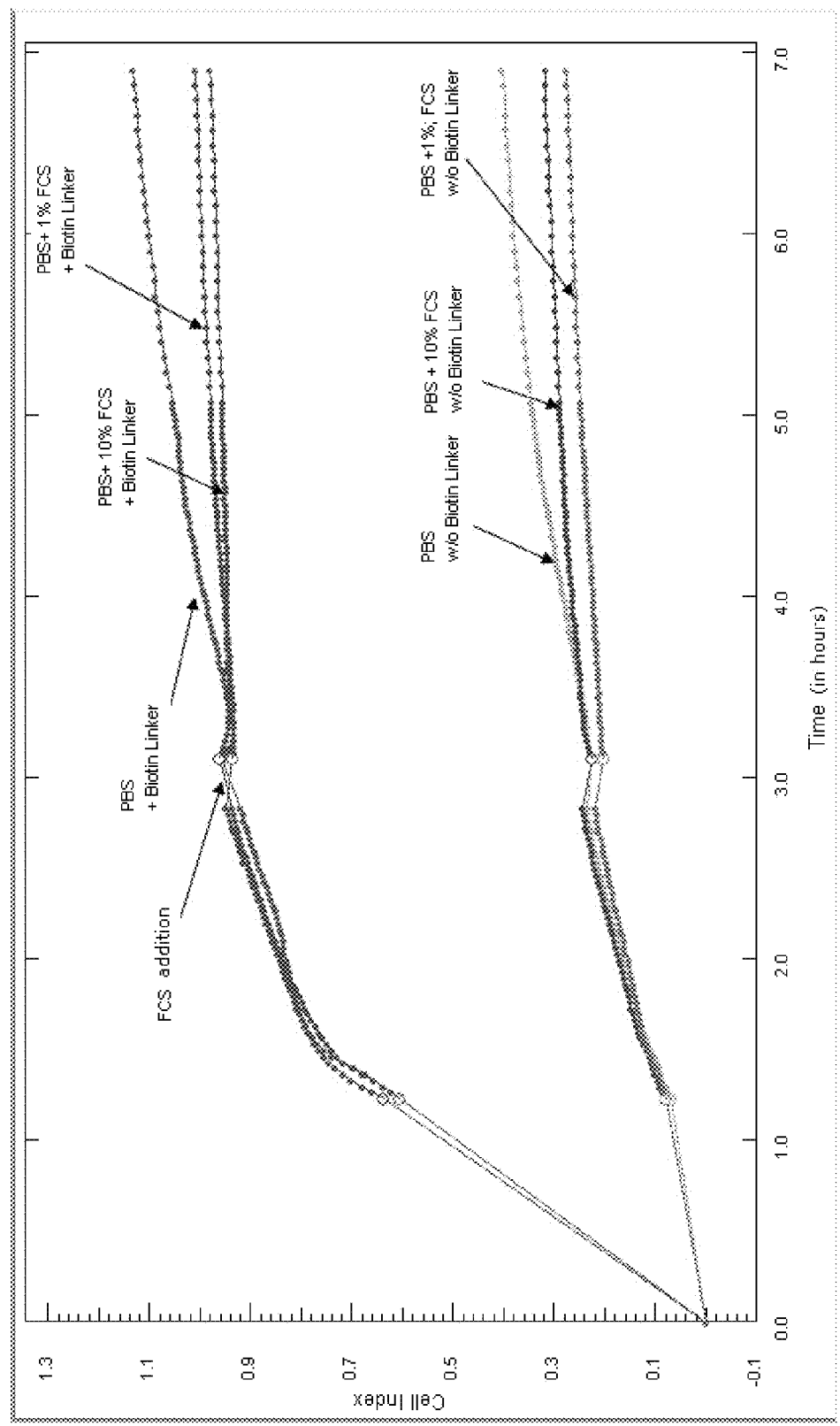

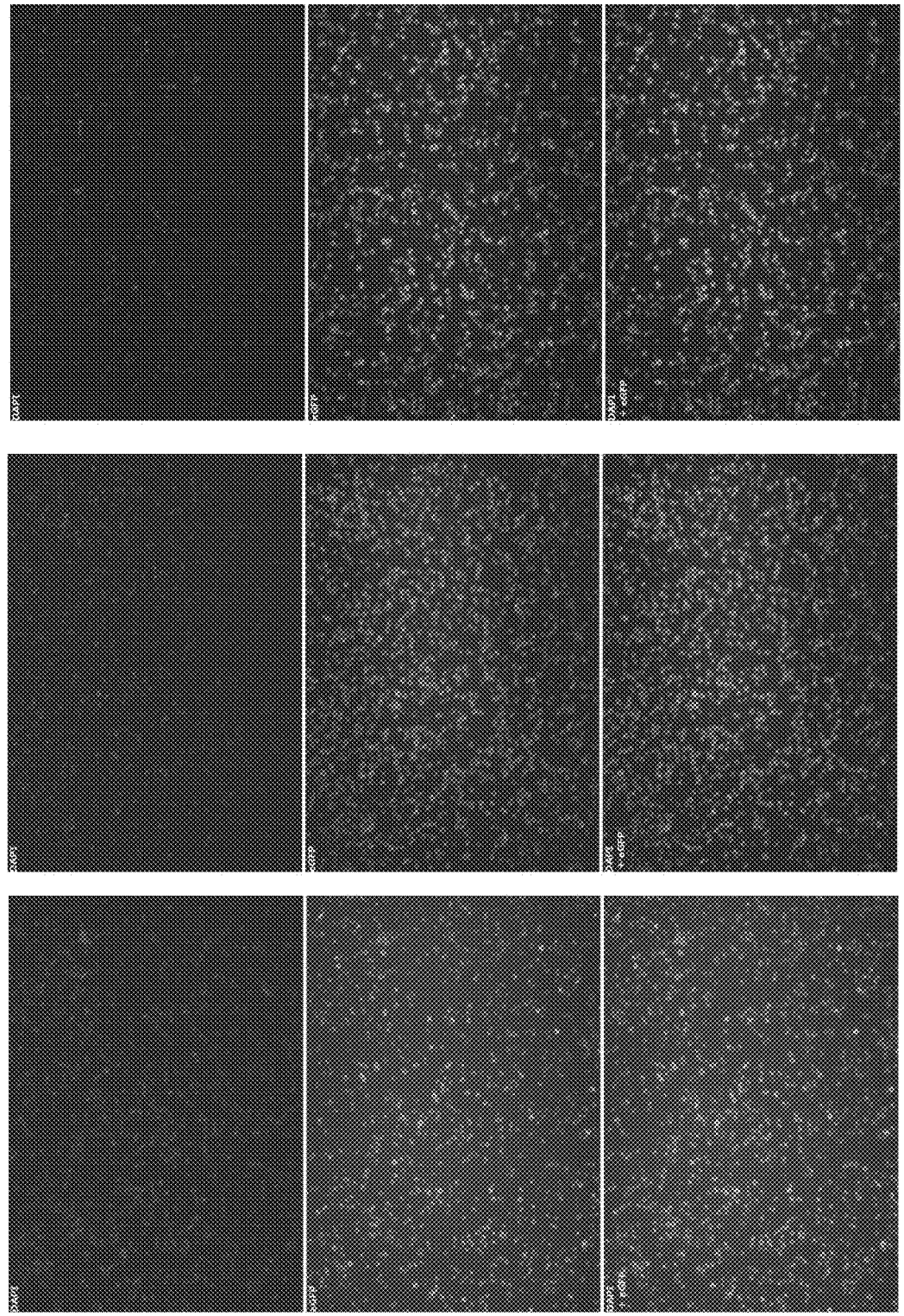

Fig. 12
29891272 Chol-TEG-Chol-TEG-Doubler-Biotin-dT
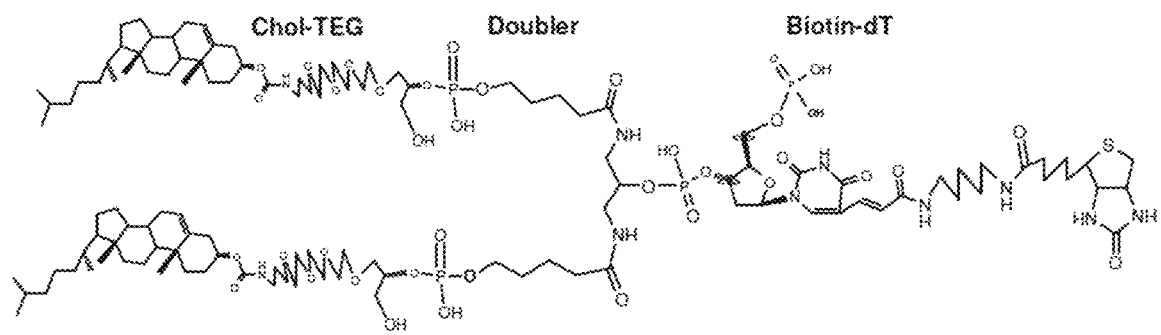
29891227 Myr-Chol-TEG-(Spacer-C18)₇-Fluos-Biotin-TEG
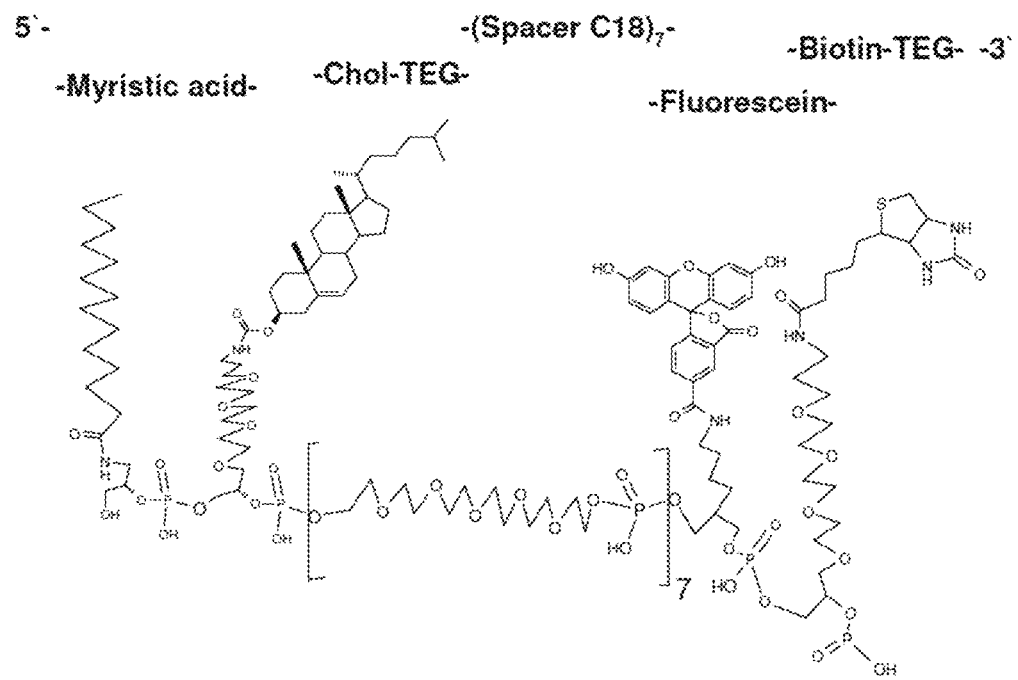

Fig. 12 (continued)
29891228  Chol-TEG- Myr-(Spacer-C18)₇-Fluos-Biotin-TEG
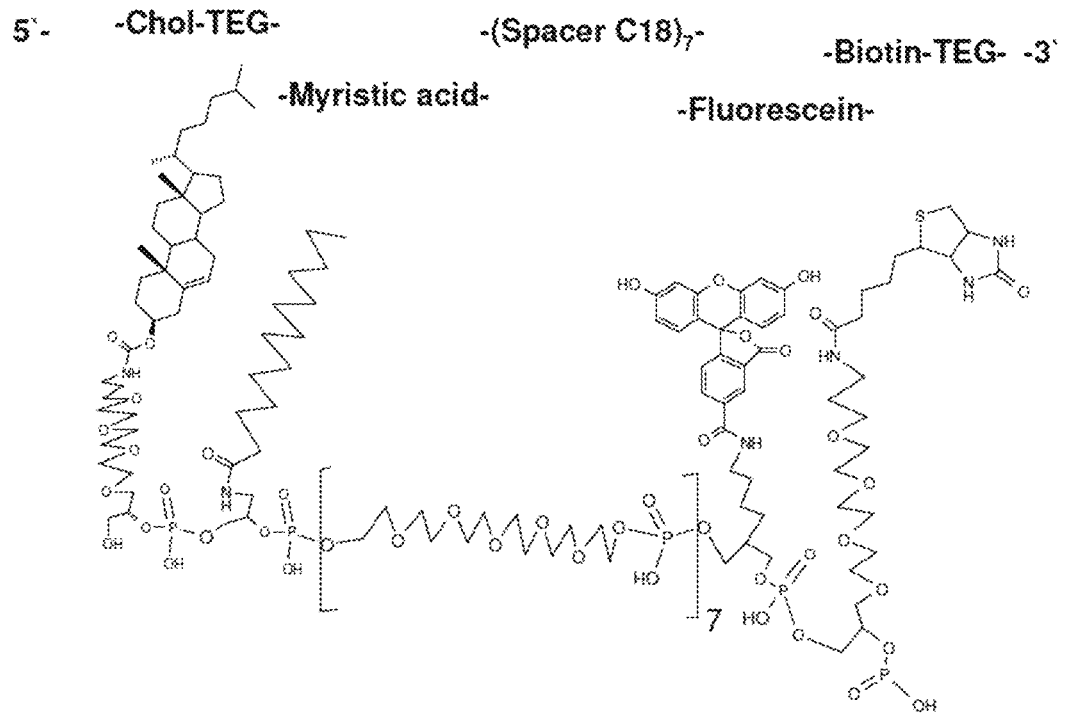
29891180  Chol-TEG-Chol-TEG-PEG2000-Fluos-Biotin-TEG
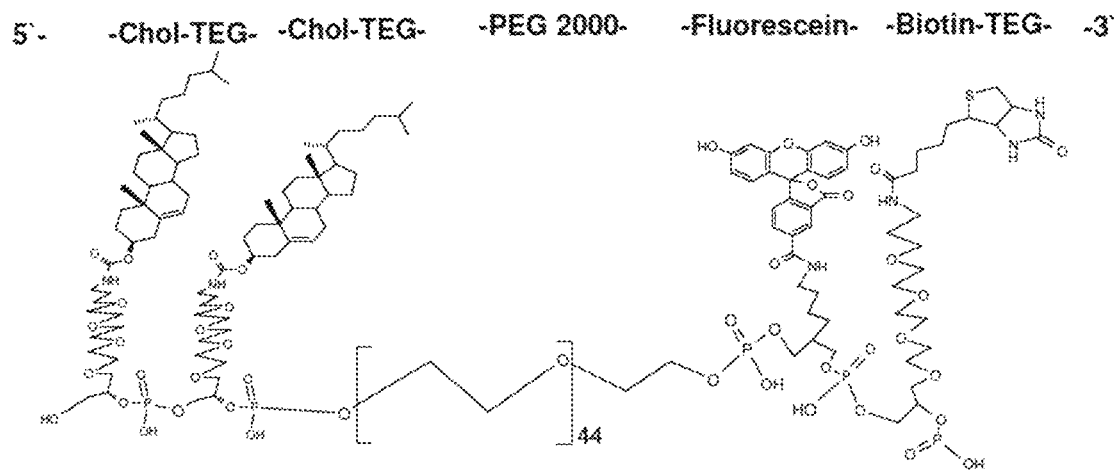

Fig. 12 (continued)
Phosphoramidites used for synthesis:
1 a)
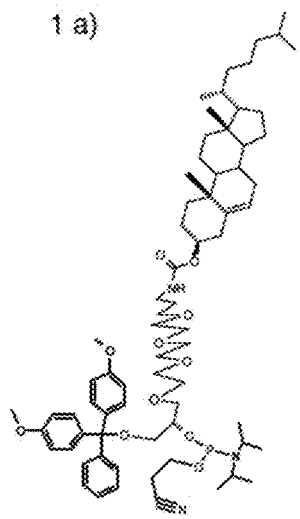
Cholesteryl-TEG-CE-phosphoramidite
a) cholesteryl-TEG-CE-PA (GlenResearch 10-1975),
1 b)
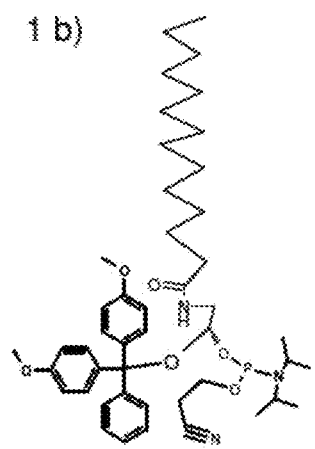
myristic acid-CE-phosphoramidite
b) myristic acid-CE-PA (inhouse production), Fig. 12 (continued)
1 c)
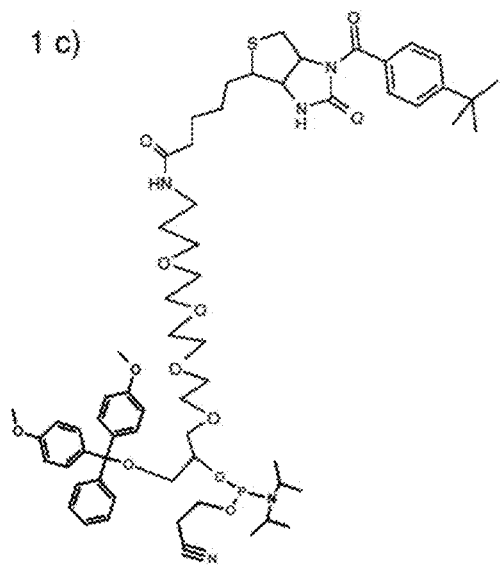
Biotin-TEG-CE-phosphoramidite
c) biotin-TEG-CE-PA (GlenResearch 10-1955),
1 d)
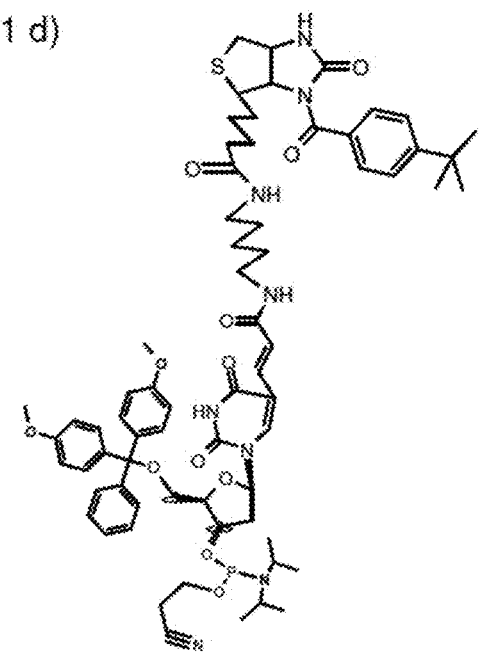
Biotin-dT-CE-phosphoramidite
d) biotin-dT-CE-PA (GlenResearch 10-1038),

Fig. 12 (continued)
1 e)
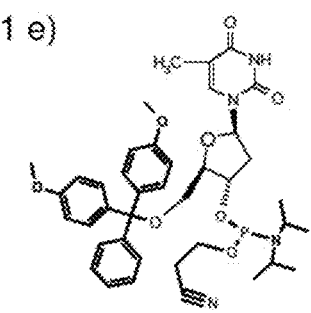
dT-CE-
phosphoramidite
1 f)
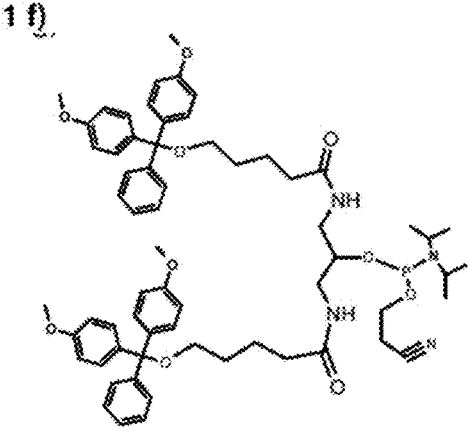
symmetric doubler-CE-
phosphoramidite
f) symmetric doubler-CE-PA (GlenResearch 10-1920),

Fig. 12 (continued)
1g.,
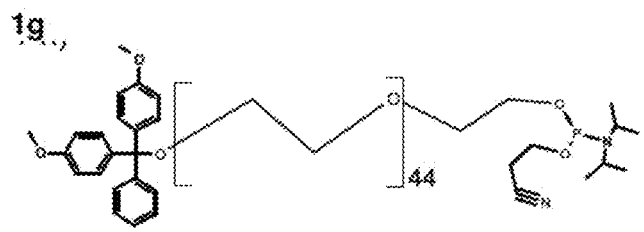
PEG-2000-CE-
phosphoramidite
g) PEG-200-CED-PA (ChemGenes CLP-2119),
1 h)
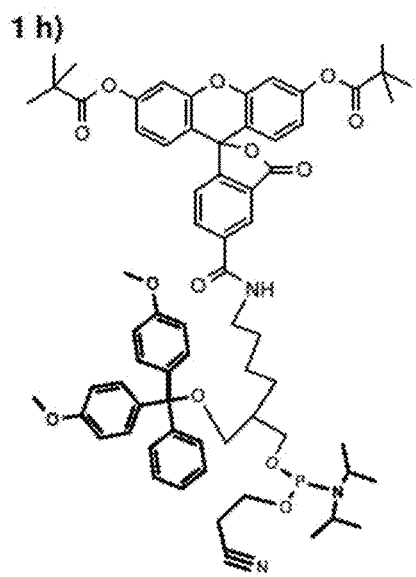
6-Fluorescein-CE-
phosphoramidite
h) 6-Fluorescein-CE-PA (GlenResearch 10-1964)

COMPOUNDS COMPRISING ONE OR MORE HYDROPHOBIC DOMAINS AND A HYDROPHILIC DOMAIN COMPRISING PEG MOIETIES, USEFUL FOR BINDING CELLS

BRIEF SUMMARY OF THE DISCLOSURE

The present invention relates to novel compounds comprising one or more hydrophobic domains and a hydrophilic domain comprising PEG moieties, useful for binding cells, as well as uses and compositions related thereto. The compounds are useful for immobilizing and/or stabilizing cells.

BACKGROUND OF THE DISCLOSURE

In US2005/0208644A1, a system employing two compounds is used for immobilizing cells. Disclosed therein is a method for immobilizing a cell in a desired pattern on a solid-phase surface by use of a chemical compound having an affinity for the cell. By using of another second chemical compound which is more easily immobilized on the solid-phase surface the first compound is bound to the second compound. The first chemical compound is described as a biocompatible anchor for membrane (BAM). This anchor has an aliphatic group which bines as it is inserted in the cell membrane and it can be immobilized by noncovalent bond without impairing the cells. Kato K. et al., Biotechnol. Prog. 2004, 20, 897-904: describes the so called BAMs (BAM90: one oleyl chain; DOPE-BAM80: dioleylphosphatidylethanolamine) to be useful as an anchoring reagent for proteins into cell membranes as a result of the high water solubility, rapid anchoring ability of the protein in to the outside leaflet of the cell membrane, high retention in the cell membrane and lack of cytolytic acitivity suggesting that this anchoring technique is promising for cell surface engineering." Kato K. Et al. BioTechniques 2003 35:1014-1021 describe suspension cell attachment by biocompatible anchor molecules, namely Oleyl-O-oly(ethylene glycol)-succinyl-N-hydroxysuccinimidyl-esters on surfaces.

However the compounds of the prior art have several disadvantages. Cell immobilization using such compounds is neither quantitative nor cell-type independent. Also, mixtures of different cell types, e.g. naturally occurring in a blood sample, cannot be attached to a surface quantitatively and independently of cellular phenotypes. In addition binding of the cells to the surface is not tight enough for subsequent processing steps, e.g. immunochemical staining and washing. Another disadvantage of the state-of-the art technology is that linker molecules described can either be internalized by cells or rejected by the cell, finally resulting in release and/or loss of cells.

Regarding the stabilization of cells, Octavio T. et al. (Biotechnology and Bioengineering 1990 36:911-920) describe the influence of a shear protective agent, Pluronic F-68 (Poloxamer 188) a non-ionic surfactant, on hybridoma grown under hydrodynamic stress. It is disclosed in the paper that shear sensitivity of mammalian cells can be a problem impeding development of large scale animal cell cultivation. Octavio et al. investigated the relationship between plasma membrane fluidity, shear sensitivity and the influence of shear protection reagents added to the culture medium. They have shown that plasma membrane fluidity is decreased by adding cholesterol to the medium and they showed that cell survival of cells subjected to selected shear rates is higher when adding cholesterol to the medium compared to the control group. The same effect has been shown for Pluronic F-68.

Tomeczekowski J. et al. 1993; Enzyme and microbial technology 15: 849-853 describes cholesterol as suitable, physiological agent to protect cells from shear stress by decreasing the plasma membrane fluidity.

Laura A. et al. (Enzyme and Microbial Technology 2000 26:324-331) describes Pluronic F-68 as shear protective agent for animal cells from hydrodynamic stress and they investigate the mechanism of action of Pluronic F-68. Laura et al. review on different other publications showing that Pluronic F-68 show two protection mechanisms, a physical and a biological/cellular mechanism. Pluronic F-68 reduces the level of frequency of forces experienced by the cells, e.g. it stabilizes the foam layer and decreases the rising velocity of bubbles, thus reducing shear forces. On a cellular level Pluronic F-68 reduces plasma membrane fluidity.

Similar disclosures are found in Thomas C. et al. (Advances in Bioprocess Engineering 1998: 137-171); Ramirez O. et al. (Biotechnological and Bioengineering 1990; 36:911-920), Michaels J. et al. (Biotechnological and Bioengineering 1991; 38:169-180) and Sowana D. et al. (Biochemical Engineering Journal 2002; 12:165-173).

However, cholesterol is a hydrophobic molecule and therefore it has to be dissolved in solvents like DMSO or alcohol which show cell toxicity at concentrations higher than 1% resulting in a limited cholesterol concentration which can be used to stabilize the cells.

In addition it has been shown that monovalent molecules like cholesterol or Pluronic F-68 have lower shear protective properties compared to bivalent molecules. Therefore the concentration of the monovalent protective agents, as already published, has to be higher compared to bivalent molecules.

Finally, monovalent molecules can be internalized into the cell interior and therefore can change the cell physiology.

There is therefore a need for new compounds and compositions which are able to bind to cells without affecting viability and/or which stabilize cells. For example, such compounds are useful for stabilizing cells, in particular for cells exposed to stress like shear stress, for visualizing cells and/or for immobilizing cells.

BRIEF DESCRIPTION OF THE FIGURES

Figures

FIG. 3: shows the results of Example 6 after 30, 90 or 120 minutes incubation.

FIG. 6B: The chemical structures of side products of the synthesis from FIG. 6A.

FIG. 8A: shows the results of the xCelligence experiments with Jurkat cells according to Example 3.

FIG. 9A: shows the results of the xCelligence experiments with WBC cells according to Example 3.

FIG. 10: shows the staining of immobilized cells, in accordance with Example 3. Left column: DA-MB468-antibody: K5/8. Middle column: MDA-MB468-antibody: EpCAM Miltenyi FITC. Right column: MDA-MB468-antibody: EGFR.

FIG. 12: shows structures of further compounds for use according to the invention and reference compounds, as well as intermediates.

DETAILED DESCRIPTION OF THE DISCLOSURE

Figure 1:
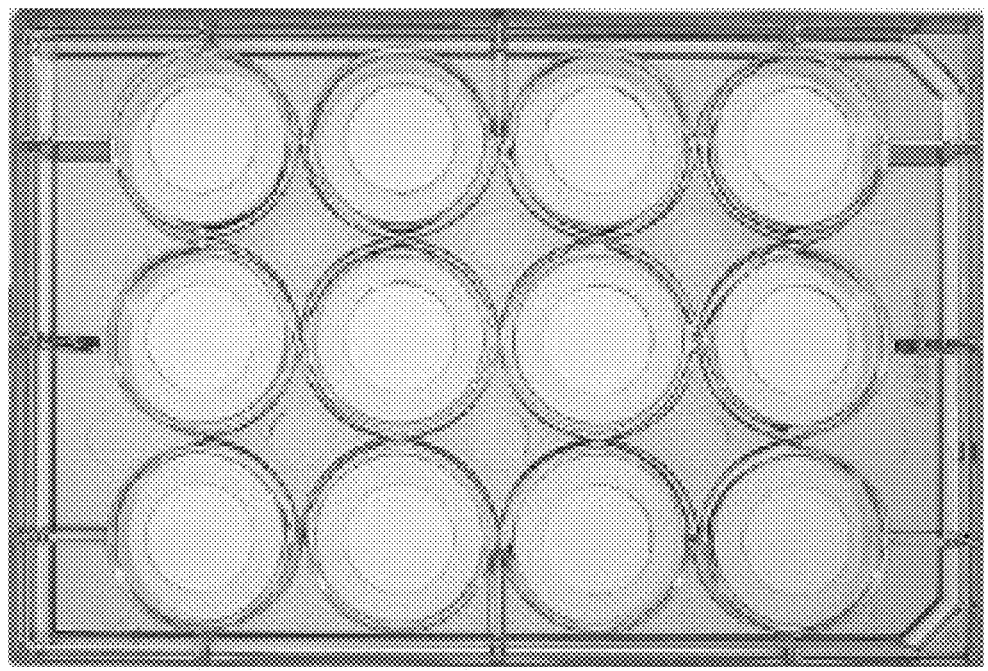
FIG. 1: Plate used in experiment of Example 6: Streptavidin treated MTP (Microcoat), 12 Well, NUNC, MC ID: 604 176, Lot Nr: 1665 C2

The compounds and compositions of the invention solve this problem and overcome the disadvantages of the prior art. The compounds of the invention are in particular able to capture all types of cells, encompassing suspension and adherent cells and effectively stabilize cells.

In one embodiment, the present invention relates to a compound comprising, preferably consisting of, one or more hydrophobic domains and a hydrophilic domain, wherein the one or more hydrophobic domains are covalently bound to said hydrophilic domain, and wherein the one or more hydrophobic domains each comprise a linear lipid, a steroid or a hydrophobic vitamin, and wherein the hydrophilic domain comprises a compound of Formula (I):

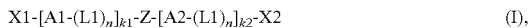

$$X1\text{-}[A1\text{-}(L1)_n]_{k1}\text{-}Z\text{-}[A2\text{-}(L1)_n]_{k2}\text{-}X2 \qquad (I),$$

wherein

Z is linear polyethylene glycol (PEG) moiety containing 1 to 100, preferably 1 to 50, more preferably 4-30-O—CH2-CH2- moieties, wherein the polyethylene glycol moiety optionally comprises 1 or more spacer moieties SP connecting two —O—CH2-CH2- moieties, and wherein the linear PEG moiety optionally comprises a linker moiety L3 at one or both ends, each L1 is a linker moiety selected independently from each other, each n is either 0 or 1, selected independently from each other, A1 and A2 are bifunctional or trifunctional moieties selected independently from each other, with the proviso that at least one A1 or A2 is trifunctional, k1 and k2 are integers between 0 and 10, selected independently from each other, with the proviso that at least one of k1 and k2 is not 0, X1 and X2 are independently selected from hydrogen or a protecting group, L3 is a linear alkyl or alkenyl chain with 1 to 10 C atoms, which is optionally (i) interrupted by 1 to 3 N, O or S atoms, and/or (ii) substituted by 1 to 4 hydroxyl, carbonyl, amino or thiol groups, and wherein the one or more hydrophobic domains are covalently bound to said hydrophilic domain via the trifunctional domain(s), or a salt thereof.

A lipid is a hydrophobic small molecule selected from fats, waxes, sterols, fat-soluble, hydrophobic vitamins, such as vitamins A, D, E, and K, fatty acids monoglycerides, diglycerides, triglycerides and phospholipids.

A hydrophobic vitamin is a small molecule selected from the group consisting of vitamins A, D, E, and K. In a more preferred embodiment, the hydrophilic vitamin is α-tocopherol. An exemplary compound of the invention comprising α-tocopherol is 5'-α-TocopherolTEG-PEG2000-Fluos-3'.

The compounds of the invention comprise, preferably consist of, one or more hydrophobic domains and a hydrophilic domain.

Preferably, 1, 2, 3, 4, 5, 6, 7, 8, 9 or 10 hydrophobic domains are covalently bound to said hydrophilic domain.

For stabilizing effects, it was found advantageous that the compounds of the invention preferably comprise 2 or 3 or more, more preferably 2 or 3 hydrophobic domains. With particular advantage, in a specific embodiment at least one lipid hydrophobic domain comprises a steroid.

In one preferred embodiment of the invention, 2 or 3 or more, more preferably 2 or 3 hydrophobic moieties hydrophobic domains are covalently bound to said hydrophilic domain.

For the general understanding herein, a "hydrophobic moiety" is comprised in and forms the major portion of a "hydrophobic domain", thus determining the hydrophobic character thereof.

The hydrophobic moieties for compounds comprising 2 or more hydrophobic moieties may be the same or may be different. For example, a compound comprising two hydrophobic domains may comprise 2 myristic acid moieties, or a myristic acid moiety and a cholesteryl moiety.

The hydrophobic domains each comprise, preferably consist of, a linear lipid, a steroid or a hydrophobic vitamin.

The linear lipid, steroid or hydrophobic vitamin may be bound directly to a trifunctional moiety or via a linker L2. An example for compounds wherein a linear lipid, steroid or hydrophobic vitamin is bound directly to a trifunctional moiety is compound myristic acid-myristic acid-(SpacerC18)7-Fluos-Biotin-TEG. An example for compounds wherein a linear lipid, steroid or hydrophobic vitamin is bound via a linker L2 to a trifunctional moiety is compound Cholesteryl-TEG-Cholesteryl-TEG-(SpacerC18)7-Fluos-Biotin-TEG. In this latter example, TEG (tetraethylenglycol) is the linker L2.

In one preferred embodiment, the hydrophobic domains each consist of a linear lipid, a steroid or a hydrophobic vitamin. In this event, it is apparent that the hydrophobic domain is hydrophobic, more preferably lipophilic as a linear lipid, a steroid or a hydrophobic vitamin is hydrophobic, more preferably lipophilic.

A hydrophobic moiety is understood as moiety that is repelled from a mass of water. Preferably, the moiety is lipophilic; i.e. it tends to dissolve in other non-polar lipophilic substances like fats or fatty acids.

In another preferred embodiment, the hydrophobic domains each comprise a linear lipid, a steroid or a hydrophobic vitamin and one or more further moieties. In this embodiment, the hydrophobic moiety as a whole is hydrophobic, more preferably lipophilic.

In an even more preferred embodiment, the hydrophobic domains of the invention comprising a linear lipid, a steroid or a hydrophobic vitamin are able to insert into a cell membrane. This can be determined by methods known in the art.

In one preferred embodiment, the 2 or 3 hydrophobic moieties of a compound of the invention are different hydrophobic domains, or in case of 3 hydrophobic moieties, two are different from the third or all three are different from each other.

In this latter preferred embodiment of the invention, a first hydrophobic domain comprises, preferably consists of, a saturated fatty acid, especially myristic acid, stearic acid or behenic acid, particularly myristic acid, and/or a second hydrophobic domain comprises, preferably consists of, cholesterol. In case of a third hydrophobic domain, this domain preferably comprises, preferably consists of, cholesterol or a saturated fatty acid, especially myristic acid, stearic acid or behenic acid, particularly myristic acid and/or is the same as the first or second hydrophobic domain.

The basic principle for binding to cells and immobilizing cells of the compounds of the invention is that a terminal hydrophobic part of the compound of the invention anchors into the lipid bi-layer of a cell membrane of interest. The cell can then for example be afterwards attached to a specifically modified surface, and/or can be labeled for visualization and/or detection. Moreover, mixtures of such compounds can be used for binding all cell types. Depending on the hydrophobic part, also preferential or exclusive binding to specific cells can be achieved.

Moreover, the compounds of the invention surprisingly exhibit advantageous stabilizing effects on cells and/or binding or immobilizing effects on cells, as shown in detail in the Examples.

In particular, compounds comprising a cholesterol moiety as a hydrophobic moiety are especially preferred.

The stabilizing, in particular shear-protective effect is in particular proven for cholesterol, myristic acid and stearic acid as hybrophobic moieties in the compounds of the invention (see Example 5).

The basic principle is postulated to be that a terminal hydrophobic part of the binding molecule anchors into the lipid bi-layer of the cell membrane. This hydrophobic molecule immobilization decreases the plasma membrane fluidity and therefore stabilizes the cell.

For stabilizing effects, the compounds of the invention preferably comprise 2 or 3 or more, more preferably 2 or 3 hydrophobic moieties.

This conformation was shown to have a higher binding affinity to the cells compared to monovalent molecules; i.e. molecules comprising one hydrophobic moiety of the invention. Therefore lower concentrations of the molecules of the invention are needed to reach a shear protective effect compared to monovalent molecules.

The hydrophilic part of the molecule inhibits the internalization of the compound of the invention and the shear protective effect is induced by incorporating of the hydrophobic part into the exterior plasma membrane. Experiments with labeled compounds of the invention have confirmed that the compound just incorporates in the exterior plasma membrane without influencing the cell interior.

Regarding the application of cell labelling and immobilization, it was found in the Examples that compounds with hydrophobic moieties show a targeting and tight retaining of all cell types (see in particular Example 2). In particular cholesterol, myristic acid, stearic acid, and behenic acid moieties are found to be in particular useful in compounds of the invention for this purpose. With exemplary advantage and allowing to achieve quantitative cell targeting, compound 5'-CholesterylTEG-CholesterylTEG-PEG2000-Fluos-3 (internal Ref: BMO 29.891133) represents a preferred embodiment of the present invention.

Also, it was found that compounds containing one, two or three hydrophobic moieties were proven in experiments to be useful for quantitative cell immobilization.

According to the present invention, a "cholesterol-dual linker molecule" is understood as compound of the invention containing two hydrophobic moieties, which are both cholesterol. Accordingly, a "myristic acid-triple linker molecule" is understood as compound of the invention containing three hydrophobic moieties, which are all myristic acid.

According to the invention "asymmetric dual linker molecule" is understood as compound of the invention containing two hydrophobic moieties, wherein the two hydrophobic moieties are different from each other.

The compounds of the invention are described in the examples mostly in this modular, schematic way.

Figure 6A:
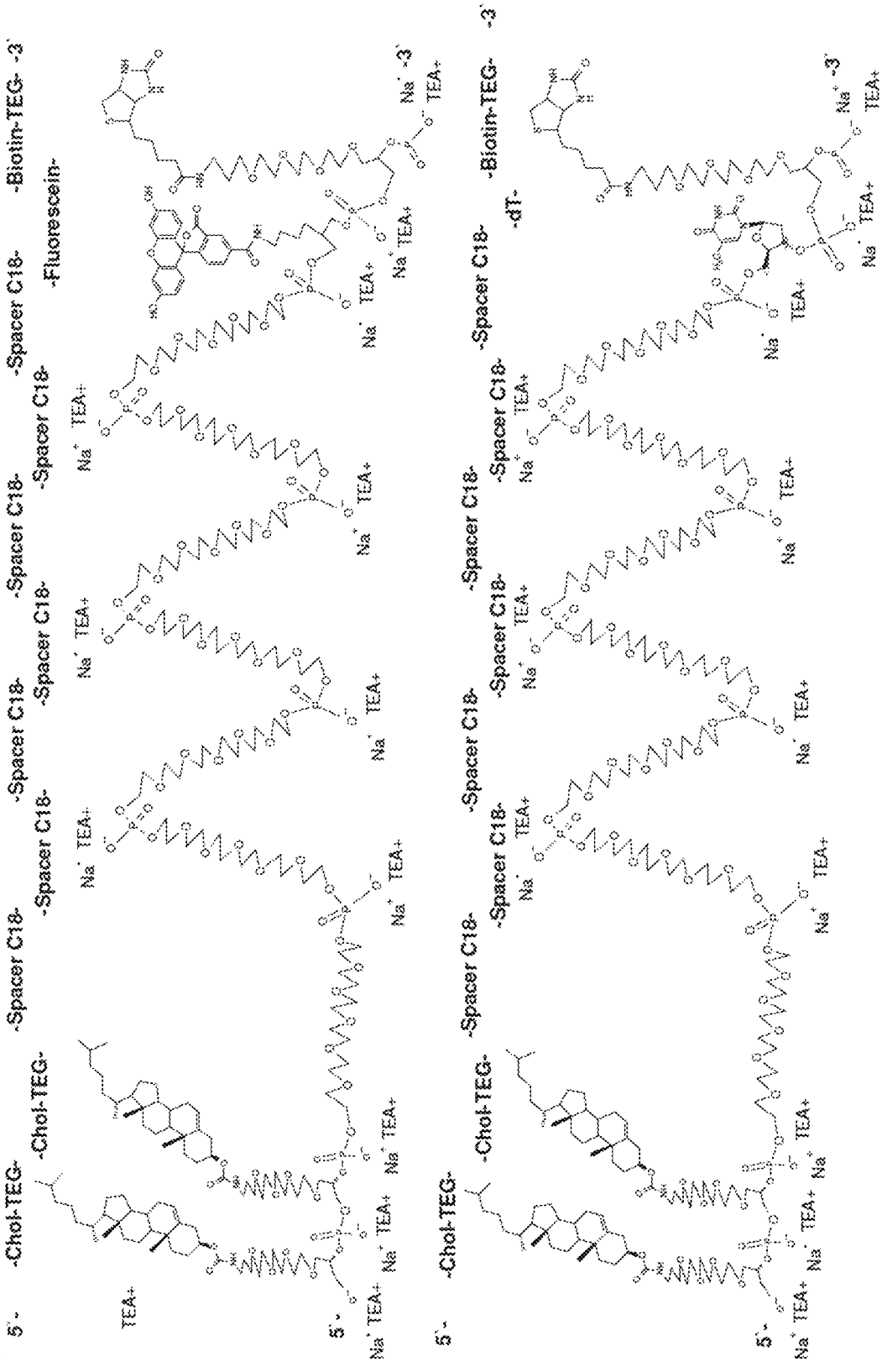
FIG. 6A: The chemical structures of exemplary compounds for use according to the invention

According to the present invention, the a compound "Cholesteryl-TEG-Cholesteryl-TEG-(SpacerC18)7-Fluos-Biotin-TEG" as shown in FIG. 6 A) is understood as a compound wherein two cholesterol moieties as hydrophobic moieties are bound to a trifunctional moiety via TEG (tetraethylenglycol).

In accordance with FIG. 6, which shows the modular description of the compounds of the invention in parallel to the chemical formula, "(SpacerC18)" is understood as PEG moiety of a length of 18 atoms followed by a phosphate moiety as spacer moiety. -(SpacerC18)7- is accordingly understood as a moiety consisting of 7 "(SpacerC18)" moieties.

According to the present invention "Fluos" is understood as fluorescein moiety bound directly to a trifunctional moiety A2.

According to the present invention "Biotin-TEG" is understood as biotin moiety bound via a linker TEG to a trifunctional moiety A2.

In case of the compounds of the invention disclosed in this schematic way, the trifunctional moiety A1 typically is glycerol for TEG bound-hydrophobic moieties (see FIG. 6 A). In addition, embodiments with serinol or 6-[(2-hydroxyethyl)amino]-1-Hexanol replacing glycerol as trifunctional moiety are equally disclosed. Other alternatives for such trifunctional moieties are available to the skilled artisan.

The trifunctional moiety A1 is serinol for the compound of FIG. 6 A, wherein the hydrophobic moieties are bound directly to a trifunctional moiety A1.

In an even more schematic way, "Cholesteryl-TEG-Cholesteryl-TEG-(SpacerC18)7-Fluos-Biotin-TEG" can be described to be of the structure "5'-XXYYYYYYYFZ-3'", wherein Y= is a PEG+spacer moiety, X is a hydrophobic moiety bound to the hydrophilic moiety via a trifunctional linker, F is a fluorescent label fluorescein, and Z is a linking group (biotin). 5' and 3' indicate the direction of synthesis by an automated synthesis as shown in the Examples in analogy to nucleotides.

Analogously, -PEG2000- is understood as a PEG2000 moiety; i.e. a polyethylenglycole (PEG) chain consisting of 45 $C_2H_6O_2$ subunits.

In the compounds of the invention described in the experimental part, L1 is present (n=1) and is phosphate if not explicitly indicated otherwise.

"Spacer" in the context of specifically disclosed compounds of the invention in the Examples is understood as PEG-moiety including a phosphate moiety. The length of the PEG moiety is determined by e.g. C9 or C12, which indicates that the PEG moiety has a length of 9 or 12 atoms, respectively.

"dT" is understood as thymidine, as exemplified in FIG. 6 B). This moiety dT can be used for determining the concentration of the compounds by absorption and is a bifunctional moiety according to the present invention.

In particular, it was found that a cholesterol-dual linker molecule, a myristic acid-dual or triple linker molecule as well as a stearic acid-dual linker molecule were suitable to achieve quantitative cell immobilization using white blood cells and different cultured cell lines. Moreover, a combination of a cholesterol-dual linker and a myristic-dual linker molecule show a weak increase of the immobilization rate of some cell types compared to the single dual linker molecules.

It has also been shown that an asymmetric dual linker containing both a cholesterol moiety and a myristic acid moiety also show a quantitative cell immobilization.

Moreover, molecules of the invention containing 2 or 3 hydrophobic molecules covalently bound to the hydrophilic domain exhibit a tight binding of cells, potentially utilizing a cooperative binding effect. The binding of such molecules to cells is 100-1000 fold stronger compared to binding or immobilization using a compound containing only one hydrophobic molecule.

Furthermore, it is preferred in one embodiment, that the two or three hydrophobic molecules are separated spatially by using linker moieties L1. This is in particular useful for a quantitative immobilization of cells. Utilizing suitable linkers, tailored binding molecules are obtained, being ideally suited e.g. for targeting and immobilizing all kinds of rare and regular cells from blood.

In such preferred embodiment, n=1, and L1 is therefore present.

The hydrophilic domain of compounds of the invention comprises a PEG moiety and is therefore flexible.

The terminal hydrophobic part(s) of the compounds of the invention is followed by a long flexible hydrophilic domain.

This hydrophilic domain allows a flexible folding around the cells of interest required for safe embedding of cells, thereby generating a cell-friendly, hydrogel-like environment which is important for keeping the cell morphology and functions alive.

It is possible to use different linear PEG moieties, which differ in length and/or in comprising Spacer moieties like phosphate between PEG moieties in order to achieve a flexible hydrophilic domain. For example a polyethylenglycole (PEG) chain consisting of 45 $C_2H_6O_2$ subunits (PEG2000) (see Example 6 B)) or PEG-moieties with phosphate spacers like -(SpacerC18)7- as described above may be used.

Suitable protecting groups are known in the art. Suitable protecting groups for phosphoramidite chemistry are for example (4,4'-dimethoxytrityl (DMT), and fluorenomethoxycarbonyl (Fmoc). A particularly preferred protecting group is DMT (4,4'-dimethoxytrityl).

Various salts of compounds of the invention can be used like Na+ and/or TEA+ salts of compounds of the invention, as shown in FIG. 1.

Also other salts are possible and are known to a skilled person. Preferably, salts are used which do not affect or not substantially affect cell viability or function.

In a preferred embodiment of the present invention, the moiety Z has the following structure:

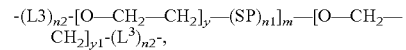

wherein
SP is a spacer moiety,
each spacer moiety SP is selected independently from each other,
each n1 is either 0 or 1, selected independently for each m moieties,
each n2 is either 0 or 1, selected independently of each other,
m is an integer from 1 to 100, preferably 1 to 50, more preferably 4 to 30,
y is an integer from 1 to 100, preferably 1 to 50, more preferably 4 to 30,
y1 is an integer from 0 to 30, preferably 0 to 10, more preferably 0 to 4,
with the proviso that y*m+y1≤100
and wherein L3 is as defined above.

In a further preferred embodiment of the present invention, n1 is identical for the m moieties —[O—$CH_2$—$CH_2$]$_y$—(SP)$_{n1}$]—.

As can be seen from the examples, n1 is typically either always 0 in compounds of the invention, or always 1 in compounds of the invention.

An exemplary compound wherein n1=1 is Cholesteryl-TEG-SpacerC12-Cholesteryl-TEG-(SpacerC18)7-Fluos-Biotin-TEG.

An exemplary compound wherein n1=0 is Cholesteryl-TEG-Cholesteryl-TEG-PEG2000-Fluos-Biotin-TEG.

In a further preferred embodiment of the present invention, y1 is 0.

An exemplary compound where y1=0 is Cholesteryl-TEG-SpacerC12-Cholesteryl-TEG-(SpacerC18)7-Fluos-Biotin-TEG.

In a further embodiment of the present invention, y1 is 1.

An exemplary compound where y1=1 is 5'-CholesterylTEG-CholesterylTEG-(SpacerC18)7-SpacerC3-dT-BiotinTEG-3'.

In a further preferred embodiment of the present invention, y is 3, 4, 5, or 6, and n1 is 1. Even more preferably m is 3, 4, 5, 6, 7, 8, 9 or 10.

In a further preferred embodiment of the present invention, the spacer moieties SP are independently from each other selected from the group consisting of a phosphate, and a bifunctional moiety.

It is preferred that all spacer moieties SP are the same. Even more preferably, all moieties SP are phosphate.

A bifunctional moiety according to the present invention is understood as moiety containing two functional groups prior to the synthesis of a compound of the invention. Such bifunctional moiety is therefore suitable for synthesis of linear compounds. Suitable bifunctional groups are preferably selected from the group consisting of a phosphate group, carbamate group, amide group, a moiety comprising a nucleobase, even more preferably dT, and a linear alkyl group having 1 to 10 C atoms, in particular 1, 2, 3, 4, 5, 6, 7, 8, 9 or 10 atoms, and which alkyl chain contains functional groups at the terminal C-atoms, in particular independently selected from amine, carbonyl, hydroxyl, thiol, carbonic acid groups. Examples of suitable linear alkyl groups with terminal functional groups are diaminoalkyl moieties such as $H_2N-(CH_2)_5-NH_2$ or hydroxyl-carbonyl moieties such as $-C(O)-(CH_2)_4-O-$.

A trifunctional moiety according to the present invention is understood as moiety containing three functional groups prior to the synthesis of a compound of the invention. Such trifunctional moiety is therefore suitable for synthesis of a branched compound. Suitable trifunctional moieties are preferably selected from a trifunctional moiety having 1 to 10 C atoms, in particular 1, 2, 3, 4, 5, 6, 7, 8, 9 or 10 C atoms and comprising at least one —OH, —SH and/or at least one —NH2 group, more preferably selected from an amino acid, such as lysine or serine, serinol, $-O-CH2-CH((CH_2)_4-NH_2)-CH2-$, glycerol, and a 1,3 diaminoglycerol moiety.

In a further preferred embodiment of the present invention, X1 and/or X2, preferably X1 or X2 is replaced by a hydrophobic domain. An exemplary compound wherein X1 is replaced by a hydrophobic domain is Biotin-PEG-Lys-(C18)2 as shown in the Examples.

In a further preferred embodiment of the present invention, n2 is both 0. In such embodiment, the central linear PEG moiety is directly bound to the moieties X1-[A1-(L1)n]k1 and [A2-(L1)n]k2-X2.

In a further preferred embodiment of the present invention, one or both n2=1, and L3 is an alkyl group with 1 to 10 C atoms which optionally contains an amide group, carbonyl group, carbamate, and/or NH group In a further preferred embodiment of the present invention, L3 is an alkyl group with 1 to 10 C atoms which optionally contains an amide group, carbonyl group, carbamate, and/or NH group. For example one L3 may be $-NH-CH_2-CH_2NHCO-CH_2-CH_2-$ as in the compound Biotin-PEG2000-Lys-(C18)$_2$ of the invention.

In a further preferred embodiment of the present invention, the linear lipid is (a) a saturated or unsaturated fatty acid, and/or
(b) a fatty acid having from 8 to 26 C atoms, preferably from 12 to 22 C atoms, more preferably from 14 to 18 C atoms.

A fatty acid is a carboxylic acid with a long aliphatic tail (chain), which is either saturated or unsaturated. Most naturally occurring fatty acids have a chain of an even number of carbon atoms, from 4 to 28.

Examples of saturated fatty acids are caprylic acid, capric acid, lauric acid, myristic acid, palmitic acid, Stearic acid, arachidic acid, Behenic acid, lignoceric acid, and Cerotic acid.

Examples of suitable unsaturated fatty acids are:

| Common name | Δx | Chain length:Double bond |
|---|---|---|
| Myristoleic acid | cis-Δ9 | 14:1 |
| Palmitoleic acid | cis-Δ9 | 16:1 |
| Sapienic acid | cis-Δ6 | 16:1 |
| Oleic acid | cis-Δ9 | 18:1 |
| Elaidic acid | trans-Δ9 | 18:1 |
| Vaccenic acid | trans-Δ11 | 18:1 |
| Linoleic acid | cis,cis-Δ9,Δ12 | 18:2 |
| Linoelaidic acid | trans,trans-Δ9,Δ12 | 18:2 |
| α-Linolenic acid | cis,cis,cis-Δ9,Δ12,Δ15 | 18:3 |
| Arachidonic acid | cis,cis,cis,cis-Δ5Δ8,Δ11,Δ14 | 20:4 |
| Eicosapentaenoic acid | cis,cis,cis,cis,cis-Δ5,Δ8,Δ11,Δ14,Δ17 | 20:5 |
| Erucic acid | cis-Δ13 | 22:1 |
| Docosahexaenoic acid | cis,cis,cis,cis,cis,cis-Δ4,Δ7,Δ10,Δ13,Δ16,Δ19 | |

In an even more preferred embodiment, the linear lipid is selected from the group consisting of oleic acid, myristic acid, stearic acid and behenic acid, more preferably selected from myristic acid and oleic acid.

In a further preferred embodiment a steroid can be used as hydrophobic moiety.

A steroid is a type of organic compound that contains a characteristic arrangement of four cycloalkane rings that are joined to each other. The core of steroids is composed of seventeen carbon atoms bonded together that take the form of four fused rings: three cyclohexane rings (designated as rings A, B and C) and one cyclopentane ring (the D ring). The steroids vary by the functional groups attached to this four-ring core and by the oxidation state of the rings. Sterols are special forms of steroids, with a hydroxyl group at position-3 and a skeleton derived from cholestane.

In a further preferred embodiment of the present invention,
(a) the steroid is a sterol, or
(b) the steroid is selected from the group consisting of cholesterol; a steroid hormone, preferably a gonadal steroid, more preferably an androgen, such as an anabolic steroid, androstenedione, dehydroepiandrosterone, dihydrotestosterone, or testosterone, an estrogen, such as estradiol, estriol, or estrone; a progestagen, such as progesterone or a progestine, a corticosteroid, particularly a glucocorticoid or a mineralcorticoid; an ecdysteroid such as ecdysterone; a phytosterol; a brassinosteroid; a hopanoid; and an ergosterol, more preferably the steroid is cholesterol, or
(c) the hydrophobic vitamin is α-tocopherol.

In a further preferred embodiment of the present invention, one, two, three or four, preferably one, two or three hydrophobic domains are covalently bound to the hydrophilic domain.

In a further preferred embodiment of the present invention, the two or more hydrophobic domains covalently bound to the hydrophilic domain are different or identical.

In a further preferred embodiment of the present invention, the hybrophobic domain(s) consist of a linear lipid, a steroid or a hydrophobic vitamin.

In a further preferred embodiment of the present invention, the hybrophobic domain(s) comprise, preferably consist of a linear lipid, a steroid or a hydrophobic vitamin covalently bound to a trifunctional moiety A1 via a linker moiety L2.

Such bifunctional and trifunctional moieties were successfully employed in the compounds of the invention for binding the hydrophobic moieties either directly or via a linker L2.

The linker L2 is independently any linker moiety suitable for covalently binding the hydrophobic moiety to the hydrophilic moiety, and which linker has a length of 50, 30 or 20 atoms or less between the hydrophobic moiety and A1 or A2, respectively.

In one preferred embodiment, linker L2 comprises, preferably consists of, a phosphate group, a moiety —[O—CH$_2$—CH$_2$]$_{y2}$—(SP)$_n$]$_{m1}$—, wherein SP and n are as defined above, preferably n=0, y2 is an integer from 1 to 30, preferably 3 to 10, and m1 is an integer from 1 to 10, preferably 1 to 3, a glycerol moiety, a carbamate group, an amide group, a linear alkyl group having 1 to 10 C atoms, in particular 1, 2, 3, 4, 5, 6, 7, 8, 9 or 10 atoms, and which alkyl chain contains functional groups at the terminal C-atoms, in particular independently selected from amine, carbonyl, hydroxyl, thiol, carbonic acid groups which is optionally substituted by 1, 2, 3, 4 or 5 moieties R1, wherein R1 is independently a C1-C4 alkyl, a C1-C4 hydroxyalkyl, C1-C4 aminoalkyl, a C1-C4 cyanoalkyl, a hydroxyl, a thiol, an amino or a carbonyl moiety. Examples of suitable linear alkyl groups with terminal functional groups are diaminoalkyl moieties such as H$_2$N—(CH$_2$)$_5$—NH$_2$ or hydroxylcarbonyl moieties such as —C(O)—(CH2)4-O—. Preferably, the linear alkyl group is unsubstituted. Even more preferably, the linear lipid, steroid or hydrophobic vitamin is bound to a trifunctional moiety A1 via a linker moiety —(O—CH2-CH2)j-, wherein j is selected from 1, 2, 3, 4, 5, 6, 7, 8, 9 or 10, preferably j is 3, in particular tetraethylenglycol (TEG), a phosphate moiety or a moiety comprising a TEG, glycerol, and a phosphate moiety, or a moiety comprising or consisting of -TEG-glyceryl-phosphate-O—(CH$_2$)$_4$—C(O)—.

In a more preferred embodiment, the compounds of the invention comprise a linear lipid, a steroid or a hydrophobic vitamin covalently bound to a trifunctional moiety A1 via a linker moiety L2, preferably wherein L2 is selected from the group consisting of a phosphate, amide, carbamate, an ester group and a moiety —[O—CH$_2$—CH$_2$]$_{y2}$-(SP)$_n$]$_{m1}$—, wherein SP and n are as defined above, preferably n=0,
y2 is an integer from 1 to 30, preferably 3 to 10, and
m1 is an integer from 1 to 10, preferably 1 to 3,
more preferably wherein the linear lipid, steroid or hydrophobic vitamin is bound to a trifunctional moiety A1 via the linker moiety tetraethylenglycol (TEG) or phosphate.

In a further preferred embodiment of the present invention, k1 is 1, 2 3, 4 or 5 preferably 1, 2 or 3.

In a particularly preferred embodiment of the present invention, the hydrophobic domain(s) are covalently bound to said hydrophilic domain only via the trifunctional moiety(s) A1 or via the domain X1-[A1-(L1)$_n$]$_{k1}$ described above. For such embodiments, the further preferred embodiments of the compounds of the invention also apply. In such compounds, the hydrophobic domains are exclusively localized on one terminal part of the molecule, whereas further groups like linking groups or label moieties, if present, are localized on the other terminal part, spatially separated therefrom.

In a further preferred embodiment of the present invention, k2 is 1, 2 3, 4, 5, or 6 preferably 1, 2 or 3.

In case the compound of the invention comprises a dT moiety as bifunctional moiety A2, k2 is preferably 3, 4, 5, or 6.

In another preferred embodiment of the invention, k1 is 0, and X1 is replaced by a hydrophobic domain, which preferably comprises a steroid, more preferably cholesterol. In a particularly preferred embodiment, Z is a moiety -(L3)$_{n2}$-TEG (L3)$_{n2}$-, wherein n2 is independently 0 or 1. In an even more preferred embodiment of the present invention, k2 is 1, 2 3, 4, 5, or 6 preferably 3, 4, 5 or 6. Even more preferably one or more, in particular one, further hydrophobic moiety(ies) are bound to moiety -[A2-(L1)n]k2-X2, wherein the further hydrophobic moiety(ies) comprises a steroid, more preferably cholesterol. Even more preferably, L2 is a linker moiety tetraethylenglycol (TEG), phosphate or a moiety comprising a TEG, glycerol, and phosphate moiety or a moiety comprising or consisting of -TEG-glyceryl-phosphate-O—(CH2)4-C(O)—. An exemplary compound of the invention is Chol-TEG-Chol-TEG-Doubler-Biotin-dT shown in FIG. 12.

In case a compound of the invention comprises a dT moiety as bifunctional moiety A2, k2 is preferably 3, 4, 5, or 6.

In a further preferred embodiment of the present invention, the compound further comprises a label moiety and/or a linking group.

In a further preferred embodiment of the present invention, the compound further comprises a label moiety and/or a linking group.

In a yet even further preferred embodiment of the present invention, the compound further comprises a label moiety.

Such compounds are in particular useful for cell labelling purposes. An exemplary compound of the invention is 5'-CholesterylTEG-CholesterylTEG-PEG2000-Fluos-3'.

In one such preferred embodiment, the compound does not further contain a linking group.

In another even further preferred embodiment of the present invention, the compound further comprises a linking group. An exemplary compound is 5'-CholesterylTEG-CholesterylTEG-PEG2000-BiotinTEG-3.

In one such preferred embodiment, the compound does not further contain a label moiety.

In a further even more preferred embodiment of the present invention, the compound further comprises a label moiety and a linking group.

Such compounds are in particular suitable for applications where both immobilization and detection of cells is to be achieved, e.g. for localization of immobilized cells or for quantification of cells. An example of such compound is 5'-(Cholesteryl-TEG)2-PEG2000-Fluos-Biotin_TEG-3', which was successfully used to immobilize cells to a streptavidin-coated plate and to detect these cells.

Suitable label moieties are moieties suitable for in vitro detection and are known to a skilled person. The detection may be direct, as in the case of luminescence, in particular fluorescence, or indirect in case of an enzyme or substrate thereof. Thus, both label moieties suitable for indirect or indirect detection may be employed.

"Label" or "label moiety" as used herein refers to any substance that is capable of producing a signal for direct or indirect detection. The label moiety thus may be detected directly or indirectly. For direct detection, a label moiety suitable for use in the present invention can be selected from any known detectable marker groups, like chromogens, chemiluminescent groups (e.g. acridinium esters or dioxetanes), electrochemiluminescent compounds, dyes, or fluorescent dyes (e.g. fluorescein, coumarin, rhodamine, oxazine, resorufin, cyanine and derivatives thereof), luminescent metal complexes, such as ruthenium or europium complexes and radioisotopes.

In indirect detection systems, a first partner of a bioaffine binding pair is a label moiety of the compounds of the invention; i.e. a first partner is covalently bound to and part of the compound of the invention. Examples of suitable binding pairs are hapten or antigen/antibody, biotin or biotin analogues such as aminobiotin, iminobiotin or desthiobiotin/ avidin or streptavidin, sugar/lectin, nucleic acid or nucleic acid analogue/complementary nucleic acid, and receptor/ ligand, e.g. steroid hormone receptor/steroid hormone. Preferred first binding pair members comprise hapten, antigen and hormone. Also preferred are haptens like a tag, digoxin and biotin and analogues thereof. The second partner of such binding pair, e.g. an antibody, streptavidin, etc., usually is labeled to allow for direct detection, e.g. by the label moieties as mentioned above.

Therefore, in a preferred embodiment, the label moiety is a label moiety for direct labeling, or for indirect labeling.

In one preferred embodiment, the label moiety is selected from (a) a direct labeling moiety selected from the group consisting of a chromogen, chemiluminescent group (e.g. acridinium ester or dioxetane), an electrochemiluminescent compound, a dye, a fluorescent dye (e.g. fluorescein, coumarin, rhodamine, oxazine, resorufin, cyanine and derivatives thereof), a luminescent metal complex, such as a ruthenium or europium complex, and a radioisotope; (b) or one of the partners of an indirect detection system, preferably wherein the label moiety is one of the members of the binding pairs selected from the group consisting of (i) hapten or antigen/antibody, (ii) biotin or biotin analogues such as aminobiotin, iminobiotin or desthiobiotin/avidin or streptavidin, (iii) sugar/lectin, (iv) nucleic acid or nucleic acid analogue/complementary nucleic acid, and (v) receptor or receptor fragment/ligand, e.g. steroid hormone receptor/ steroid hormone.

Preferred first binding pair members as label moieties suitable for indirect detection comprise hapten, antigen and hormone. Also preferred are haptens like digoxin and biotin and analogues thereof. The second partner of such binding pair, e.g. an antibody, streptavidin, etc., is typically labeled to allow for direct detection, e.g. by the direct label moieties as mentioned above; however, it is also possible to employ an antibody in a compound of the invention and to use a labeled antigen or hapten for detection.

In the above description of binding pair members, the term antibody is understood to encompass both antibody and antigen-binding fragments thereof.

In a preferred embodiment, the label moiety is a label moiety for direct labeling, even more preferably the label moiety is a fluorescent moiety or dye.

Suitable fluorescent moieties (or dyes) are known in the art and encompass fluorescein, Cy 3, Cy5, Cy5.5, Cy2, Cy3.5, Cy3b, Cy7, an Alexa Fluor dye, a xanthene derivative such as rhodamine, Oregon green, eosin, or Texas red, a cyanine derivative such as cyanine, indocarbocyanine, oxacarbocyanine, thiacarbocyanine, and merocyanine, a naphthalene derivative such as dansyl and prodan derivatives, a coumarin derivative, an oxadiazole derivative, such as pyridyloxazole, nitrobenzoxadiazole and benzoxadiazole, a pyrene derivatives such as cascade blue, an oxazine derivative, such as Nile red, Nile blue, cresyl violet, oxazine 170, an acridine derivatives, such as proflavin, acridine orange, acridine yellow, an arylmethine derivative, such as auramine, crystal violet, malachite green, a tetrapyrrole derivative such as porphin, phthalocyanine and bilirubin.

In the examples, fluorescein was used as representative label. This allows sensitive detection of a label, allowing both localization of a label, and/or quantification. A fluorescent label is a particularly preferred label moiety of the invention.

Suitable radioactive isotopes or radioisotopes for labeling and methods for labeling a compound of the invention with such radiolabel are known to a skilled person. For example, one of the following isotopes may be used: $^{14}C$, $^{3}H$, $^{32}P$, $^{33}P$, $^{123}I$, $^{125}I$ and $^{131}I$.

In case an antibody or antigen-binding fragments are used as members of the indirect system antibody/antigen or hapten, either an antibody or antigen-binding fragment specific for the epitope or hapten may be part of the compound of the invention, or the epitope or hapten may be part of the compound of the invention. Accordingly, the respective other member may be labeled directly, e.g. with a fluorescent label for subsequent detection. Suitable antibodies or antigen-binding fragments are described below in more detail.

In a preferred embodiment of the invention, a linking group and/or label is bound to the moiety $[A2-(L1)_n]_{k2}-X2$.

In a particularly preferred embodiment of the present invention, the hydrophobic domain(s) are covalently bound to said hydrophilic domain only via the trifunctional moiety(s) A1 (or via the domain $X1-[A1-(L1)_n]_{k1}$ described above), and a linking group and/or label moiety is bound to the moiety $[A2-(L1)_n]_{k2}-X2$. This ensures spatial separation of the hydrophobic domains for insertion into a cell membrane, and the moieties for immobilization and/or labelling.

Such compounds are in particular suitable for immobilization in case a linking group is present.

Such compounds are in particular suitable for labelling and detection in case a label moiety is present.

In a further particularly preferred embodiment of the present invention, the hydrophobic domain(s) are covalently bound to said hydrophilic domain only via the trifunctional moiety(s) A1 (or via the domain $X1-[A1-(L1)_n]_{k1}$ described above), and a linking group and label moiety is bound to the moiety $[A2-(L1)_n]_{k2}-X2$.

Such compounds further allow both immobilization and labelling, detection and quantification.

In a yet further particularly preferred embodiment of the present invention, the hydrophobic domain(s) are covalently bound to said hydrophilic domain only via the trifunctional moiety(s) A1 (or via the domain $X1-[A1-(L1)_n]_{k1}$ described above), and a linking group, but not a label moiety is bound to the moiety $[A2-(L1)_n]_{k2}-X2$.

Such compounds can be used if only immobilization or only and labelling, detection and/or quantification of cells bound is intended.

A linking group is a moiety which is suitable for reversibly or irreversibly, and/or covalently or non-covalently immobilizing a compound to a support, in particular solid support. In a preferred embodiment, the linking group is an antibody or antigen-binding antibody fragment, a receptor or a binding site thereof, a ligand to a receptor, enzyme or a binding site thereof, a substrate to an enzyme, a tag-binding site, a tag, or a functional chemical group.

A functional chemical group may be for example a thiol group which can be bound to a gold-coated substrate surface by formation of a covalent, irreversible —S—S— bond.

The binding of biotin to streptavidin or antibody or antigen-binding antibody fragment is non-covalent and reversible. Such linking groups employing non-covalent binding to a solid support are preferred in case it is intended to again detach cells for further use, e.g. for administration in a an animal model.

In a preferred embodiment, the linking group may be e.g. a biotin-moiety which allows the non-covalent attachment to a streptavidin-coated surface, or a thiol-group which can be bound to a gold-coated substrate surface as solid support.

In an even more preferred embodiment of the present invention, a compound of the invention comprises a label moiety and/or a linking group, wherein the label moiety is a fluorescent label and/or the linking group is biotin.

In an even more preferred embodiment, a compound of the invention comprises a label moiety and a linking group, wherein the label moiety is a fluorescent label and the linking group is biotin.

The term "solid support" refers to a material in the solid-phase that interacts with reagents in the liquid phase by heterogeneous reactions. The use of solid supports is well known in the fields of chemistry, biochemistry, pharmacy and molecular biology. Many types of solid supports have been developed depending on the technical problem to be solved. Any of these may be used in the context of the present invention. For example, the solid support used in the methods of the present invention may include components of silica, cellulose acetate, nitrocellulose, nylon, polyester, polyether-sulfone, polyolefin, or polyvinylidene fluoride, or combinations thereof. Further suitable solid supports include, but are not limited to, controlled pore glass, a glass plate or slide, polystyrene, and activated dextran. In other aspects, synthetic organic polymers such as polyacrylamide, polymethacrylate, and polystyrene are also illustrative support surfaces. In addition, polysaccharides such as cellulose and dextran, are further illustrative examples of support surfaces. Other support surfaces such as fibers are also operable.

The solid support may be contained in a vessel, wherein the vessel is a tube, such as a centrifuge tube or spin tube, syringes, cartridge, chamber, multiple-well plate, or test tube, or combinations thereof. The solid support may be pre-treated or functionalized in order to allow immobilization of cells. For example, a well-plate may be pre-treated with streptavidin as shown in the examples. In one embodiment, the solid support may be fibrous or particulate usually allowing for appropriate contacting. The size of the solid support suitable for use may vary. The cells may be bound to one solid support only (e.g. one vessel or multi-well plate) or may be bound to a multitude of solid supports (e.g. beads). The shape of the solid support suitable for use may be, for example, a sheet, a precut disk, cylinder, single fiber, or a solid support composed of particulates. In one preferred embodiment, the solid support is flat, or substantially flat with cavities. In one embodiment, the solid support may be fibrous or particulate. The size of the solid support may vary and may be chosen depending from the method or application to be carried out.

In some embodiments, the solid phase is a test strip, a chip, in particular a microarray or nanoarray chip, a microtiter-plate or a microparticle.

In a more preferred embodiment, a label moiety and/or linking group, where present is/are covalently bound via the trifunctional moiety A2, as described above In another embodiment, one or more moiety(s) A2 are a bifunctional or trifunctional label moiety or a linking group, more preferably a moiety A2 is a moiety comprising a nucleobase, even more preferably a moiety A2 is dT (thymidine). Such compounds comprising dT were used for determination concentration of the compound.

In a further preferred embodiment of the present invention, the linkers L1 are independently selected from the group consisting of a phosphate, amide, carbamate, and an ester group.

In a further preferred embodiment of the present invention, the moieties A1 and A2 are independently selected from a bifunctional group selected from the group consisting of a phosphate group, carbamate group, amide group, a moiety comprising a nucleobase, even more preferably dT, and a linear alkyl group having 1 to 10 C atoms and which alkyl chain contains functional groups at the terminal C-atoms, in particular independently selected from amine, carbonyl, hydroxyl, thiol, carbonic acid groups, and a trifunctional moiety having 1 to 10 C atoms and comprising at least one —OH, —SH and/or at least one —NH$_2$ group, preferably selected from lysine, serine, serinol, —O—CH$_2$—CH ((CH$_2$)$_4$—NH$_2$)—CH$_2$—, a glycerol, and a 1,3 diaminoglycerol moiety.

In a further more preferred embodiment of the present invention, the linkers L2 are independently selected from the group consisting of a phosphate, amide, carbamate, an ester group and a moiety

wherein

SP and n are as defined above, preferably n=0, y2 is an integer from 1 to 30, preferably 3 to 10, and m1 is an integer from 1 to 10, preferably 1 to 3.

PEG-based linkers, namely TEG-linkers were shown to be useful in the exemplary compounds of the invention. An exemplary compound is 5'-CholesterylTEG-CholesterylTEG-(SpacerC18)7-Fluos-BiotinTEG-3'.

Figure 6C:
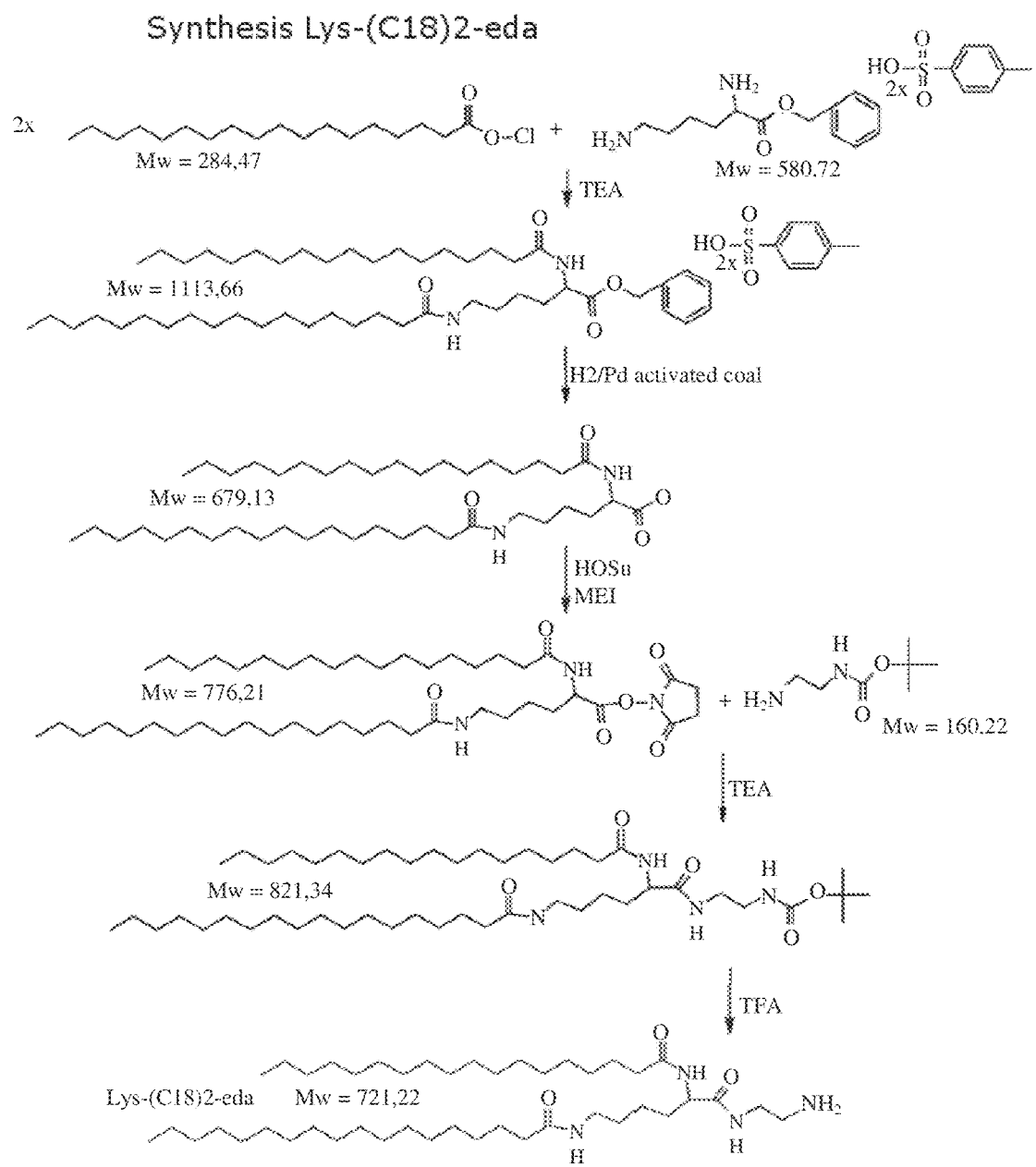
FIG. 6C: The synthesis of Biotin PEG Lys (C18) as well as side products of the synthesis.
Figure 7A:
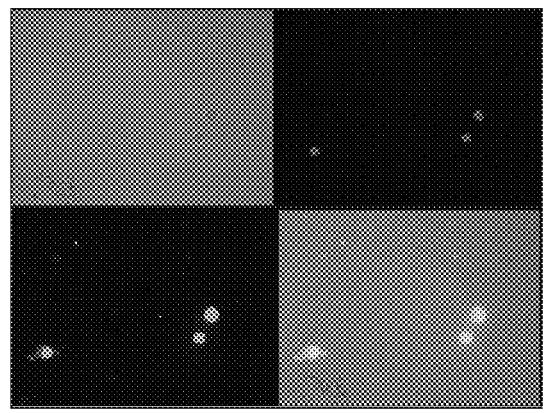
FIG. 7A: shows staining of cell with cholesteryl-containing compound with internal reference 29.891180. Representative pictures according to Example 3 throughout FIG. 7.
Figure 7B:
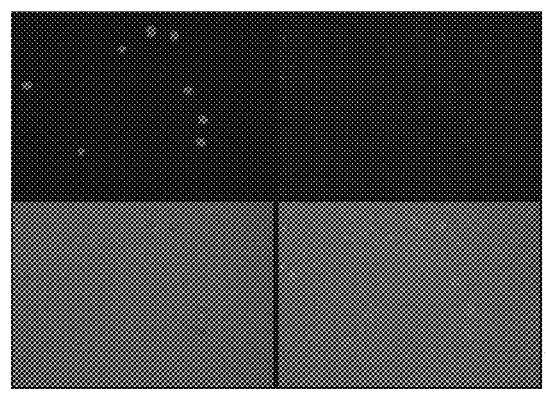
FIG. 7B: shows staining of cell with myristic acid containing compound with internal reference 29.891194.
Figure 7C:
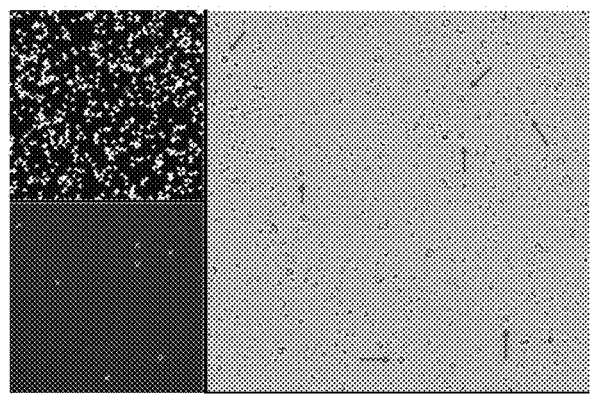
FIG. 7C: shows staining of cells with MDA-MB468.
Figure 7D:
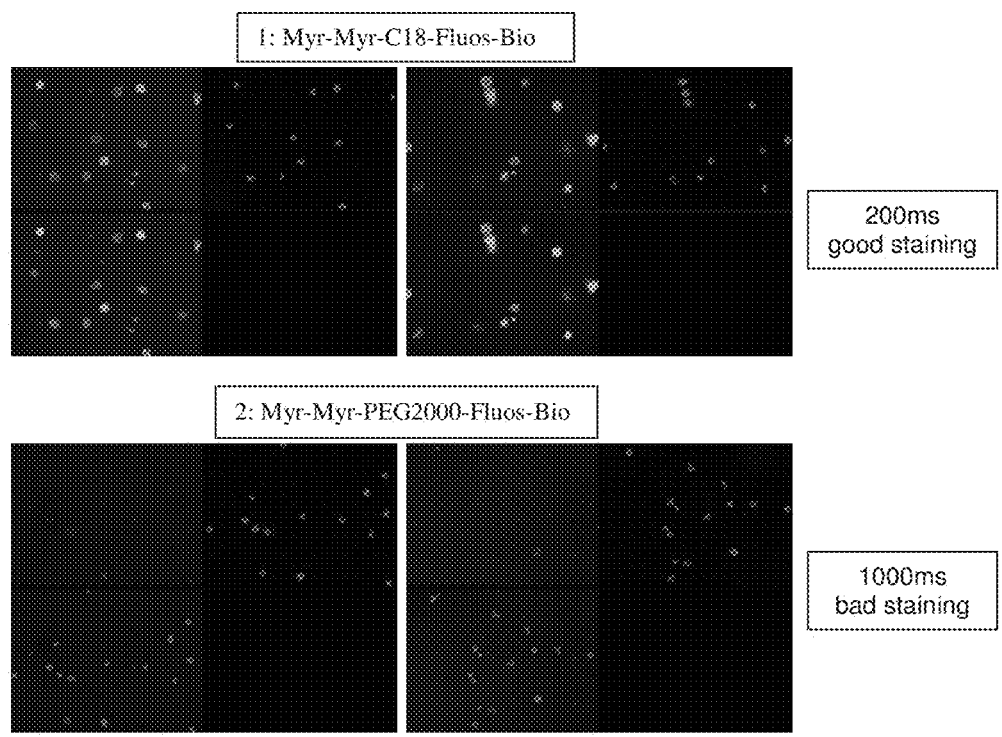
FIG. 7D: shows staining of cells staining of cells for different exposure times with different compounds indicated schematically.
Figure 7E:
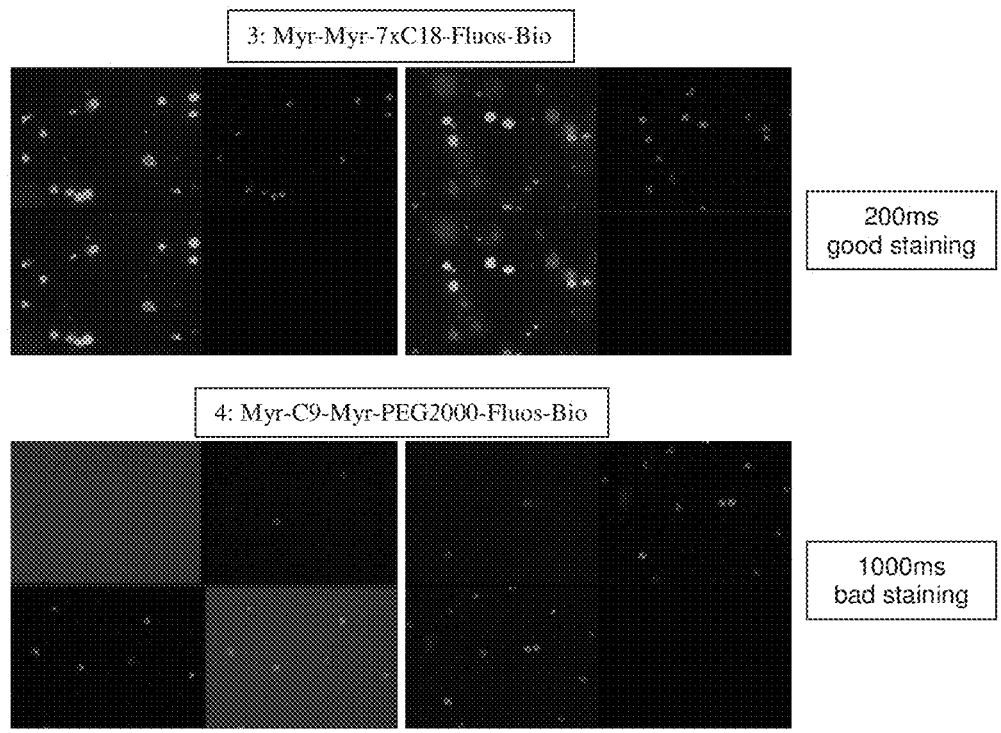
FIG. 7E: shows staining of cells staining of cells for different exposure times with different compounds indicated schematically.
Figure 8B:
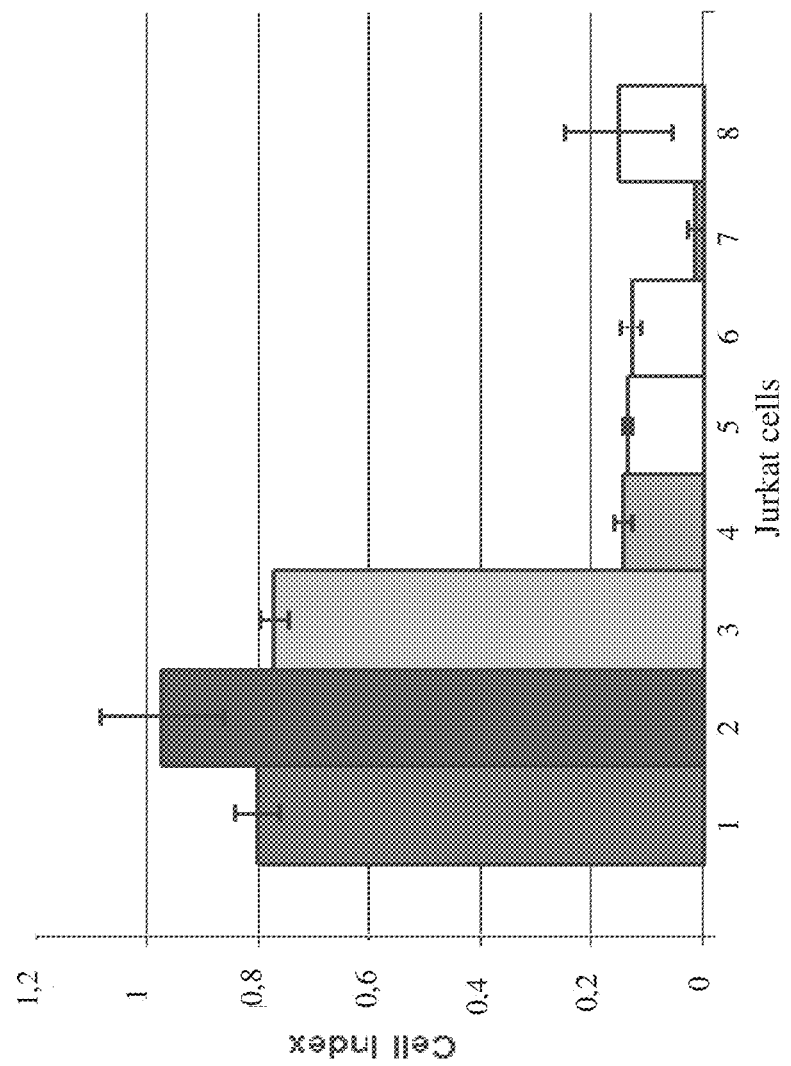
FIG. 8B: shows the results of the xCelligence experiments with Jurkat cells according to Example 3, specifically showing Jurkat cell immobilization on SA-coated plates after 3.35 hours. Column 1: PBS+ Biotin Linker; Column 2: PBS+10% FCS+ Biotin linker; Column 3: PBS+1% FCS+ Biotin linker; Column 4: PBS w/o Biotin linker; Column 5: PBS+10% FCS w/o Biotin linker; Column 6: PBS+1% FCS w/o Biotin linker; Column 7: PBS+Biotin linker w/o SA; Column 8: PBS w/o Biotin linker w/o SA.
Figure 9B:
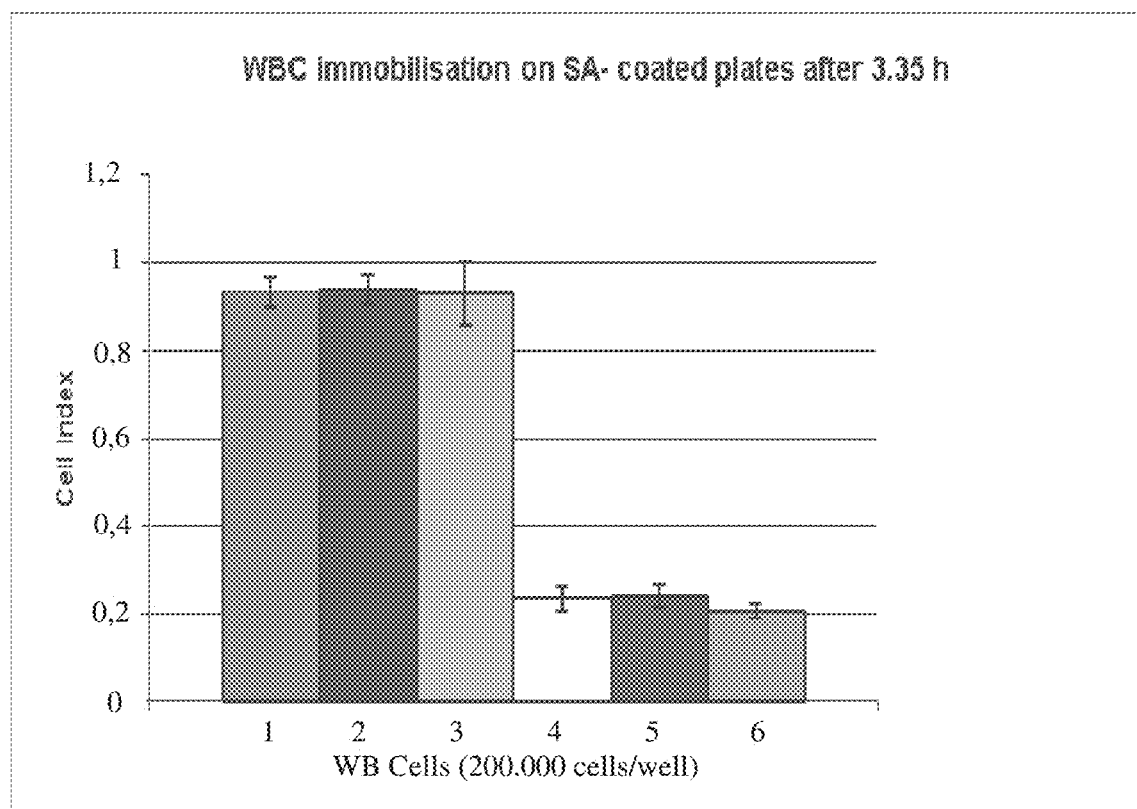
FIG. 9B: shows the results of the xCelligence experiments with WBC cells according to Example 3, speicifically showing WBC immobilization onf SA-coated plates after 3.35 hours. Column 1: PBS+ Biotin Linker; Column 2: PBS+10% FCS+ Biotin linker; Column 3: PBS+1% FCS+ Biotin linker; Column 4: PBS w/o Biotin linker; Column 5: PBS+ 10% FCS w/o Biotin linker; Column 6: PBS+1% FCS w/o Biotin linker.
Figure 11:
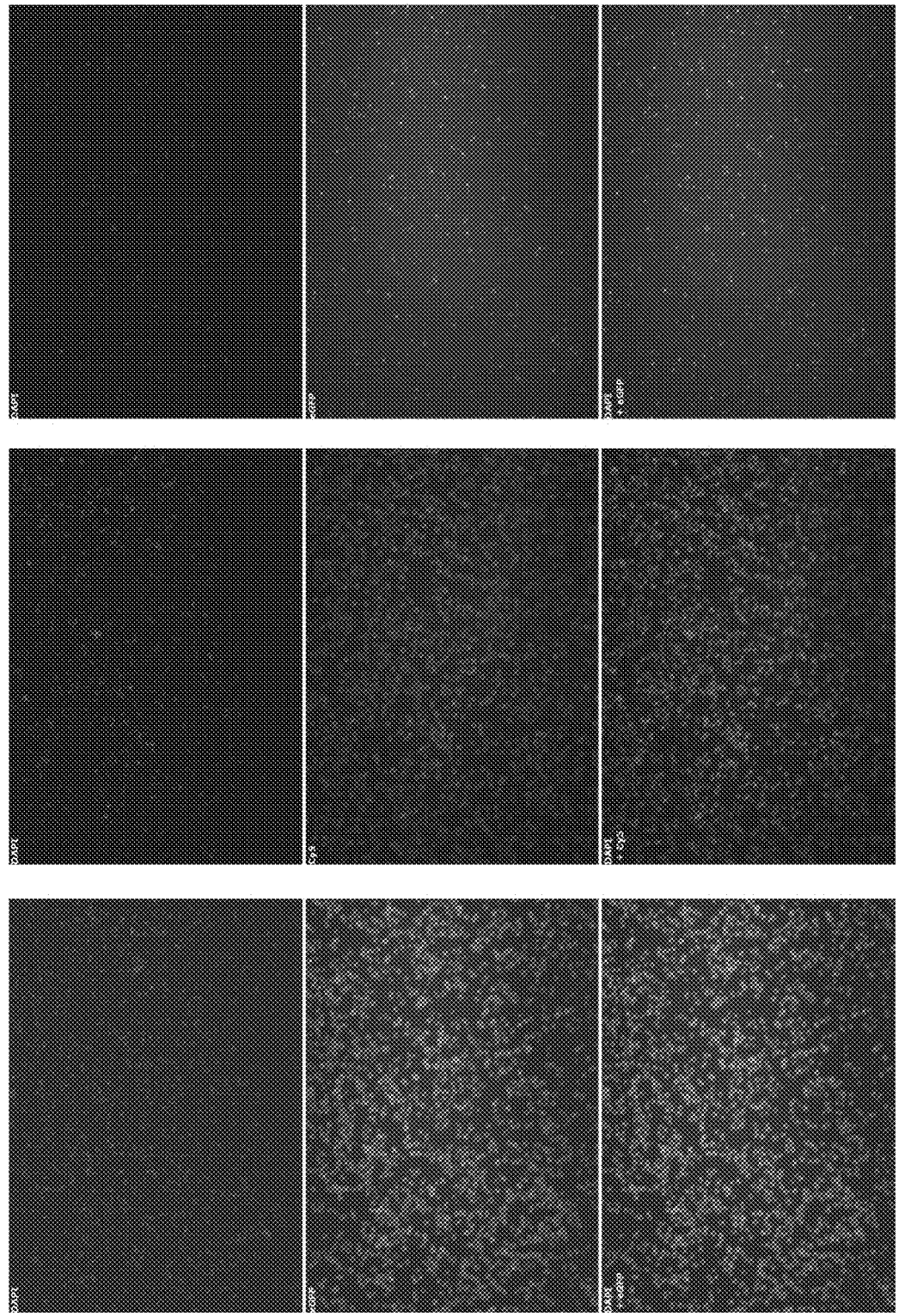
FIG. 11: shows the staining of immobilized cells, in accordance with Example 3. Left column: MDA-MB468-antibody: EpCAM Biolegend. Middle column: MDA-MB468-antibody: EpCAM Miltenys APC. Right column: WBCs-antibody: CD45 Biolegend.
Figure 13:
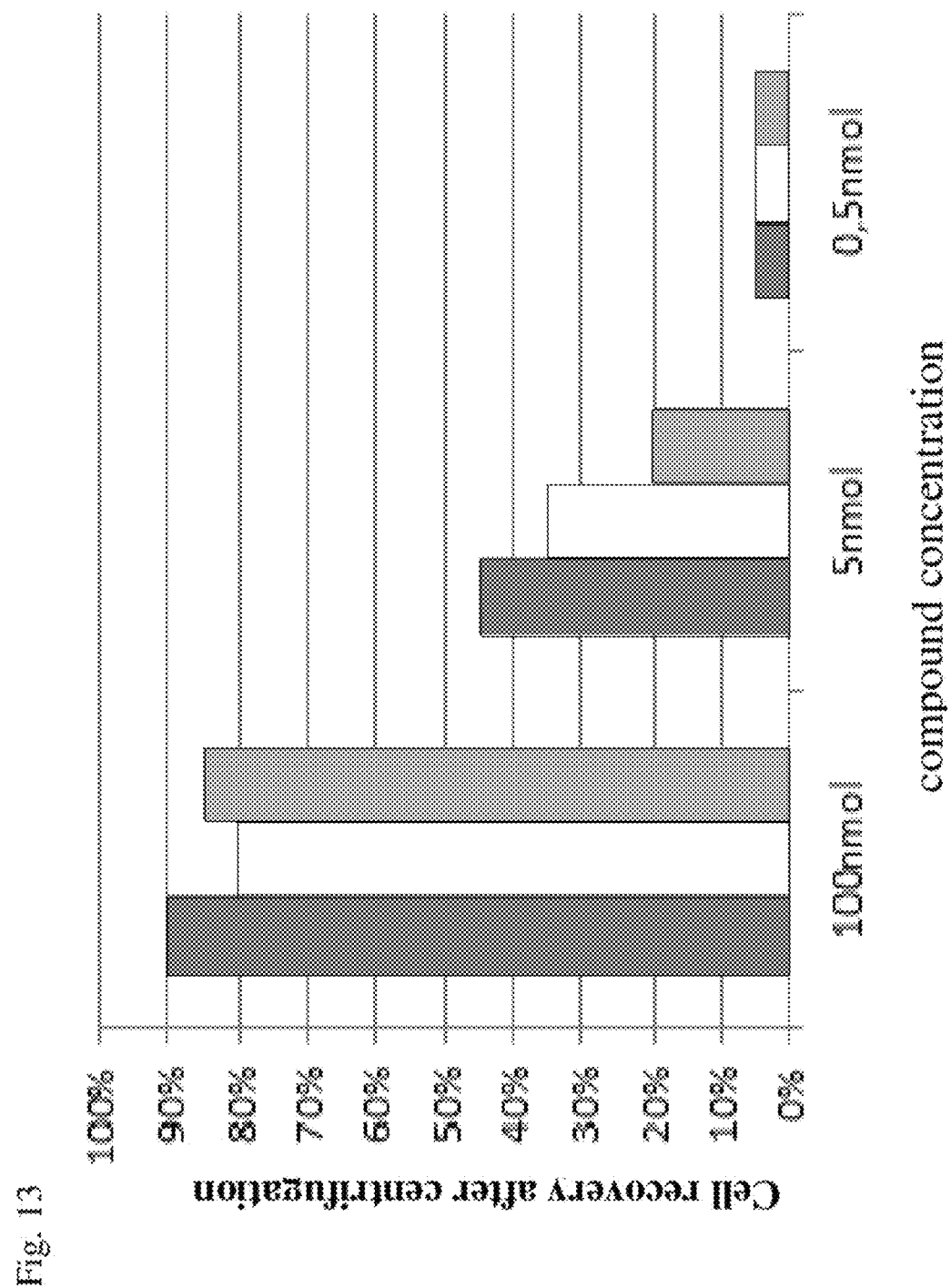
FIG. 13: shows WBC recovery rate after centrifugation and cell immobilization using different molecules. Molecule probes HH1749*, HH1750* and HH1755* (* Biotin-PEG-Lysin-(C18)2) show different performance concerning recovery rate after centrifugation: The higher the concentration of the molecule, the higher the cell recovery rate after centrifugation. Centrifugation characteristics: 10 min, 300×g.

The compounds of the invention as well as the intermediates thereof can be prepared by methods known to a skilled person. An exemplary synthesis of a compound of the invention is shown in FIG. 6C. Also, intermediates used in the synthesis of compounds of the invention are shown in FIG. 12. Further, the general concept of the syntheses is shortly described in Example 1 for the compounds. The compounds can be prepared on solid phase analogous to the phosphoramidite-based synthesis of nucleotides. The compounds may be synthesized by synthesis on a solid support like CPG as described in the Examples. In particular, the compounds may be synthesized by subsequent coupling steps under conditions known to a skilled person, and cleavage from the solid support (in the examples: CPG (controlled pore glass)). Also other solid supports such as macroporous polystyrene may be used for synthesis. The synthesis may be performed by retaining a protecting group or by cleaving of the protecting group. In particular, the compounds may be synthesized in either DMT on or DMT off modus, leaving the DMT molecule on the end of the molecule designated as 3' end, or by cleaving off the DMT group. The compounds are optionally further purified e.g. by dialysis.

The synthesis of Biotin-PEG-Lys-(C18)2 is described in detail in FIG. 6 C).

The other compounds of the invention can be prepared in an analogous manner according to methods known in the art.

In a yet further embodiment the present invention relates to a composition comprising at least one compound of the invention bound to at least one cell, preferably a viable cell. Such composition provides for a stabilized cell. Depending on the further presence of a label moiety and/or linking group, the composition is useful for detection and/or immobilization of the cell, respectively.

In one preferred embodiment, such composition further comprises a solid support, to which at least one compound of the invention is bound via a linking group. In such embodiment, at least one cell is immobilized to a solid support via a compound of the invention. In case the compound further contains a label moiety, localization, detection and quantification of the cell(s) is possible.

In another preferred embodiment, a composition comprising at least one compound of the invention bound to at least one cell comprises an aqueous, buffered solution, wherein at least one cell to which at least one compound of the invention is bound, is suspended. Such composition are suitable for adequately stabilizing the cells therein, e.g. during FACS or centrifugation.

The compounds are suitable for binding to any cells which contain a lipid bilayer. Preferably, the cells are eukaryotic cells, more preferably animal, even more preferably vertebrate cells, most preferably human cells.

In a further preferred embodiment, the cell is a white blood cell, a rare cell, a tumor cell or a mutated cell, more preferably a vertebrate or human white blood cell, rare cell, tumor cell or mutated cell.

In a further embodiment the present invention relates to a composition comprising one or more compounds of the invention.

It could be shown that some compositions comprising two or more different compounds of the invention are in particular useful for cell-type-independent labeling, as shown in the examples.

Therefore, in another embodiment, the present invention relates to a composition comprising at least three different compounds of the invention, wherein the different compounds differ at least in their hydrophobic domains and wherein the different compounds comprise a label moiety.

By using a variety of compounds of the inventions of which at least two differ at least in their hydrophobic domain(s), a composition can be obtained which labels all cell types, thereby providing a cell-type independent labelling.

In an even more preferred embodiment, the composition thus comprises at least four, five, six, seven, eight, nine or ten different compounds of the invention. In an even more preferred embodiment, two, three, four, five, six, seven, eight, nine, ten or all compounds of such composition differ at least in their hydrophobic domains.

Preferred hydrophobic domains which are suitable are those as defined above. For example, a composition comprising 5'-CholesterylTEG-CholesterylTEG-PEG2000-Fluos-3' can be used for cell labelling, as this compound exhibits excellent labelling properties (see Example 2).

Accordingly, 5'-CholesterylTEG-CholesterylTEG-PEG2000-Fluos-3' is in a preferred embodiment one of at least three different labeled compounds of the invention.

In a more preferred embodiment, a hydrophobic domain of at least one compound comprises, preferably consists of, a saturated fatty acid, especially myristic acid, stearic acid or behenic acid, particularly myristic acid, and/or a hydrophobic domain of at least one compound comprises, preferably consists of, a steroid, in particular cholesterol, or a hydrophobic vitamin, in particular α-tocopherol.

In preferred embodiment, the present invention relates to an aqueous solution comprising one or more compounds of the invention.

The aqueous solution of the invention is preferably buffered. For example a solution of the invention may be a phosphate buffered saline solution (PBS), Tris, and/or Hepes-buffered solution.

The pH of the solution of the invention is preferably about 5.5 to 8.5, more preferably 6.5 to 7.5.

In yet further embodiment, the present invention relates to a kit comprising at least one compound or composition of the present invention.

The kit may further comprise two or more compounds of the invention stored separately, e.g. in a vessel or syringe. They may be stored in dry form, e.g. freeze-dried or dried, or as solution, or in frozen form, e.g. as frozen solution.

In one embodiment, the compounds of the inventions can be used for detection and/or characterization of rare cells, preferably for one rare cell characterization.

In such use, nucleated cells isolated from whole blood can be immobilized on a defined surface using the compounds of the invention on an array, in particular microarray or nanoarray. Rare cells within this population of nucleated cells, for example within a population of white blood cells (WBCs) e.g. circulating tumor cells, endothelial cells, or epithelial cells, can be quantitatively bound to this surface and identified via an antibody or specific binding molecule against an antigen or biochemical property specific for the rare cell population. This enables the exact localization and re-localization for further characterization steps if required.

Therefore, the present invention also relates to the use of a compound, or a composition comprising one or more compounds of the invention for one rare cell characterization.

In a further embodiment, the compounds of the invention can be used for immobilization of suspension cells, e.g. for screening purposes like for antibody screening.

Therefore, the present invention also relates to the use of a compound, or a composition comprising one or more compounds, of the invention for immobilization of suspension cells, preferably for screening, even more preferably for screening with antibodies or antigen-binding antibody fragments or binding molecules of other formats.

Screening of antibodies or antigen-binding fragments thereof on culture cell lines is a general application in antibody development. One application comprises the binding of the antibody to a specific receptor molecule on the cell surface. Using a secondary antibody (sandwich effect) binding characteristics of the first antibody can be investigated. Using suspension cells it is difficult to perform such experiments. The developed compounds useful for cell immobilization allow the careful immobilization of suspension cells without loosing any physiological cell properties and can be therefore used to perform such screening assays.

Also, suspension cells can be immobilized for functional cell assays using the compounds of the invention. Assays studying cellular function in vitro or in vivo are of importance: Functional cellular assays are generally used in pharmaceutical, agrochemical and biotechnological research and development to investigate small molecule compounds or biologicals or to identify classes of small molecules in high throughput screening. Some functional assays are based on surface-dependent assays and are therefore generally performed with adherent cells. The compounds of the invention can be used for immobilization of suspension cells to apply such functional assays.

Therefore, the present invention also relates to the use of a compound, or a composition comprising one or more compounds of the invention, for performing functional cellular assays.

In one preferred embodiment, the uses of the invention are in vitro uses of the compounds of the invention.

Moreover, compounds of the invention are in particular useful for the binding of living cells to a solid surface, followed by detachment off the surface and implantation into mouse models. These kinds of functional assays are of major importance, e.g. for studying the tumor-inducing potential of circulating abnormal cells.

Therefore, the present invention also relates to the use of a compound, or a composition comprising one or more compounds of the invention binding living cells to a solid surface and subsequent detachment.

Also, the compounds of the invention are useful for a lab on a chip and can be used for a lab on a chip: To investigate cell morphology or cell function of few cells like 2 to 50 cells, or single cells, a surface can be selectively and systematically spotted with a compound of the invention. This spotting allows a targeted immobilization of few cells or single cells on such spot. This allows molecular analysis directly on the surface (chip).

Therefore, the present invention also relates to the use of a compound, or a composition comprising one or more compounds of the invention for a lab on a chip. The chip may be an array, in particular microarray or nanoarray.

In a further embodiment, the present invention relates to solid substrate comprising a compound of the invention bound to solid substrate.

Such solid substrate may be a particle like a nanoparticle, in particular magnetic nanoparticle, a column, or a flat substrate, an array or a well plate, in particular oligo- or multi-well plate.

In a further embodiment of the present invention relates to an array comprising a compound of the invention bound to the array.

In a preferred embodiment, the array is a microarray or nanoarray.

The compounds of the invention are moreover useful for cell stabilization during centrifugation processes.

Therefore, the present invention also relates to the use of a compound, or a composition comprising one or more compounds of the invention for stabilizing at least one cell, in particular during centrifugation.

Typically, the compounds of the invention are added for example as aqueous solution to a cell suspension of interest. Typically, mixing is performed gently in order to maintain viability of the cells.

Such centrifugation steps are employed for example for separation of cells from surrounding liquids like media. Cells have to be centrifugated and therefore are exposed to shear stress. Very sensitive and fragile cell populations can be damaged by such processes. The compounds of the invention improve the handling of such cell populations.

The compounds of the invention are moreover useful for cell stabilization in biotechnology, for example in large scale animal cell cultivation: it has been published that shear sensitivity of mammalian cells can be a relevant problem which can complicate the development of large scale animal cell cultivation. The compounds of the invention reduce these problems.

Therefore, the present invention also relates to the use of a compound, or a composition comprising one or more compounds of the invention for stabilizing cells in large scale animal cell cultivation.

The compounds of the invention are moreover useful for cell stabilization in flow cytometry and/or fluorescence activated cell sorting:

Flow cytometry is a very commonly used method to separate specific cell population. Within this process, cells are exposed to high shear stresses dependent on the flow speed. The compounds of the invention reduce this shear stress.

Therefore, the present invention also relates to the use of a compound, or a composition comprising one or more compounds of the invention for stabilizing cells in flow cytometry and/or fluorescence activated cell sorting.

The compounds of the invention are moreover useful for cell stabilization in bead-based cell separation processes:

Cell populations with a distinct phenotype can be separated by specific antibodies coupled to magnetic beads. Within this process cells are exposed to high shear stresses dependent on the bead size. The compounds of the invention reduce this shear stress.

Therefore, the present invention also relates to the use of a compound, or a composition comprising one or more compounds of the invention for stabilizing cells in bead-based cell separation processes.

In a further embodiment, the present invention relates to a method of labeling a cell, the method comprising:
 a) providing a compound of the invention, wherein the compound comprises a label moiety; and
 b) contacting a cell with the compound under conditions allowing the interaction of the compound with the membrane of the cell, thereby immobilizing the label on the cell; and
 c) optionally detecting the label.

As shown in the examples, a compound of the invention, wherein the compound comprises a label moiety, is contacted with a cell. As labelling is preferably done with viable or potentially viable cells, the cells are typically present in an aqueous solution, which is preferably buffered and/or contains nutrients, e.g. the cells are suspended in PBS. The labeled compound of the invention may be added to the cells, e.g. in form of a solution, e.g. as aqueous solution by methods known in the art, as pipetting.

Typically, the contacting takes place at a temperature of about 1° C. to 45° C., preferably, 10° C. to 30° C., more preferably 22° to 38° C.

Also, the contacting takes place at a pressure of about 900 to 1100 mbar in order to maintain cell viability.

Also, the cells are preferably incubated with the compounds for a sufficient time to allow for binding. Typically, the cells are preferably incubated with the compounds for 1 minute to 3 days, preferably 5 minutes to 24 h, even more preferably for 10 minutes to 8 hours.

Moreover, the aqueous solution is typically chosen not to affect the integrity and/or viability of a cell.

Such conditions allow the interaction of the compound with the membrane of the cell. Thereby the label moiety is immobilized on the cell.

The label moiety, and thereby the cell, can be detected as described above, depending on the label moiety chosen. In case of a direct label, the detection can take place directly, e.g. by detecting the fluorescence of fluorescein or absorption of dT, as shown in the examples.

In case of indirect detection systems, the second member of a binding pair may be detected. For example, a biotin labeled compound of the invention may be used. For detection, streptavidin, which in turn is labeled with a directly detectable label, may be used. Therefore, biotin may represent a linking group or a label moiety of the invention, depending on the further steps.

For cell-independent labeling, certain compositions of the inventions described above may be used.

The invention further relates in one embodiment to a method of labeling a cell, the method comprising
  a) providing composition comprising at least three different compounds of the invention, wherein the different compounds differ at least in their hydrophobic domains and wherein the different compounds comprise a label moiety,
  b) contacting a cell with the composition under conditions allowing the interaction of the compound with the membrane of the cell, thereby labeling the cell, and
  c) optionally detecting the label.

Such compositions allow for cell-independent labeling as described above in more detail, by the employment of different hydrophobic groups.

For this method of the invention, the same embodiments apply as for above described method of labeling a cell using compounds of the invention.

The composition is therefore preferably solution, more preferably aqueous solution comprising the compounds of the invention.

In a preferred embodiment, the cell is a cell in suspension or an adherent cell and/or the cell is an animal or human cell, particularly a vertebrate cell, especially a mammalian cell or human cell.

In a further embodiment, the present invention relates to a method of immobilizing a linking group on the surface of a cell, the method comprising
  a) providing a compound of the invention, wherein the compound comprises a linking group; and
  b) contacting a cell with the compound under conditions allowing the interaction of the compound with the membrane of the cell, thereby immobilizing the linking group.

For steps a) and b), the same embodiments apply as for the labeling of cells described above, with the exception that in this embodiment the compound comprises a linking group.

In a yet further embodiment, the present invention relates to the use of compound of the invention, wherein the compound comprises a label moiety, for the labeling of a cell.

In a yet further embodiment, the present invention relates to the use of compound of the invention, wherein the compound comprises a linking group, for immobilization of a linking group on the surface of the cell.

In a preferred embodiment, the cell is a cell in suspension or an adherent cell and/or the cell is an animal or human cell, particularly a vertebrate cell, especially a mammalian cell.

Regarding the antibodies and antigen-binding antibody fragments, skilled person is aware of such molecules: Naturally occurring antibodies are globular plasma proteins (~150 kDa (http://en.wikipedia.org/wiki/Dalton_unit)) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM. In the present invention, examples of suitable formats include the format of naturally occurring antibodies including antibody isotypes known as IgA, IgD, IgE, IgG and IgM.

In addition to naturally occurring antibodies, artificial antibody formats including antibody fragments have been developed. Some of them are described in the following.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

Accordingly, the term "antibody", as used herein, means any polypeptide which has structural similarity to a naturally occurring antibody and is capable of specific binding to the respective target, wherein the binding specificity is determined by the CDRs. Hence, "antibody" is intended to relate to an immunoglobulin-derived structure with binding to the respective target including, but not limited to, a full length or whole antibody, an antigen binding fragment (a fragment derived, physically or conceptually, from an antibody structure), a derivative of any of the foregoing, a chimeric molecule, a fusion of any of the foregoing with another polypeptide, or any alternative structure/composition which selectively binds to the respective target. The antibody or functionally active parts thereof may be any polypeptide which comprises at least one antigen binding fragment. Antigen binding fragments consist of at least the variable domain of the heavy chain and the variable domain of the light chain, arranged in a manner that both domains together are able to bind to the specific antigen.

"Full length" or "complete" antibodies refer to proteins that comprise two heavy (H) and two light (L) chains inter-connected by disulfide bonds which comprise: (1) in terms of the heavy chains, a variable region and a heavy chain constant region which comprises three domains, CH1, CH2 and CH3; and (2) in terms of the light chains, a light chain variable region and a light chain constant region which comprises one domain, CL.

"Antigen-binding antibody fragments" or "Antigen-binding fragments thereof" also contain at least one antigen binding fragment as defined above, and exhibit essentially the same function and binding specificity as the complete antibody of which the functionally active part (or fragment) is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Variable domains (Fvs) are the smallest fragments with an intact antigen-binding domain consisting of one VL and one VH. Such fragments, with only the binding domains, can be generated by enzymatic approaches or expression of the relevant gene fragments, e.g. in bacterial and eukaryotic cells. Different approaches can be used, e.g. either the Fv fragment alone or 'Fab'-fragments comprising one of the upper arms of the "Y" that includes the Fv plus the first constant domains. These fragments are usually stabilized by introducing a polypeptide link between the two chains which results in the production of a single chain Fv (scFv). Alternatively, disulfide-linked Fv (dsFv) fragments may be used. The binding domains of fragments can be combined with any constant domain in order to produce full length antibodies or can be fused with other proteins and polypeptides.

A recombinant antibody fragment is the single-chain Fv (scFv) fragment. Dissociation of scFvs results in monomeric scFvs, which can be complexed into dimers (diabodies), trimers (triabodies) or larger aggregates such as TandAbs and Flexibodies.

Antibodies with two binding domains can be created either through the binding of two scFv with a simple polypeptide link (scFv)2 or through the dimerization of two monomers (diabodies). The simplest designs are diabodies that have two functional antigen-binding domains that can be either the same, similar (bivalent diabodies) or have specificity for distinct antigens (bispecific diabodies).

Also, antibody formats comprising four variable domains of heavy chains and four variable domains of light chains have been developed. Examples of these include tetravalent bispecific antibodies (TandAbs and Flexibodies, Affimed Therapeutics AG, Heidelberg. Germany). Flexibodies are a combination of scFv with a diabody multimer motif resulting in a multivalent molecule with a high degree of flexibility for joining two molecules which are quite distant from each other on the cell surface. If more than two functional antigen-binding domains are present and if they have specificity for distinct antigens, the antibody is multi-specific.

In summary, specific immunoglobulin types which represent antibodies or antigen-binding fragments thereof include but are not limited to the following antibody: a Fab (monovalent fragment with variable light (VL), variable heavy (VH), constant light (CL) and constant heavy 1 (CHI) domains), a F(ab')2 (bivalent fragment comprising two Fab fragments linked by a disulfide bridge or alternative at the hinge region), a Fv (VL and VH domains), a scFv (a single chain Fv where VL and VH are joined by a linker, e.g., a peptide linker), a bispecific antibody molecule (an antibody molecule with specificity as described herein linked to a second functional moiety having a different binding specificity than the antibody, including, without limitation, another peptide or protein such as an antibody, or receptor ligand), a bispecific single chain Fv dimer, a diabody, a triabody, a tetrabody, a minibody (a scFv joined to a CH3).

The antibody may be a monoclonal antibody, a chimeric antibody or a humanised antibody.

A tag is a peptide motif used for recognition in biotechnology. A well-known tag is the His-tag (6× Histidine) which can be bound to a $Ni^{2+}$-column.

In case a nucleic acid or nucleic acid analogue/complementary nucleic acid is used as binding pair, any nucleic acid sequence and its complementary sequence may be used.

The lectins are carbohydrate-binding proteins that are highly specific for sugar moieties. As a suitable lectin, Concanavalin A may be used which binds to α-D-mannosyl and α-D-glucosyl residues, branched α-mannosidic structures (high α-mannose type, or hybrid type and biantennary complex type N-Glycans.

As receptor/ligand binding pair, e.g. steroid hormone receptor/steroid hormone may be used. For example, estrogen may be used as steroid, and a receptor thereof as respective binding partner.

Example 1: Synthesis of Compounds of the Invention

The following compounds of the invention were synthesized:

| Internal No. | Scale | chemical structure (modular) | Yield |
|---|---|---|---|
| BMO 29.891131 | 10 µMol Scale | 5'-alphaTocopherolTEG-PEG2000-Fluos-3' | 58 pMol/µL-234 nMol |
| DMTrON-Synthesis/all 20 min. Coupling/Standard-CPG-Cleavage/DMTrOFF/Dialysis/no Purification/Crude product/Fluos-Conc. | | | |
| BMO 29.891132 | 10 µMol Scale | 5'-Cholesteryl-TEG-PEG2000-Fluos-3' | 61 pMol/µL-216 nMol |
| DMTrON-Synthesis/all 20 min. Coupling/Standard-CPG-Cleavage/DMTrOFF/Dialysis/no Purification/Crude product/Fluos-Conc. | | | |
| BMO 29.891133 | 10 µMol Scale | 5'-CholesterylTEG-CholesterylTEG-PEG2000-Fluos-3' | 43 pMol/µL-153 nMol |
| DMTrON-Synthesis/all 20 min. Coupling/Standard-CPG-Cleavage/DMTrOFF/Dialysis/no Purification/Crude product/Fluos-Conc. | | | |
| BMO 29.891137 | 10 µMol Scale | 5'-CholesterylTEG-CholesterylTEG-PEG2000-BiotinTEG-3' | 111 pMol/µL-200 nMol |
| DMTrOFF-Synthesis/all 20 min. Coupling/Standard-CPG-Cleavage/Dialysis/no Purification/Crude product/Conc. estimated | | | |
| BMO 29.891180 | 10 µMol Scale | 5'-CholesterylTEG-CholesterylTEG-PEG2000-Fluos-BiotinTEG-3' | 3577 pMol/µL-6440 nMol |
| DMTrOFF-Synthesis/all 20 min. Coupling/Standard-CPG-Cleavage/Dialysis/no Purification/Crude product/Fluos-Conc. | | | |
| BMO 29.891194_Ch01 | 1 µMol Scale | 5'-Myristic acid-Myristic acid-PEG2000-Fluos-BiotinTEG-3' | 10 pMol/µL-12 nMol |
| DMTrON-Synthesis/Coupling: 1 + 2 = 10 min-3 = 2 × 8 min-4 + 5 = 10 min/Standard-CPG-Cleavage/C18-Purification/DMTrOFF/Dialysis/F30-39-TEA+/Fluos-Conc. | | | |
| BMO 29.891194_Ch02 | 1 µMol Scale | 5'-Myristic acid-Myristic acid-PEG2000-Fluos-BiotinTEG-3' | 22 pMol/µL-24 nMol |
| DMTrON-Synthesis/Coupling: 1 + 2 = 10 min-3 = 2 × 8 min-4 + 5 = 15 min/Standard-CPG-Cleavage/C18-Purification/F89-98-TEA+/evaporate/DMTrOFF/Fluos-Conc. | | | |
| BMO 29.891194_Ch03 | 1 µMol Scale | 5'-Myristic acid-Myristic acid-PEG2000-Fluos-BiotinTEG-3' | 11 pMol/µL-11 nMol |
| DMTrON-Synthesis/all 20 min. Coupling/Standard-CPG-Cleavage/C18-Purification/F69-79-TEA+/evaporate/DMTrOFF/Fluos-Conc. | | | |
| BMO 29.891197 | 1 µMol Scale | 5'-Myristic acid-SpacerC9-Myristic acid-PEG2000-Fluos-BiotinTEG-3' | 0.5 pMol/µL-0.7 nMol |

-continued

| Internal No. | Scale | chemical structure (modular) | Yield |
|---|---|---|---|
| DMTrON-Synthesis/all 20 min. Coupling/Standard-CPG-Cleavage/C18-Purification/F67-72-TEA+/evaporate/DMTrOFF/Fluos-Conc. | | | |
| BMO 29.89121 3__Ch01 | 10 μMol Scale | 5'-Myristic acid-Myristic acid-SpacerC18-Fluos-BiotinTEG-3' | 538 pMol/μL-808 nMol |
| DMTrON-Synthesis/all 20 min. Coupling/Standad-CPG-Cleavage/T1-C18-Purification/T1 = F40-44-TEA+/evaporate/Fluos-Conc. | | | |
| BMO 29.891213_Ch02 | | 5'-Myristic acid-Myristic acid-SpacerC18-Fluos-BiotinTEG-3' | 613 pMol/μL-919 nMol |
| T2-C18-Purification/T2 = F73-99-TEA+/evaporate/DMTrOFF/Fluos-Conc. | | | |
| BMO 29.891214 | 1 μMol Scale | 5'-Myristic acid-Myristic acid-(SpacerC18)7-Fluos-BiotinTEG-3' | 100 pMol/μL-100 nMol |
| DMTrON-Synthesis/all 10 min. Coupling/Standard-CPG-Cleavage/C18-Purification/F49-53-TEA+/evaporate/DMTrOFF/Fluos-Conc. | | | |
| BMO 29.891218 | 1 μMol Scale | 5'-Myristic acid-SpacerC9-Myristic acid-(SpacerC18)7-Fluos-BiotinTEG-3' | 40 pMol/μL-44 nMol |
| DMTrON-Synthesis/Coupling: 1 + 2 = 20 min-3-9 = 5 min-10-12 = 20 min/Standard-CPG-Cleavage/C18-Purification/F30-35-TEA+/evaporate/DMTrOFF/Fluos-Conc. | | | |
| BMO 29.891219 | 1 μMol Scale | 5'-Myristic acid-SpacerC12-Myristic acid-(SpacerC18)7-Fluos-BiotinTEG-3' | 15 pMol/μL-22 nMol |
| DMTrON-Synthesis/Coupling: 1 + 2 = 20 min-3-9 = 5 min-10-12 = 20 min/Standard-CPG-Cleavage/C18-Purification/F28-32-TEA+/evaporate/DMTrOFF/Fluos-Conc. | | | |
| BMO 29.891220 | 1 μMol Scale | 5'-Myristic acid-SpacerC18-Myristic acid-(SpacerC18)7-Fluos-BiotinTEG-3' | 56 pMol/μL-79 nMol |
| DMTrON-Synthesis/Coupling: 1 + 2 = 20 min-3-9 = 5 min-10-12 = 20 min/Standard-CPG-Cleavage/C18-Purification/F34-38-TEA+/evaporate/DMTrOFF/Fluos-Conc. | | | |
| BMO 29.891221 | 1 μMol Scale | 5'-Myristic acid-Myristic acid-Myristic acid-(SpacerC18)7-Fluos-BiotinTEG-3' | 38 pMol/μL-42 nMol |
| DMTrON-Synthesis/Coupling: 1 + 2 = 20 min-3-9 = 5 min-10-12 = 20 min/Standard-CPG-Cleavage/C18-Purification/F32-41-TEA+/evaporate/DMTrOFF/Fluos-Conc. | | | |
| BMO 29.891222__Ch03 | 1 μMol Scale | 5'-CholesterylTEG-CholesterylTEG-(SpacerC18)7-Fluos-BiotinTEG-3' | 12 pMol/μL-14 nMol |
| DMTrON-Synthesis/Coupling: 1 + 2 = 2 × 10 min-3-9 = 5 min-10-12 = 2 × 10 min/Standard-CPG-Cleavage/C8-Purification/F69-73-TEA+/evaporate/DMTrOFF/Fluos-Conc. | | | |
| BMO 29.891222__Ch04 | 1 μMol Scale | 5'-CholesterylTEG-CholesterylTEG-(SpacerC18)7-Fluos-BiotinTEG-3' | 6 pMol/μL-7 nMol |
| DMTrON-Synthesis/Coupling: 1 + 2 = 2 × 15 min-3-9 = 5 min-10-12 = 2 × 15 min/Standard-CPG-Cleavage/C4-Purification/F10-13-TEA+/evaporate/DMTrOFF/Fluos-Conc. | | | |
| BMO 29.891222__Ch05 | 1 μMol Scale | 5'-CholesterylTEG-CholesterylTEG-(SpacerC18)7-Fluos-BiotinTEG-3' | 13 pMol/μL-17 nMol |
| DMTrOFF-Synthesis/Coupling: 1 + 2 = 2 × 15 min-3-9 = 5 min-10-12 = 2 × 15 min/Standard-CPG-Cleavage/C4-Purification/F60-64-TEA+/evaporate/Fluos-Conc. | | | |
| BMO 29.891224 | 1 μMol Scale | 5'-CholesterylTEG-SpacerC12-CholesterylTEG-(SpacerC18)7-Fluos-BiotinTEG-3' | 74 pMol/μL-81 nMol |
| DMTrON-Synthesis/Coupling: 1 + 2 = 20 min-3-9 = 5 min-10-12 = 20 min/Standard-CPG-Cleavage/C18-Purification/F26-33-TEA+/evaporate/DMTrOFF/Fluos-Conc. | | | |
| BMO 29.891225 | 1 μMol Scale | 5'-CholesterylTEG-SpacerC18-CholesterylTEG-(SpacerC18)7-Fluos-BiotinTEG-3' | 5 pMol/μL-6 nMol |
| DMTrON-Synthesis/Coupling: 1 + 2 = 20 min-3-9 = 5 min-10-12 = 20 min/Standard-CPG-Cleavage/C18-Purification/F14-19-TEA+/evaporate/DMTrOFF/Fluos-Conc. | | | |
| BMO 29.891227 | 1 μMol Scale | 5'-Myristic acid-CholesterylTEG-(SpacerC18)7-Fluos-BiotinTEG-3' | 20 pMol/μL-21 nMol |
| DMTrON-Synthesis/Coupling: 1 + 2 = 20 min-3-9 = 5 min-10-12 = 20 min/Standard-CPG-Cleavage/C18-Purification/F34-40-TEA+/evaporate/DMTrOFF/Fluos-Conc. | | | |
| BMO 29.891228__Ch02 | 1 μMol Scale | 5'-CholesterylTEG-Myristic acid-(SpacerC18)7-Fluos-BiotinTEG-3' | 9 pMol/μL-11 nMol |
| DMTrON-Synthesis/Coupling: 1 + 2 = 20 min-3-9 = 5 min-10-12 = 20 min/Standard-CPG-Cleavage/C18-Purification/F28-31-TEA+/evaporate/DMTrOFF/Fluos-Conc. | | | |
| BMO 29.891234__Ch03 | 10 μMol Scale | 5'-CholesterylTEG-CholesterylTEG-(SpacerC18)7-dT(Determ. of concentration)-BiotinTEG-3' | 239 pMol/μL-358 nMol |
| DMTrOFF-Synthesis-1000A-Universal-CPG/Coupling: 1 = 20 min-3-8 = 5 min-9-11 = 20 min/CPG-Cleavage = NH3-Isoprop/C8-Purification/F65-70-TEA+/evaporate/260 nm Conc. | | | |
| BMO 29.891234__Ch04 | 10 μMol Scale | 5'-CholesterylTEG-CholesterylTEG-(SpacerC18)7-dT(Determ. of concentration)-BiotinTEG-3' | 204 pMol/μL-307 nMol |
| DMTrOFF-Synthesis-Universal-PS/Coupling: 1 = 20 min-3-8 = 5 min-9-11 = 20 min/CPG-Cleavage = NH3-Isoprop/C8-Purification/F83-88-TEA+/evaporate/260 nm Conc. | | | |
| BMO 29.891234__Ch07 | 10 μMol Scale | 5'-CholesterylTEG-CholesterylTEG-(SpacerC18)9bis10-dT(Determ. of concentration)-BiotinTEG-3' | 277 pMol/μL-415 nMol |
| DMTrOFF-Synthesis-Universal-PS + Hyazinthactivator/SpacerC18 = 0.2M/Coupling: 1 + 2 = 3 min-3 = 2 × 5 min-4-11 = 3 min/CPG-Cleavage = NH3-Isoprop/C8-Purification/F55-59-Na+/Vivaspin 2'000/260 nm Conc. | | | |
| BMO 29.891234__Ch08 | 10 μMol Scale | 5'-CholesterylTEG-CholesterylTEG-(SpacerC18)9bis10-dT(Determ. of concentration)-BiotinTEG-3' | 306 pMol/μL-460 nMol |
| DMTrOFF-Synthesis-Universal-PS + Hyazinthactivator/SpacerC18 = 0.2M/Coupling: 1 + 2 = 3 min-3 = 2 × 5 min-4-11 = 3 min/CPG-Cleavage = NH3-Isoprop/C8-Purification/F37-41-Na+/Vivaspin 2'000/260 nm Conc. | | | |
| BMO 29.891234__Ch09 | 10 μMol Scale | 5'-CholesterylTEG-CholesterylTEG-(SpacerC18)7-SpacerC3-dT(Determ. of concentration)-BiotinTEG-3' | see below |
| DMTrOFF-Synthesis-1000A-Universal-CPG + Hyazinthactivator/SpacerC18 = 0.2M/Coupling: 1 + 2 = 3 min-3 + 4 = 2 × 10 min-5-10 = 10 min-11 + 12 = 3 min/CPG-Cleavage = NH3-Isoprop/crude und C8-Purification/F = see below/Vivaspin 2'000/260 nm Conc. | | | |
| | | T1__crude | 1'356 pMol/μL-2'033 nMol |
| | | T2__crude__Na | 1'165 pMol/μL-1'747 nMol |
| | | T3__F38-40 | 53 pMol/μL-80 nMol |
| | | T4__F38-40__Na | 51 pMol/μL-77 nMol |

-continued

| Internal No. | Scale | chemical structure (modular) | Yield |
|---|---|---|---|
| BMO 29.891236_Ch10 | 10 µMol Scale | 5'-CholesterylTEG-CholesterylTEG-(SpacerC18)7-SpacerC3-dT(Determ. of concentration)-BiotinTEG-3' | see below |
| DMTrOFF-Synthesis-10000A-Universal-CPG + Hyazinthactivator/SpacerC18 = 0.2M/Coupling: 1 + 2 = 3 min-3 + 4 = 2 × 10 min-5-10 = 10 min-11 + 12 = 3 min/CPG-Cleavage = NH3-Isoprop/CRUDE und C8-Purification/F = see below/Vivaspin 2'000/260 nm Conc. | | | |
| | T1_crude | | 2'430 pMol/µL-3'645 nMol |
| | T2_F37-39_Na | | 227 pMol/µL-341 nMol |
| BMO 29.891237_Ch11 | 10 µMol Scale | 5'-CholesterylTEG-CholesterylTEG-(SpacerC18)7-dT(Determ. of concentration)-BiotinTEG-p-3' | see below |
| DMTrOFF-Synthesis-2000A-dT-CPG/SpacerC18 = 0.2M/Coupling: 1 + 2 = 20 min-3 + 4 = 2 × 10 min-5-10 = 10 min-11 + 12 = 20 min/CPG-Cleavage = NH3-Isoprop/CRUDE und C8-Purification/F = see below/Vivaspin 2'000/260 nm Conc. | | | |
| | F42-45_Na | | 166 pMol/µL-248 nMol |
| | F47-49_Na | | 100 pMol/µL-150 nMol |
| BMO 29.891237_Ch12 | 10 µMol Scale | 5'-CholesterylTEG-CholesterylTEG-(SpacerC18)7-dT(Determ. of concentration)-BiotinTEG-p-3' | see below |
| DMTrOFF-Synthesis-2000A-dT-CPG/SpacerC18 = 0.2M/Coupling: 1 + 2 = 20 min-3 + 4 = 2 × 10 min-5-10 = 10 min-11 + 12 = 20 min/CPG-Cleavage = NH3-Isoprop/CRUDE und C8-Purification/F = see below/Vivaspin 2'000/260 nm Conc. | | | |
| | F51-53_Na | | 216 pMol/µL-324 nMol |
| | F56-59_Na | | 160 pMol/µL-250 nMol |

20

Exemplary Syntheses performed and results thereof:

A)

| Internal No. | Scale | 5'-mod | mod | spacer | label | 3'-mod | Yield | Notes |
|---|---|---|---|---|---|---|---|---|
| DK1194Ch02 | 1 µMol Scale | 5'-Myristic acid | Myristic acid | PEG-2000 | 6CarboxyFluos | Biotin-TEG-3' | 11 pMol/µL | synthesized and determined |
| DK1197 | 1 µMol Scale | 5'-Myristic acid SpacerC9 | Myristic acid | PEG-2000 | 6CarboxyFluos | Biotin-TEG-3' | 0.5 pMol/µL | synthesized and determined |
| DK1213 | 10 µMol Scale | 5'-Myristic acid | Myristic acid | SpacerC18 | 6CarboxyFluos | Biotin-TEG-3' | 538 pMol/µL | 2 charges synthesized and determined |
| DK1214 | 1 µMol Scale | 5'-Myristic acid | Myristic acid | (SpacerC18)x7 | 6CarboxyFluos | Biotin-TEG-3' | 100 pMol/µL | synthesized and determined |

B)

| Internal No. | Scale | 5'-mod | mod | spacer | label | 3'-mod | Yield | Notes |
|---|---|---|---|---|---|---|---|---|
| DK1213 | 10 µMol Scale | 5'-Myristic acid | Myristic acid | SpacerC18 | 6CarboxyFluos | Biotin-TEG-3' | 538 pMol/µL | 2 Charges synthesized and determined |
| DK1214 | 1 µMol Scale | 5'-Myristic acid | Myristic acid | (SpacerC18)x7 | 6CarboxyFluos | Biotin-TEG-3' | 100 pMol/µL | synthesized and determined |
| DK1218 | 1 µMol Scale | 5'-Myristic acid SpacerC9 | Myristic acid | (SpacerC18)x7 | 6CarboxyFluos | Biotin-TEG-3' | 40 pMol/µL | |
| DK1219 | 1 µMol Scale | 5'-Myristic acid SpacerC12 | Myristic acid | (SpacerC18)x7 | 6CarboxyFluos | Biotin-TEG-3' | 15 pMol/µL | |
| DK1220 | 1 µMol Scale | 5'-Myristic acid SpacerC18 | Myristic acid | (SpacerC18)x7 | 6CarboxyFluos | Biotin-TEG-3' | 56 pMol/µL | |
| DK1221 | 1 µMol Scale | 5'-Myristic acid Myristic acid | Myristic acid | (SpacerC18)x7 | 6CarboxyFluos | Biotin-TEG-3' | 38 pMol/µL | |
| DK1222 | 1 µMol Scale | 5'-Cholesteryl-TEG | Cholesteryl-TEG | (SpacerC18)x7 | 6CarboxyFluos | Biotin-TEG-3' | 12 + 6 + 13 pMol/µL | |
| DK1223 | 1 µMol Scale | 5'-Cholesteryl-TEG SpacerC9 | Cholesteryl-TEG | (SpacerC18)x7 | 6CarboxyFluos | Biotin-TEG-3' | synthesis difficulties | |
| DK1224 | 1 µMol Scale | 5'-Cholesteryl-TEG SpacerC12 | Cholesteryl-TEG | (SpacerC18)x7 | 6CarboxyFluos | Biotin-TEG-3' | 74 pMol/µL | |
| DK1225 | 1 µMol Scale | 5'-Cholesteryl-TEG SpacerC18 | Cholesteryl-TEG | (SpacerC18)x7 | 6CarboxyFluos | Biotin-TEG-3' | 5 pMol/µL | |
| DK1226 | 1 µMol Scale | 5'-Cholesteryl-TEG Cholesteryl-TEG | Cholesteryl-TEG | (SpacerC18)x7 | 6CarboxyFluos | Biotin-TEG-3' | synthesis difficulties | |
| DK1227 | 1 µMol Scale | 5'-Myristic acid | Cholesteryl-TEG | (SpacerC18)x7 | 6CarboxyFluos | Biotin-TEG-3' | 20 pMol/µL | |
| DK1228 | 1 µMol Scale | 5'-Cholesteryl-TEG | Myristic acid | (SpacerC18)x7 | 6CarboxyFluos | Biotin-TEG-3' | 9 pMol/µL | |
| DK1229 | 1 µMol Scale | 5'-Cholesteryl-TEG SpacerC3 Cholesteryl-TEG SpacerC3 | Cholesteryl-TEG | (SpacerC3)x7 | 6CarboxyFluos | Biotin-TEG-3' | | |
| | 1 µMol Scale | 5'-Cholesteryl-TEG SpacerC9 | Myristic acid | (SpacerC18)x7 | 6CarboxyFluos | Biotin-TEG-3' | | |
| | 1 µMol Scale | 5'-Cholesteryl-TEG SpacerC12 | Myristic acid | (SpacerC18)x7 | 6CarboxyFluos | Biotin-TEG-3' | | |
| | 1 µMol Scale Biotin-TEG | 5'-Cholesteryl-TEG SpacerC18 CPG 11 columns | Myristic acid | (SpacerC18)x7 | 6CarboxyFluos | Biotin-TEG-3' | | |

| ID | Scale | | | | | | Yield | Notes |
|---|---|---|---|---|---|---|---|---|
| DK1193 | | Myristic acid | PA-1 11 0.1M | 0.5 g | | | 4.50 mL ACN | |
| 10-1975 | | Cholesteryl-TEG | PA-2 13 0.1M | 1 × 0.25 g + 1 × 100 µMol à 11 + 4 Couplings | | | 3.10 mL ACN | |
| 10-1964 | | 6CarboxyFluos | PA-3 11 0.1M | 1 × 0.25 g + 1 × 100 µMol à 11 + 4 Couplings | | | 3.20 mL ACN | |
| 10-1909 | | SpacerC9 | PA-4 2 0.1M | 1 × 100 µMol | | | 1.00 mL ACN | |
| 10-1928 | | SpacerC12 | PA-5 2 0.1M | 1 × 100 µMol | | | 1.00 mL ACN | |
| 10-1918 | | Spacer-C18 | PA-6 79 0.1M | 5 × 0.25 g à 18 Couplings | | | 16.00 mL ACN | |

C)

| ID | Scale | 5'-end | | | | 3'-end | Yield | Notes |
|---|---|---|---|---|---|---|---|---|
| DK1213 | 10 µMol Scale | 5'-Myrisitic acid | Myristic acid | SpacerC18 | 6CarboxyFluos | Biotin-TEG-3' | 538 pMol/µL | 2 Charges synthesized and determined |
| DK1214 | 1 µMol Scale | 5'-Myristic acid | Myristic acid | (SpacerC18)x7 | 6CarboxyFluos | Biotin-TEG-3' | 100 pMol/µL | synthesized and determined |
| DK1218 | 1 µMol Scale | 5'-Myristic acid SpacerC9 | Myristic acid | (SpacerC18)x7 | 6CarboxyFluos | Biotin-TEG-3' | 40 pMol/µL | |
| DK1219 | 1 µMol Scale | 5'-Myristic acid SpacerC12 | Myristic acid | (SpacerC18)x7 | 6CarboxyFluos | Biotin-TEG-3' | 15 pMol/µL | |
| DK1220 | 1 µMol Scale | 5'-Myristic acid SpacerC18 | Myristic acid | (SpacerC18)x7 | 6CarboxyFluos | Biotin-TEG-3' | 56 pMol/µL | |
| DK1221 | 1 µMol Scale | 5'-Myristic acid Myristic acid | Myristic acid | (SpacerC18)x7 | 6CarboxyFluos | Biotin-TEG-3' | 38 pMol/µL | |
| DK1222 | 1 µMol Scale | 5'-Cholesteryl-TEG | Cholesteryl-TEG | (SpacerC18)x7 | 6CarboxyFluos | Biotin-TEG-3' | 12 + 6 + 13 pMol/µL | |
| DK1223 | 1 µMol Scale | 5'-Cholesteryl-TEG SpacerC9 | Cholesteryl-TEG | (SpacerC18)x7 | 6CarboxyFluos | Biotin-TEG-3' | synthesis difficulties | |
| DK1224 | 1 µMol Scale | 5'-Cholesteryl-TEG SpacerC12 | Cholesteryl-TEG | (SpacerC18)x7 | 6CarboxyFluos | Biotin-TEG-3' | 74 pMol/µL | |
| DK1225 | 1 µMol Scale | 5'-Cholesteryl-TEG SpacerC18 | Cholesteryl-TEG | (SpacerC18)x7 | 6CarboxyFluos | Biotin-TEG-3' | 5 pMol/µL | |
| DK1226 | 1 µMol Scale | 5'-Cholesteryl-TEG Cholesteryl-TEG | Cholesteryl-TEG | (SpacerC18)x7 | 6CarboxyFluos | Biotin-TEG-3' | synthesis difficulties | |
| DK1227 | 1 µMol Scale | 5'-Myristic acid | Cholesteryl-TEG | (SpacerC18)x7 | 6CarboxyFluos | Biotin-TEG-3' | 20 pMol/µL | |
| DK1228 | 1 µMol Scale | 5'-Cholesteryl-TEG | Myristic acid | (SpacerC18)x7 | 6CarboxyFluos | Biotin-TEG-3' | 9 pMol/µL | |
| DK1229 | 1 µMol Scale | 5'-Cholesteryl-TEG SpacerC3 Cholesteryl-TEG SpacerC3 | Cholesteryl-TEG | (SpacerC3)x7 | 6CarboxyFluos | Biotin-TEG-3' | | |
| | 1 µMol Scale | 5'-Cholesteryl-TEG SpacerC9 | Myristic acid | (SpacerC18)x7 | 6CarboxyFluos | Biotin-TEG-3' | no Synthesis | |
| | 1 µMol Scale | 5'-Cholesteryl-TEG SpacerC12 | Myristic acid | (SpacerC18)x7 | 6CarboxyFluos | Biotin-TEG-3' | no Synthesis | |
| | 1 µMol Scale | 5'-Cholesteryl-TEG SpacerC18 | Myristic acid | (SpacerC18)x7 | 6CarboxyFluos | Biotin-TEG-3' | no Synthesis | |
| DK1234 | 10 µMol Scale | 5'-Cholesteryl-TEG | Cholesteryl-TEG | (SpacerC18)x7 | dT (determination of concentration) | Biotin-TEG-3' | 239 + 307 pMol/µL | |

D) Chemical Structures of the Exemplary Compounds of the Invention as Well as Side Products The chemical structures of the exemplary compounds of the invention as well as side products of synthesis are depicted in FIGS. 6 A and B.

E) Synthesis of Biotin-PEG-Lys-(C18)2

The synthesis of Biotin-PEG-Lys-(C18)2 of the invention is shown in FIG. 6 C.

F) Structures of Further Compounds of the Invention and Reference Compounds, as Well as Intermediates Thereof For synthesis of compounds of the invention and reference compounds, following intermediates were used:

cholesteryl-TEG-CE-PA (Glen Research 10-1975),
myristic acid-CE-PA (inhouse production),
biotin-TEG-CE-PA (Glen Research 10-1955),
biotin-dT-CE-PA (GlenResearch 10-1038),
dT-CE-PA (GlenResearch 10-1030),
symmetric doubler-CE-PA (GlenResearch 10-1920),
PEG-200-CED-PA (ChemGenes CLP-2119),
6-Fluorescein-CE-PA (Glen Research 10-1964) and
universal-CPG (Proligo 1000A M401010).

Structures of further compounds of the invention and reference compounds, as well as intermediates are shown in FIG. 12.

2. Labelling of Cells Using Compounds of the Invention
WBC: white blood cells

| | Linol (1,1'-dilinoleyl-3,3,3',3'-tetramethyl-indocarbocyanine perchlorate, Invitrogen) | Oleyl (NOF-BAM) | PKH26 (Myristic acid, behenic acid; SIGMA) | PKH67 (SIGMA) | PKH2 (SIGMA) | Phosphatidyl-ethanolamine (N-(4,4-difluoro-5,7-dimethyl-4-bora-3a,4a-diaza-s-indacene-3-propionyl)-1,2-dihexadecanoyl-sn-glycero-3-phosphoethanol-amine, triethyl-ammonium salt, Invitrogen) | Sphingomyelin (N-(4,4-difluoro-5,7-dimethyl-4-bora-3a,4a-diaza-s-indacene-3-penta-noyl)sphingosyl phosphocholine; Invitrogen) |
|---|---|---|---|---|---|---|---|
| WBCs | is taken up by most cells (more in comparison to other molecules (Exposure time: 20-50 ms) √ | is not taken up by all cells (granulocytes potentially negative) √ | stains granulocytes and almost all other blood cells (1 Exp.: 3 cells not stained) √ | stains almost all cells; apparently no monocytes, combination of linol and PKH67- all cells stained √ | does not stain all cells, other PKHs better √ | x | (x)- very bad |
| U937 | √ | | √ | | | | |
| MDA-MB468 | √ | √ not all | √ | | | | |
| Jurkats | √ | √ | √ | | | x | x |
| CHO | √ | | √ | | | x | x very weak |
| COS 7 | √ | | √ | | | x | x |
| Hela | √ | | √* | | | x/√ very weak | √ |
| NIH 3T3 | √ | | √ | | | x | x |
| Epithelial cells | √ | √ | √ not all | √ | √ not all | x | √ |

*one cell stained weakly

| | Cholesterol (Invitrogen; cholesteryl 4,4-difluoro-5-(2-pyrrolyl)-4-bora-3a,4a-diaza-s-indacene-3-undecanoate) | BMO 29.891133 ID: 3882 5'-XXYZ-3' X = Cholesteryl-TEG Y = PEG2000 Z = Fluos | BMO: 29.891132 ID: 3880 5'-XYZ-3' X = Cholesteryl-TEG Y = PEG2000 Z = Fluos | BMO: 29.891131 ID: 3879 5'-XYZ-3' X = a-Tocopherol-TEG Y = PEG2000 Z = Fluos | 1,1'-Dioctadecyl-3,3,3',3'-tetramethyl-indocarbocyanin perchlorate Sigma 42364 -100 mg | BMO: 15.000078 Sulfo-JA133-phenylboronic acid |
|---|---|---|---|---|---|---|
| WBCs | x | taken up by most cells (more in comparison to other molecules (Exposure time: 50-200 ms) √ | √ not all | √ not all | √ not all | √ not all |
| U937 | | √ | √ | √ | √ | |
| MDA-MB468 | | √ | √ | √ | √ | |
| Jurkats | x | √ | | | √ | |
| CHO | x | √ | | | √ | |
| COS 7 | x | √ | | | √ | |
| Hela | x/√ | √ | | | √ | |
| NIH 3T3 | x | √ | | | √* | |
| Epithelial cells | x very weak | √ | √ | √ | √ | √ |

*one cell not stained

Example 3: Results of Experiments Relating to the Immobilization of Cells

The following applies for modular description of the compounds below:

X=hydrophobic moiety, Y=PEG2000, Z=Biotin-TEG, F=Fluos=fluorescein

In the following experiment, the recovery rate of cells was determined.

| tested compound | modular structure | Internal Reference number | Recovery Rate | cells | concentration |
|---|---|---|---|---|---|
| Sunbright(OE-080CS)DADOO-Biotin | | 15.260250 | | | |
| BAM-SH | | 15.260254 | 28.0% | WBCs | |
| Cholesteryl-TEG-Cholesteryl-TEG-PEG2000-Biotin-TEG | 5'-XXYZ-3' | 29.891137 | 77.1% | WBCs | |
| Biotin-PEG2000-Boronic acid | | 15.260267 | 16.3% | WBCs | |
| Cholesteryl-TEG-Cholesteryl-TEG-PEG2000-Fluos-Biotin-TEG | 5'-XXYFZ-3' | 29.891180 | 71-90% | WBCs | 350 pmol/10e6 cells |
| | | | 77.7% | WBCs | 350 pmol/10e6 cells |
| | | | 62.3% | WBCs | 350 pmol/10e6 cells |
| | | | 95.8% | WBCs | 350 pmol/10e6 cells |
| | | | 77.9% | WBCs | 350 pmol/10e6 cells |
| | | | 88.5% | WBCs | 350 pmol/10e6 cells |
| | | | 69.7% | WBCs | 350 pmol/10e6 cells |
| | | | 79.2% | WBCs | 350 pmol/10e6 cells |
| | | | 72.5% | WBCs | 350 pmol/10e6 cells |
| 1,2 Distearoyl-sn-glycero-3-phosphoethanolamine-N-[biotinyl(PEG2000] | DSPE-PEG(2000) Biotin (Avantilipids) | | 54-83% | WBCs | 350 pmol/10e6 cells |
| Myristic acid-Myristic acid-PEG2000-Fluos-Biotin-TEG | 5'-XXYFZ-3' | 29.891194 | 21-26% | WBCs | 350 pmol/10e6 cells |
| Biotin-PEG-lys-(C14)2 | | 15.260268 | 52-86% | WBCs | |
| Myristic acid-Myristic acid-(SpacerC18)7-Fluos-Biotin-TEG | 5'-XXYYYYYYYFZ-3' (Y = Spacer) | 29.891214 | 78.9% | WBCs | 350 pmol/10e6 cells |
| | | | 68.7% | WBCs | 350 pmol/10e6 cells |
| | | | 90.5% | WBCs | 350 pmol/10e6 cells |
| | | | 81.1% | WBCs | 350 pmol/10e6 cells |
| | | | 65.9% | WBCs | 350 pmol/10e6 cells |
| | | | 84.9% | WBCs | 350 pmol/10e6 cells |
| | | | 85.1% | WBCs | 350 pmol/10e6 cells |
| Myristic acid-Myristic acid-SpacerC18-Fluos-Biotin-TEG | 5'-XXYFZ-3' (Y = Spacer) | 29.891213 | 67.4% | WBCs | 350 pmol/10e6 cells |
| | | | 61.9% | WBCs | 350 pmol/10e6 cells |
| | | | 80.2% | WBCs | 350 pmol/10e6 cells |
| | | | 70.4% | WBCs | 350 pmol/10e6 cells |
| Myristic acid-SpacerC9-Myristic acid-PEG2000-Fluos-Biotin-TEG | 5'-XSXYFZ-3' (S = Spacer) | 29.891197 | not enough material; staining not good | WBCs | |
| Myristic acid-SpacerC9-Myristic acid-(SpacerC18)7-Fluos-Biotin-TEG | 5'-XYXYYYYYYYFZ-3' (Y = Spacer) | 29.891218 | 50.3% | WBCs | 350 pmol/10e6 cells |
| | | | 55.1% | WBCs | 350 pmol/10e6 cells |
| Myristic acid-Cholesteryl-TEG-(SpacerC18)7-Fluos-Biotin-TEG | 5'-XEYYYYYYYFZ-3' (Y = Spacer; X = Myr.; E = Chol.)) | 29.891227 | 64.9% | WBCs | 350 pmol/10e6 cells |
| | | | 69.6% | WBCs | 350 pmol/10e6 cells |
| | | | 77.8% | WBCs | 350 pmol/10e6 cells |
| | | | 77.8% | WBCs | 350 pmol/10e6 cells |
| (Myristic acid)3-(SpacerC18)7-Fluos-Biotin-TEG | 5'-XXXYYYYYYYFZ-3' (Y= Spacer) | 29.891221 | 46.0% | WBCs | 350 pmol/10e6 cells |
| | | | 79.4% | WBCs | 350 pmol/10e6 cells |
| | | | 68.8% | WBCs | 350 pmol/10e6 cells |
| | | | 76.5% | WBCs | 350 pmol/10e6 cells |
| | | | 83.4% | WBCs | 350 pmol/10e6 cells |
| Myristic acid-SpacerC12-Myristic acid-(SpacerC18)7-Fluos-Biotin-TEG | 5'-XVXYYYYYYYFZ-3' (V = Spacer C12, Y = Spacer C18) | 29.891219 | 46.3% | WBCs | 350 pmol/10e6 cells |
| | | | 39.4% | WBCs | 350 pmol/10e6 cells |
| | | | 53.7% | WBCs | 350 pmol/10e6 cells |
| | | | 56.6% | WBCs | 350 pmol/10e6 cells |
| Myristic acid-SpacerC18-Myristic acid-(SpacerC18)7-Fluos-Biotin-TEG | 5'-XYXYYYYYYYFZ-3' (Y = Spacer C18) | 29.891220 | 35.8% | WBCs | 350 pmol/10e6 cells |
| | | | 41.4% | WBCs | 350 pmol/10e6 cells |
| | | | 55.9% | WBCs | 350 pmol/10e6 cells |
| | | | 63.5% | WBCs | 350 pmol/10e6 cells |
| Cholesteryl-TEG-Cholesteryl-TEG-(SpacerC18)7-Fluos-Biotin-TEG | 5'-XXYYYYYYYFZ-3' (Y = Spacer C18) | 29.891222 | 52.6% | WBCs | 350 pmol/10e6 cells |
| | | | 76.3% | WBCs | 350 pmol/10e6 cells |
| | | | 80.3% | WBCs | 350 pmol/10e6 cells |
| | | | 70.4% | WBCs | 350 pmol/10e6 cells |
| | | | 71.3% | WBCs | 350 pmol/10e6 cells |
| | | | 80.3% | WBCs | 350 pmol/10e6 cells |
| | | | 4.1% | WBCs | 350 pmol/10e6 cells |

| | | | | | | |
|---|---|---|---|---|---|---|
| | | | 38.8% | WBCs | 350 pmol/10e6 cells | |
| | | | 13.0% | WBCs | 350 pmol/10e6 cells | undiluted |
| | | | 11.0% | WBCs | 350 pmol/10e6 cells | 1:1 diluted |
| | | | 77.0% | WBCs | 350 pmol/10e6 cells | undiluted |
| | | | 79.0% | WBCs | 350 pmol/10e6 cells | 1:1 diluted |
| | | | 23.0% | WBCs | 350 pmol/10e6 cells | untreated |
| | | | 17.0% | WBCs | 350 pmol/10e6 cells | US + 10' 98° C. |
| | | | 68.0% | WBCs | 350 pmol/10e6 cells | untreated |
| | | | 61.0% | WBCs | 350 pmol/10e6 cells | US + 10' 98° C. |
| Cholesteryl-TEG-SpacerC12-Cholesteryl-TEG-(SpacerC18)7-Fluos-Biotin-TEG | 5'-XWXYYYYYYYFZ-3' (W = Spacer C12, Y = Spacer C18) | 29.891224 | 119.4% | WBCs | 350 pmol/10e6 cells | |
| | | | 60.6% | WBCs | 350 pmol/10e6 cells | |
| | | | 64.4% | WBCs | 350 pmol/10e6 cells | |
| | | | 70.3% | WBCs | 350 pmol/10e6 cells | |
| | | | 78.1% | WBCs | 350 pmol/10e6 cells | |
| Cholesteryl-TEG-SpacerC18-Cholesteryl-TEG-(SpacerC18)7-Fluos-Biotin-TEG | 5'-XYXYYYYYYYFZ-3' (Y = Spacer C18) | 29.891225 | 38.8% | WBCs | 350 pmol/10e6 cells | |
| | | | 46.5% | WBCs | 350 pmol/10e6 cells | |
| Cholesteryl- Myristic acid-TEG-(SpacerC18)7-Fluos-Biotin-TEG | 5'-EXYYYYYYYFZ-3' (Y = Spacer; X = Myr.; E = Chol.)) | 29.891228 | 76.1% | WBCs | 350 pmol/10e6 cells | |
| | | | 64.0% | WBCs | 350 pmol/10e6 cells | |
| | | | 17.4% | WBCs | 350 pmol/10e6 cells | |
| | | | 52.1% | WBCs | 350 pmol/10e6 cells | |
| Cholesteryl-TEG-Cholesteryl-TEG-(SpacerC18)7-Biotin-TEG | 5'-XXYYYYYYYTZ-3' (Y = Spacer C18) | 29.891234 | 9.6% | WBCs | 10 pmol/10e6 cells | |
| | | | 18.8% | WBCs | 100 pmol/10e6 cells | |
| | | | 24.9% | WBCs | 500 pmol/10e6 cells | |
| | | | 35.4% | WBCs | 1000 pmol/10e6 cells | |
| | | | 12.0% | WBCs | 350 pmol/10e6 cells | undiluted |
| | | | 22.0% | WBCs | 350 pmol/10e6 cells | 1:1 diluted |
| | | | 17.0% | WBCs | 350 pmol/10e6 cells | untreated |
| | | | 27.0% | WBCs | 350 pmol/10e6 cells | US + 10' 98° C. |
| | | | 10.0% | WBCs | 350 pmol/10e6 cells | 0.001% Tween20 |
| | | | 12.0% | WBCs | 350 pmol/10e6 cells | 0.0003% Tween20 |
| | | | 22.0% | WBCs | 350 pmol/10e6 cells | 0.0001% Tween21 |
| | | | 22.0% | WBCs | 350 pmol/10e6 cells | 0.00003% Tween22 |
| | | | 12.0% | WBCs | 350 pmol/10e6 cells | 0.00003% Tween20 |
| | | | 14.0% | WBCs | 350 pmol/10e6 cells | 0.00001% Tween20 |
| | | | 13.0% | WBCs | 350 pmol/10e6 cells | 0.000003% Tween21 |
| | | | 11.0% | WBCs | 350 pmol/10e6 cells | 0.0% Tween22 |
| | | | 26.8% | WBCs | 300 pmol/10e6 cells | |
| | | | 41.7% | WBCs | 1 nmol/10e6 cells | |
| | | | 99.7% | WBCs | 10 nmol/10e6 cells | |
| | | | 36.0% | WBCs | 350 pmol/10e6 cells | undiluted |
| | | | 25.0% | WBCs | 350 pmol/10e6 cells | 1:1 diluted |
| | | | 13.0% | WBCs | 350 pmol/10e6 cells | untreated |
| | | | 23.0% | WBCs | 350 pmol/10e6 cells | US + 10' 98° C. |
| | | | 15.0% | WBCs | 350 pmol/10e6 cells | 0.001% Tween20 |
| | | | 18.0% | WBCs | 350 pmol/10e6 cells | 0.0003% Tween20 |
| | | | 28.0% | WBCs | 350 pmol/10e6 cells | 0.0001% Tween21 |
| | | | 36.0% | WBCs | 350 pmol/10e6 cells | 0.00003% Tween22 |
| | | | 20.0% | WBCs | 350 pmol/10e6 cells | 0.00003% Tween20 |
| | | | 23.0% | WBCs | 350 pmol/10e6 cells | 0.00001% Tween20 |
| | | | 25.0% | WBCs | 350 pmol/10e6 cells | 0.000003% Tween21 |
| | | | 35.0% | WBCs | 350 pmol/10e6 cells | 0.0% Tween22 |
| Biotin-PEG-Lysin-C18 (Stearic acid) | | 15.260271 | 21.0% | WBCs | 350 pmol/10e6 cells | also not better at higher concentrations |

-continued

| | | | | | |
|---|---|---|---|---|---|
| Biotin-PEG-Lysin-C22 (Behenic acid) | | | 27.0% | WBCs | 350 pmol/10e6 cells | also not better at higher concentrations |
| Biotin-PEG-Lysin-(C18)2 dissolved in | | | 4.8% | WBCs | 10 pmol/10e6 cells | |
| | | | 6.8% | WBCs | 100 pmol/10e6 cells | |
| | | | 21.8% | WBCs | 1 nmol/10e6 cells | |
| | | | 60.6% | WBCs | 10 nmol/10e6 cells | |
| | | | 43.0% | WBCs | 10 nmol/10e6 cells | |
| | | | 69.0% | WBCs | 50 nmol/10e6 cells | |
| | | | 81.8% | WBCs | 100 nmol/10e6 cells | |
| | | | 29.6% | WBCs | 1 nmol/10e6 cells | |
| | | | 68.5% | WBCs | 10 nmol/10e6 cells | |
| | | | 83.9% | WBCs | 100 nmol/10e6 cells | |
| | | | 9.0% | WBCs | 350 pmol/10e6 cells | 0.001% Tween20 |
| | | | 10.0% | WBCs | 350 pmol/10e6 cells | 0.0003% Tween20 |
| | | | 10.0% | WBCs | 350 pmol/10e6 cells | 0.0001% Tween21 |
| | | | 15.0% | WBCs | 350 pmol/10e6 cells | 0.00003% Tween22 |
| | | | 75.0% | WBCs | 100 nmol/10e6 cells | |
| | | | 44.0% | WBCs | 5 nmol/10e6 cells | |
| | | | 25.0% | WBCs | 0.5 nmol/10e6 cells | |
| | | | 66.0% | WBCs | 100 nmol/10e6 cells | |
| | | | 34.0% | WBCs | 5 nmol/10e6 cells | |
| | | | 27.0% | WBCs | 0.5 nmol/10e6 cells | |
| | | | 33.0% | WBCs | 100 nmol/10e6 cells | maybe to due 1.5-2 h exposure of plate |
| | | | 16.0% | WBCs | 5 nmol/10e6 cells | |
| | | | 38.0% | WBCs | 0.5 nmol/10e6 cells | |
| Cholesteryl-TEG-Cholesteryl-TEG-(SpacerC18)7-Biotin-TEG | 5'-XXYYYYYYYYTZ-3' (Y = Spacer C18) | 29.891234 | 18.0% | WBCs | 350 pmol/10e6 cells | not evaporated, VIVA Spin |
| | | | 42.0% | WBCs | 1000 pmol/10e6 cells | nicht not evaporated, VIVA Spin |
| Cholesteryl-TEG-Cholesteryl-TEG-(SpacerC18)7-Biotin-TEG | 5'-XXYYYYYYYYTZ-3' (Y = Spacer C18) | 29.891234 | 19.0% | WBCs | 350 pmol/10e6 cells | not evaporated, VIVA Spin |
| | | | 45.0% | WBCs | 1000 pmol/10e6 cells | not evaporated, VIVA Spin |
| 5'-(Cholesteryl-TEG)2-(SpacerC18)7-dT-Biotin-TEG-3' | 5'-YY XXXXXXXTZ-3' (X = SpacerC18) | 29.891234 | 7.0% | WBCs | 350 pmol/10e6 cells | |
| | | | 13.0% | WBCs | 1 nmol/10e6 cells | |
| 5'-(Cholesteryl-TEG)2-(SpacerC18)7-dT-Biotin-TEG-3' | 5'-YY XXXXXXXTZ-3' (X = SpacerC18) | 29.891234 | 63.0% | WBCs | 350 pmol/10e6 cells | |
| | | | 71.0% | WBCs | 1 nmol/10e6 cells | |
| 5'-(Cholesteryl-TEG)2-(SpacerC18)7-dT-Biotin-TEG-3' | 5'-YY XXXXXXXTZ-3' (X = SpacerC18) | 29.891234 | 52.0% | WBCs | 350 pmol/10e6 cells | |
| | | | 78.0% | WBCs | 1 nmol/10e6 cells | |
| 5'-(Cholesteryl-TEG)2-(SpacerC18)7-SpacerC3-dT-Biotin-TEG-3' | 5'-YY XXXXXXXWTZ-3' (W = Spacer C3, X = SpacerC18) | 29.891234 | 33.0% | WBCs | 350 pmol/10e6 cells | |
| | | | 44.0% | WBCs | 1 nmol/10e6 cells | |
| 5'-(Cholesteryl-TEG)2-(SpacerC18)7-SpacerC3-dT-Biotin-TEG-3' | 5'-YY XXXXXXXWTZ-3' (W = Spacer C3, X = SpacerC18) | 29.891236 | 46.0% | WBCs | 350 pmol/10e6 cells | |
| | | | 64.0% | WBCs | 1 nmol/10e6 cells | |
| 5'-(Cholesteryl-TEG)2-(SpacerC18)7-SpacerC3-dT-Biotin-TEG-3' | 5'-YY XXXXXXXWTZ-3' (W = Spacer C3, X = SpacerC18) | 29.891236 | 37.0% | WBCs | 350 pmol/10e6 cells | |
| | | | 47.0% | WBCs | 1 nmol/10e6 cells | |
| 5'-(Cholesteryl-TEG)2-(SpacerC18)7-SpacerC3-dT-Biotin-TEG-3' | 5'-YY XXXXXXXWTZ-3' (W = Spacer C3, X = SpacerC18) | 29.891237 | 8.1% | WBCs | 10 pmol/10e6 cells | |
| | | | 15.1% | WBCs | 100 pmol/10e6 cells | |
| | | | 41.3% | WBCs | 1 nmol/10e6 cells | |
| | | | 59.1% | WBCs | 10 nmol/10e6 cells | |
| 5'-(Cholesteryl-TEG)2-(SpacerC18)7-SpacerC3-dT-Biotin-TEG-3' | 5'-YY XXXXXXXWTZ-3' (W = Spacer C3, X = SpacerC18) | 29.891237 | 10.5% | WBCs | 10 pmol/10e6 cells | |
| | | | 16.4% | WBCs | 100 pmol/10e6 cells | |
| | | | 35.4% | WBCs | 1 nmol/10e6 cells | |
| | | | 62.0% | WBCs | 10 nmol/10e6 cells | |
| 5'-(Cholesteryl-TEG)-(SpacerC18)7-dT-Biotin-TEG-3' | 5'-Y XXXXXXXTZ-3' (W = Spacer C3, X = SpacerC18) | 29.891244 | 14.0% | WBCs | 10 pmol/10e6 cells | |
| | | | 27.00% | WBCs | 100 pmol/10e6 cells | |
| | | | 51.00% | WBCs | 1 nmol/10e6 cells | |
| | | | 57.00% | WBCs | 10 nmol/10e6 cells | |
| 5'-(Cholesteryl-TEG)2-(SpacerC18)7-dT-Biotin-TEG-3' | 5'-YY XXXXXXXTZ-3' (W = Spacer C3, X = SpacerC18) | 29.891246 | 9.50% | | 10 pmol/10e6 cells | |
| | | | 20.50% | | 100 pmol/10e6 cells | |
| | | | 50.70% | | 1 nmol/10e6 cells | |
| | | | 68.90% | | 10 nmol/10e6 cells | |
| 5'-(SpacerC18)7-dT-Biotin-TEG-3' | 5'-XXXXXXXTZ-3' (W = Spacer C3, X = SpacerC18) | 29.891245 | 9.30% | | 10 pmol/10e6 cells | |
| | | | 6.20% | | 100 pmol/10e6 cells | |
| | | | 8.40% | | 1 nmol/10e6 cells | |
| | | | 27.50% | | 10 nmol/10e6 cells | |

| | | | | |
|---|---|---|---|---|
| 5'-(Cholesteryl-TEG)2-(SpacerC18)7-dT-Biotin-TEG-3' | 5'-YY XXXXXXXTZ-3' (W = Spacer C3, X = SpacerC18) | 29.891246 | 74.50% | 10 nmol/10e6 cells |
| 5'-(Cholesteryl-TEG)-(SpacerC18)7-dT-Biotin-TEG-3' | 5'-Y XXXXXXXTZ-3' (W = Spacer C3, X = SpacerC18) | 29.891244 | 51.70% | 10 nmol/10e6 cells |
| 5'-(SpacerC18)7-dT-Biotin-TEG-3' | 5'-XXXXXXXTZ-3' (W = Spacer C3, X = SpacerC18) | 29.891245 | 24.70% | 10 nmol/10e6 cells |
| Mixture of 44 + 45 + 46 | | | 66.90% | 10 nmol/10e6 cells |
| 5'-(Cholesteryl-TEG)2-(SpacerC18)7-dT-Biotin-TEG-3' | 5'-YY XXXXXXXTZ-3' (W = Spacer C3, X = SpacerC18) | 29.891246 | 87.16% | 10 nmol/10e6 cells |
| 5'-(Cholesteryl-TEG)-(SpacerC18)7-dT-Biotin-TEG-3' | 5'-Y XXXXXXXTZ-3' (W = Spacer C3, X = SpacerC18) | 29.891244 | 63.70% | 10 nmol/10e6 cells |
| 5'-(SpacerC18)7-dT-Biotin-TEG-3' | 5'-XXXXXXXTZ-3' (W = Spacer C3, X = SpacerC18) | 29.891245 | 26.50% | 10 nmol/10e6 cells |
| Mixture of 44 + 45 + 46 | | | 79.46% | 10 nmol/10e6 cells |
| 5'-(SpacerC18)-dT-Biotin-TEG-3' | 5'-XTZ-3' (W = Spacer C3, X = SpacerC18) | 29891240 | 12.80% | 1 nmol/10e6 cells |
| | | | 14.90% | 10 nmol/10e6 cells |
| 5'-(Cholesteryl-TEG)2-(SpacerC18)7-dT-Biotin-TEG-3' | 5'-YY XXXXXXXTZ-3' (W = Spacer C3, X = SpacerC18) | 29.891246 | 85.50% | 1 nmol 1C18 + 10 nmol CholChol |
| Mix | | | 83.22% | 10 nmol 1C18 + 10 nmol CholChol |
| 1,2 Distearoyl-sn-glycero-3-phosphoethanolamine-N-[biotinyl(PEG2000] | DSPE-PEG(2000) Biotin (Avantilipids) | | 70.80% | 10 nmol/10^6 Distearine without EDTA-K |
| | | | 71.60% | 10 nmol/10^6 Distearine 0.3 mM EDTA-K |
| | | | 76.50% | 10 nmol/10^6 Distearine 1 mM EDTA-K |
| | | | 72.00% | 10 nmol/10^6 Distearine 3 mM EDTA-K |
| | | | 78.30% | 10 nmol/10^6 Distearine without EDTA-K |
| | | | 82.70% | 10 nmol/10^6 Distearine 0.3 mM EDTA-K |
| | | | 88.50% | 10 nmol/10^6 Distearine 1 mM EDTA-K |
| | | | 81.80% | 10 nmol/10^6 Distearine 3 mM EDTA-K |
| | | | 68.90% | 10 nmol/10e6 cells |
| | | | 69.60% | 10 nmol/10e6 cells |
| | | | 68.90% | 10 nmol/10e6 cells |
| | | | 95.90% | 10 nmol/10e6 cells |
| | | | 84.40% | 10 nmol/10e6 cells |
| | | | 90.80% | 10 nmol/10e6 cells |
| 1,2-Dioleyl-sn-Glycero-3-Phosphoethanolamin-N-(Cap-Biotin)-Na | Avantilipids | | 66.30% | 10 pmol/10e6 cells |
| | | | 91.10% | 100 pmol/10e6 cells |
| | | | 95.80% | 1 nmol/10e6 cells |
| | | | 20.60% | without Linker |
| | | | 74.40% | 10 pmol/10e6 cells |
| | | | 107.10% | 100 pmol/10e6 cells |
| | | | 101.76% | 1 nmol/10e6 cells |
| | | | 26.85% | without Linker |
| | | | 81.00% | 100 pmol/10e6 cells |
| | | | 80.10% | 100 pmol/10e6 cells |
| | | | 64.90% | 100 pmol/10e6 cells |
| | | | 80.55% | 100 pmol/10e6 cells |
| | | | 70.85% | 100 pmol/10e6 cells |
| | | | 80.74% | 100 pmol/10e6 cells |
| | | | 53.97% | 100 pmol/10e6 cells |
| | | | 69.60% | 100 pmol/10e6 cells |
| | | | 80.16% | 500 pmol/10e6 cells |
| | | | 95.94% | 500 pmol/10e6 cells |
| | | | 89.19% | 10 nmol/10e6 cells |
| | | | 105.12% | 10 nmol/10e6 cells |

-continued

| Name | Type | Number | Percentage | Amount | Notes |
|---|---|---|---|---|---|
| Dipalmityl-sn-Glycero-3-Phosphoethanolamin-N-(Cap-Biotin)-Na | Avantilipids | | 54.30% | 10 pmol/10e6 cells | |
| | | | 72.20% | 100 pmol/10e6 cells | |
| | | | 84.90% | 1 nmol/10e6 cells | |
| | | | 11.10% | without Linker | |
| | | | 45.40% | 10 pmol/10e6 cells | |
| | | | 86.10% | 100 pmol/10e6 cells | |
| | | | 89.30% | 1 nmol/10e6 cells | |
| | | | 14.10% | without Linker | |
| | | | 51.80% | 300 pmol/10e6 cells | |
| | | | 55.90% | 300 pmol/10e6 cells | |
| | | | 52.60% | 300 pmol/10e6 cells | |
| | | | 73.07% | 300 pmol/10e6 cells | |
| | | | 61.27% | 300 pmol/10e6 cells | |
| | | | 71.40% | 300 pmol/10e6 cells | |
| 5'-(Cholesteryl-TEG)2-PEG2000-Fluos-Biotin__TEG-3' | purified | 29.891.247 | 13.38% | 10 pmol/10e6 cells | |
| | | | 15.26% | 100 pmol/10e6 cells | |
| | | | 13.27% | 1 nmol/10e6 cells | |
| | | | 45.75% | 10 nmol/10e6 cells | |
| 5'-(Cholesteryl-TEG)2-Spacer C18-Fluos-Biotin__TEG-3' | purified | 29.891.251 | 25.57% | 10 pmol/10e6 cells | |
| | | | 57.82% | 100 pmol/10e6 cells | |
| | | | 89.71% | 1 nmol/10e6 cells | |
| | | | 92.63% | 10 nmol/10e6 cells | |
| | | | 68.57% | 100 pmol/10e6 cells | |
| | | | 82.61% | 1 nmol/10e6 cells | |
| 5'-(Cholesteryl-TEG)2-PEG2000-Fluos-Biotin__TEG-3' INVERS | purified | 29.891248 | 32.80% | 10 pmol/10e6 cells | |
| | | | 65.36% | 100 pmol/10e6 cells | |
| | | | 83.99% | 1 nmol/10e6 cells | |
| | | | 81.10% | 10 nmol/10e6 cells | |
| | | | 70.75% | 100 pmol/10e6 cells | |
| | | | 86.03% | 1 nmol/10e6 cells | |
| 5'-(Cholesteryl-TEG)2-Spacer C18-Fluos-Biotin__TEG-3' INVERS | purified | 29.891254 | 40.30% | 10 pmol/10e6 cells | |
| | | | 64.60% | 100 pmol/10e6 cells | |
| | | | 92.50% | 1 nmol/10e6 cells | |
| | | | 83.60% | 10 nmol/10e6 cells | |
| | | | 57.63% | 100 pmol/10e6 cells | |
| | | | 82.19% | 1 nmol/10e6 cells | |
| | | | 65.69% | 100 pmol/10e6 cells | |
| | | | 81.79% | 1 nmol/10e6 cells | |
| | | | 70.07% | 100 pmol/10e6 cells | |
| | | | 81.28% | 100 pmol/10e6 cells | |
| | | | 74.68% | 1 nmol/10e6 cells | |
| 3'-(Myristic acid)2-PEG2000-dT-Biotin-TEG-5' INVERS | unpurified | 29.891255 | 24.70% | 10 pmol/10e6 cells | |
| | | | 50.61% | 100 pmol/10e6 cells | |
| | | | 87.55% | 1 nmol/10e6 cells | |
| | | | 83.53% | 10 nmol/10e6 cells | |
| 3'-(Myristic acid)2-PEG2000-Fluos-Biotin-TEG-5' INVERS | unpurified | 29.891256 | 35.79% | 10 pmol/10e6 cells | |
| | | | 73.42% | 100 pmol/10e6 cells | |
| | | | 85.13% | 1 nmol/10e6 cells | |
| 5'-(Cholesteryl-TEG)2-PEG2000-dT-Biotin__TEG-3' | unpurified | 29.891249 | 11.38% | 10 pmol/10e6 cells | |
| | | | 16.16% | 100 pmol/10e6 cells | |
| | | | 37.73% | 1 nmol/10e6 cells | |
| | | | 61.04% | 10 nmol/10e6 cells | |
| 5'-(Cholesteryl-TEG)2-Spacer C18-dT-Biotin__TEG-3' INVERS | unpurified | 29.891252 | 28.56% | 10 pmol/10e6 cells | |
| | | | 55.41% | 100 pmol/10e6 cells | |
| | | | 71.99% | 1 nmol/10e6 cells | |
| | | | 88.05% | 10 nmol/10e6 cells | |
| | | | 16.03% | 10 nmol/10e6 cells | |
| | | | 52.46% | 100 pmol/10e6 cells | |
| | | | 80.83% | 1 nmol/10e6 cells | |
| | | | 85.47% | 10 nmol/10e6 cells | |
| 5'-(Cholesteryl-TEG)2-Spacer C12-dT-Biotin__TEG-3' INVERS | unpurified | 29.891253 | 47.42% | 10 pmol/10e6 cells | |
| | | | 73.46% | 100 pmol/10e6 cells | |
| | | | 96.84% | 1 nmol/10e6 cells | |
| | | | 102.36% | 10 nmol/10e6 cells | |
| | | | 41.44% | 100 pmol/10e6 cells | |
| | | | 72.13% | 1 nmol/10e6 cells | |
| | | | 62.59% | 100 pmol/10e6 cells | |
| | | | 79.02% | 1 nmol/10e6 cells | |
| 5'-(Chol-TEG)1-Doubler-dT-Biotin-3' | | 29.891272 | 65.03% | 10 pmol/10e6 cells | |
| | | | 83.08% | 100 pmol/10e6 cells | |
| | | | 87.93% | 1 nmol/10e6 cells | |
| | | | Cells lysed | 10 nmol/10e6 cells | Vesicle formation |
| | | | 56.49% | 100 pmol/10e6 cells | |
| | | | 72.13% | 1 nmol/10e6 cells | |
| | | | 62.11% | 100 pmol/10e6 cells | |
| | | | 82.47% | 1 nmol/10e6 cells | |
| | | | 82.01% | 100 pmol/10e6 cells | |

-continued

| | | | | |
|---|---|---|---|---|
| 5'-(Cholesteryl-TEG)2-PEG2000-dT-Biotin_TEG-3' | purified | 29.891249 | 50.49% 87.24% | 100 pmol/10e6 cells 1 nmol/10e6 cells |
| 5'-(Cholesteryl-TEG)2-PEG2000-Fluos-Biotin_TEG-3' INVERS | purified | 29.891250 | 48.66% 81.29% | 100 pmol/10e6 cells 1 nmol/10e6 cells |
| 5'-(Cholesteryl-TEG)2-Spacer C18-dT-Biotin_TEG-3' INVERS | purified | 29.891252 | 28.18% 61.88% | 100 pmol/10e6 cells 1 nmol/10e6 cells |
| 5'-(Cholesteryl-TEG)2-Spacer C12-dT-Biotin_TEG-3' INVERS | purified | 29.891253 | 71.41% 86.21% | 100 pmol/10e6 cells 1 nmol/10e6 cells |

B)

| Molecule/combination thereof tested | Internal number | Recovery rate treated cells (SA-plate) | Recovery rate untreated cells (SA plate) | Recovery rate treated cells (untreated-plate) | Recovery rate untreated cells (ntreated plate) | Remarks |
|---|---|---|---|---|---|---|
| Cholesterol- Compound (5'-XXYFZ-3') | 29.891180 | 73.2% | 16.3% | 56.7% | 68.7% | strong staining |
| Boronic acid- Compound (single) | 15.260267 | 16.3% | 13.0% | 32.5% | 41.3% | |
| Cholesterol- Compound (5'-XXYFZ-3') | 29.891180 | 71.7% | 24.4% | | | |
| Distearoyl- Compound (Avanti) | | 53.8% | | | | |
| Chol-Compound + Distearoyl-Compound | 29.891180 | 74.7% | | | | |
| Cholesterol- Compound (5'-XXYFZ-3') | 29.891180 | 83.2% | 30.6% | | | |
| Distearoyl- compound (Avanti) | | 66.7% | | | | |
| Chol-Compound + Distearoyl-Compound | 29.891180 | 80.2% | | | | |
| Cholesterol- Compound 200 µl Zellsus. | 29.891180 | 67.6%/71.9% | | | | |
| Cholesterol- Compound 400 µl Zellsus. | 29.891180 | 78.4%/84.1% | | | | |
| Cholesterol- Compound 800 µl Zellsus. | 29.891180 | 81.1%/86.4% | | | | |
| Cholesterol- Compound (5'-XXYFZ-3') | 29.891180 | 80.9% | 30.8% | | | |
| Distearoyl- Compound (Avanti) | | 50.6% | | | | |
| Chol-Compound + Distearoyl-Compound | 29.891180 | 77.8% | | | | |
| Myristic acid-Compound (5'-XXYFZ-3')C1 | 29.891194 | 20.7% | 21.6% | | | weak Staining |
| Myristic acid-Compound (5'-XXYFZ-3')C2 | 29.891194 | 22.1% | | | | |
| Myristic acid-Compound (5'-XXYFZ-3')C1 | 29.891194 | 33.1% | 19.5% | | | stronger Staining |
| Myristic acid-Compound (C14-Lys-PEG) | 15.260268 | 47.7% | 19.5% | | | |
| Cholesterol- Compound (5'-XXYFZ-3') | 29.891194 | 63.4% | 10.7% | | | |
| Myristic acid-Compound (C14-Lys-PEG) | 15.260268 | 53.9% | | | | |
| Chol-Compound + Myr.-Compound | 29.891194/15.260268 | 43.6% | | | | |
| Chol-Compound + Myr.-Compound | 29.891194/15.260268 | 43.6% | | | | |
| Chol-Compound 2.16 µg/2 × 10e6 WBCs | 29.891180 | 78.6% | | | | |
| Chol-Compound 21.6 µg/2 × 10e6 WBCs | 29.891180 | 68.6% | | | | |
| Chol-Compound 216 µg/2 × 10e6 WBCs | 29.891180 | 50.1% | | | | |
| Myr-Compound 2.16 µg/2 × 10e6 WBCs | 15.260268 | 39.6% | | | | higher conc. will be tested again |
| Myr-Compound 21.6 µg/2 × 10e6 WBCs | 15.260268 | 46.7% | | | | |
| Myr-Compound 216 µg/2 × 10e6 WBCs | 15.260268 | 51.8% | | | | |
| Cholesterol- Compound (5'-XXYFZ-3') | 29.891194 | 89.6% | | | | |
| Distearoyl- Compound (Avanti) | | 82.6% | | | | |
| Myristic acid.-Compound (C14-Lys-PEG) | 15.260268 | 85.7% | | | | |
| Chol-Compound + Distearoyl-Compound | 29.891194 | 84.3% | | | | |

| | | |
|---|---|---|
| Chol-Compound + Myr.-Compound | 29.891194/15.260268 | 91.3% |
| Chol + Distearoyl + Myr | 29.891194/15.260268 | 87.0% |
| Cholesterol- Compound (5'-XXYFZ-3') | 29.891194 | 74.0% |
| Distearoyl- Compound (Avanti) | | 53.5% |
| Myristic acid.-Compound (C14-Lys-PEG) | 15.260268 | 45.6% |
| Chol-Compound + Distearoyl-Compound | 29.891194 | 71.7% |
| Chol-Compound + Myr.-Compound | 29.891194/15.260268 | 68.4% |
| Chol + Distearoyl + Myr | 29.891194/15.260268 | 64.9% |
| Chol- Compound 10 min 4° C. | 29.891194 | 81.6% |
| Chol- Compound 60 min 4° C. | 29.891194 | 81.7% |
| Chol- Compound 10 min RT | 29.891194 | 88.3% |
| Chol- Compound 60 min RT | 29.891194 | 85.5% |
| Chol- Compound 10e4 MDAs in WBCs | 29.891194 | 99.0% |
| Chol- Compound 5 × 10e5 WBCs | 29.891194 | 70.0% |
| Chol- Compound 20e3 MDAs in WBCs | 29.891194 | 102.0% |
| Chol- Compound 5 × 10e5 WBCs | 29.891194 | 70.8% |
| Chol- Compound 40e3 MDAs in WBCs | 29.891194 | 102.0% |
| Chol- Compound 10e6 WBCs | 29.891194 | 69.4% |
| Myr-Myr-C18-Fluos | 29.891213 | 67.4% | strong staining |
| Myr-Myr-PEG-Fluos | 29.891194 | 24.4% | weak staining |
| Myr-Myr-7xC18-Fluos | 29.891214 | 78.9% | strong staining |
| Myr-C9-Myr-PEG-Fluos | 29.891197 | not enough material | weak staining |

C) Comparison of Results Obtained Upon Pretreatment of Either the Wells of the Plate or the Cells with Molecules of the Invention The experiments were performed for different incubation times, as shown below:

| Well | | MW | Standard deviation | Mean % | Standard deviation % |
|---|---|---|---|---|---|
| 30 min target: 300.000 WBC | | | | | |
| a1 | Well treated | 61470 | | 21.64 | 2.71 |
| a2 | Well treated | 67259 | | | |
| a3 | Well treated | 74951 | | | |
| a4 | Well treated | 55956 | 64909 | 8131.2 | |
| b1 | untreated | 55575 | | 9.69 | 6.56 |
| b2 | untreated | 32017 | | | |
| b3 | untreated | 17166 | | | |
| b4 | untreated | 11481 | 29059.75 | 19683.1 | |
| c1 | WBC treated | 213072 | | 77.28 | 4.39 |
| c2 | WBC treated | 237475 | | | |
| c3 | WBC treated | 243445 | | | |
| c4 | WBC treated | 233327 | 231829.75 | 13176.7 | |
| 90 min target: 300.000 WBC | | | | | |
| a1 | Well treated | 124492 | | 47.62 | 4.33 |
| a2 | Well treated | 143548 | | | |
| a3 | Well treated | 154212 | | | |
| a4 | Well treated | 149208 | 142865 | 13000.28 | |
| b1 | untreated | 46601 | | 9.32 | 4.58 |
| b2 | untreated | 29206 | | | |
| b3 | untreated | 21199 | | | |
| b4 | untreated | 14882 | 27972 | 13732.98 | |
| c1 | WBC treated | 237185 | | 83.12 | 2.72 |
| c2 | WBC treated | 252944 | | | |
| c3 | WBC treated | 254697 | | | |
| c4 | WBC treated | 252559 | 249346.25 | 8160.72 | |
| 120 min target: 300.000 WBC | | | | | |
| a1 | Well treated | 167671 | | 57.02 | 6.37 |
| a2 | Well treated | 177678 | | | |
| a3 | Well treated | 192194 | | | |
| a4 | Well treated | 146708 | 171062.75 | 19104.5 | |
| b1 | untreated | 46402 | | 9.74 | 4.88 |
| b2 | untreated | 35669 | | | |
| b3 | untreated | 20989 | | | |
| b4 | untreated | 13798 | 29214.5 | 14633.3 | |
| c1 | WBC treated | 256949 | | 86.23 | 2.43 |
| c2 | WBC treated | 268552 | | | |
| c3 | WBC treated | 258291 | | | |
| c4 | WBC treated | 250979 | 258692.75 | 7300.9 | |

The results on immobilization are summarized as follows:

|  | 30 min | | 90 min | | 120 min | |
|---|---|---|---|---|---|---|
|  | WBC recovery rate [%] | Standard deviation | WBC recovery rate [%] | Standard deviation | WBC recovery rate [%] | Standard deviation |
| molecule of invention bound to surface | 21.64 | 2.71 | 47.6 | 4.33 | 57.02 | 6.37 |
| molecule of invention + cells | 77.28 | 4.39 | 83.1 | 2.72 | 86.23 | 2.43 |
| untreated | 9.69 | 6.56 | 9.3 | 4.58 | 9.74 | 4.88 |

|  | 30 min | 90 min | 120 min |
|---|---|---|---|
| molecule of invention bound to surface | 21.64 | 47.6 | 57.02 |
| molecule of invention + cells | 77.28 | 83.1 | 86.23 |
| untreated | 9.69 | 9.3 | 9.74 |

D) Determination of Recovery Rate for Exemplary Compound Biotin-PEG-lys-(C14)2:

The following recovery rate was determined for compound Biotin-PEG-lys-(C14)2:

M=2708.90 g/mol 5.4 mg/10 ml EtOH c=n/V=m/M*V c=5.4 g/(2708.9 g/mol*10 l)=1.99 10e-4 mol/l 1.99*10e-4 mol/l=7.96 nmol/4 µl 4 µl=4.5*10e6 Cells →1.77 nmol/10e6 Cells Recovery rate in this experiment: 85.72%

Example 4: Comparison of Compounds of the Invention Containing One vs. Two Hydrophobic Moieties Aim of this experiment: Testing of the white blood cell immobilization on a streptavidin-coated surface using different molecules of the invention. In particular, the performance of a single cholesterol-molecule and different dual-linker molecules (i.e. containing two hydrophobic moieties) was tested. In detail, immobilization of white blood cells (WBCs) on a Streptavidin-coated surface using different linker molecules was tested on a 12-well plate: 300 000 WBCs/well. This was followed by the measurement of the cell recovery rate after immobilization and washing of the cells using the Cellavista instrument (10× Nuclei Operator s9s5).

| Molecule tested | Characteristics | Internal No | Structure |
|---|---|---|---|
| 5'-(Cholesterol-TEG)1-Doubler-dT-Biotin-3' | Mono-linker | 29.891272 | 5'-Y\\XZ-3' / 5'-/ <br> Y = Cholesteryl-TEG <br> X = Doubler <br> Z = dTBiotin |
| 5'-(Cholesteryl-TEG)2-Spacer C12-dT-Biotin_TEG-3' INVERS | Dual linker | 29.891253 | 3'-YYXTZ-5' <br> Y = Cholesteryl-TEG <br> X = Spacer C12 <br> Z = Biotin-TEG |
| 5'-(Cholesteryl-TEG)2-Spacer C18-Fluos-Biotin_TEG-3' INVERS | Dual linker | 29.891254 | 3'-YYXWZ-5' <br> Y = Cholesteryl-TEG <br> X = Spacer C18 <br> W = Fluorescein <br> Z = Biotin-TEG |

The results are as follows:
Sample 1

| compound internal reference No. | | Mean standard deviation | Recovery rate | standard deviation |
|---|---|---|---|---|
| A1 | 29.891253 | 105061 | 17632.25 | 41.44% | 5.88% |
| B1 | 29.891253 | 128195 | | | |
| C1 | 29.891253 | 139678 | | | |
| A2 | 29.891254 | 157660 | 16339.42 | 57.63% | 5.45% |
| B2 | 29.891254 | 190148 | | | |
| C2 | 29.891254 | 170850 | | | |
| A3 | 29.891272 | 147132 | 19366.19 | 56.49% | 6.46% |
| B3 | 29.891272 | 179643 | | | |
| C3 | 29.891272 | 181620 | | | |
| A1 | 29.891253 | 218861 | 6689.53 | 72.13% | 2.23% |
| B1 | 29.891253 | 221471 | | | |
| C1 | 29.891253 | 208802 | | | |
| A2 | 29.891254 | 244649 | 13351.64 | 82.19% | 4.45% |
| B2 | 29.891254 | 234262 | | | |
| C2 | 29.891254 | 260760 | | | |
| A3 | 29.891272 | 199973 | 14735.92 | 72.13% | 4.91% |
| B3 | 29.891272 | 220701 | | | |
| C3 | 29.891272 | 228481 | | | | compound concentration: 1 nmol/10e6 WBCs

Sample 2

| compound internal reference No. | Mean | Mean standard deviation | Recovery rate | standard deviation |
|---|---|---|---|---|
| A) compound concentration: 100 pmol/10e6 WBCs | | | | |
| A1 29.891253 | 178919 | | 62.59% | 3.04% |
| B1 29.891253 | 197130 | | | |
| C1 29.891253 | 187224 | 187757.67 | 9117.22 | |
| A2 29.891254 | 185100 | | 65.69% | 3.58% |
| B2 29.891254 | 200184 | | | |
| C2 29.891254 | 205917 | 197067.00 | 10752.84 | |
| A3 29.891272 | 161504 | | 62.11% | 7.22% |
| B3 29.891272 | 201424 | | | |
| C3 29.891272 | 196021 | 186316.33 | 21657.26 | |
| B) compound concentration: 1 nmol/10e6 WBCs | | | | |
| A1 29.891253 | 239105 | | 79.02% | 1.65% |
| B1 29.891253 | 240632 | | | |
| C1 29.891253 | 231420 | 237052.33 | 4937.14 | |
| A2 29.891254 | 244396 | | 81.79% | 0.59% |
| B2 29.891254 | 244304 | | | |
| C2 29.891254 | 247428 | 245376.00 | 1777.68 | |
| A3 29.891272 | 241232 | | 82.47% | 2.31% |
| B3 29.891272 | 254894 | | | |
| C3 29.891272 | 246129 | 247418.33 | 6921.66 | |

Conclusion: The Cholesterol-mono linker molecule (i.e. a compound containing a single hydrophobic moiety cholesterol) shows similar cell immobilization characteristics compared dual linker molecules (i.e. compounds containing two hydrophobic moieties).

Example 5: Stabilization of Cells Using Compounds of the Invention

The effect of compounds of the invention on stabilizing cells and on immobilization was determined.

Figure 14:
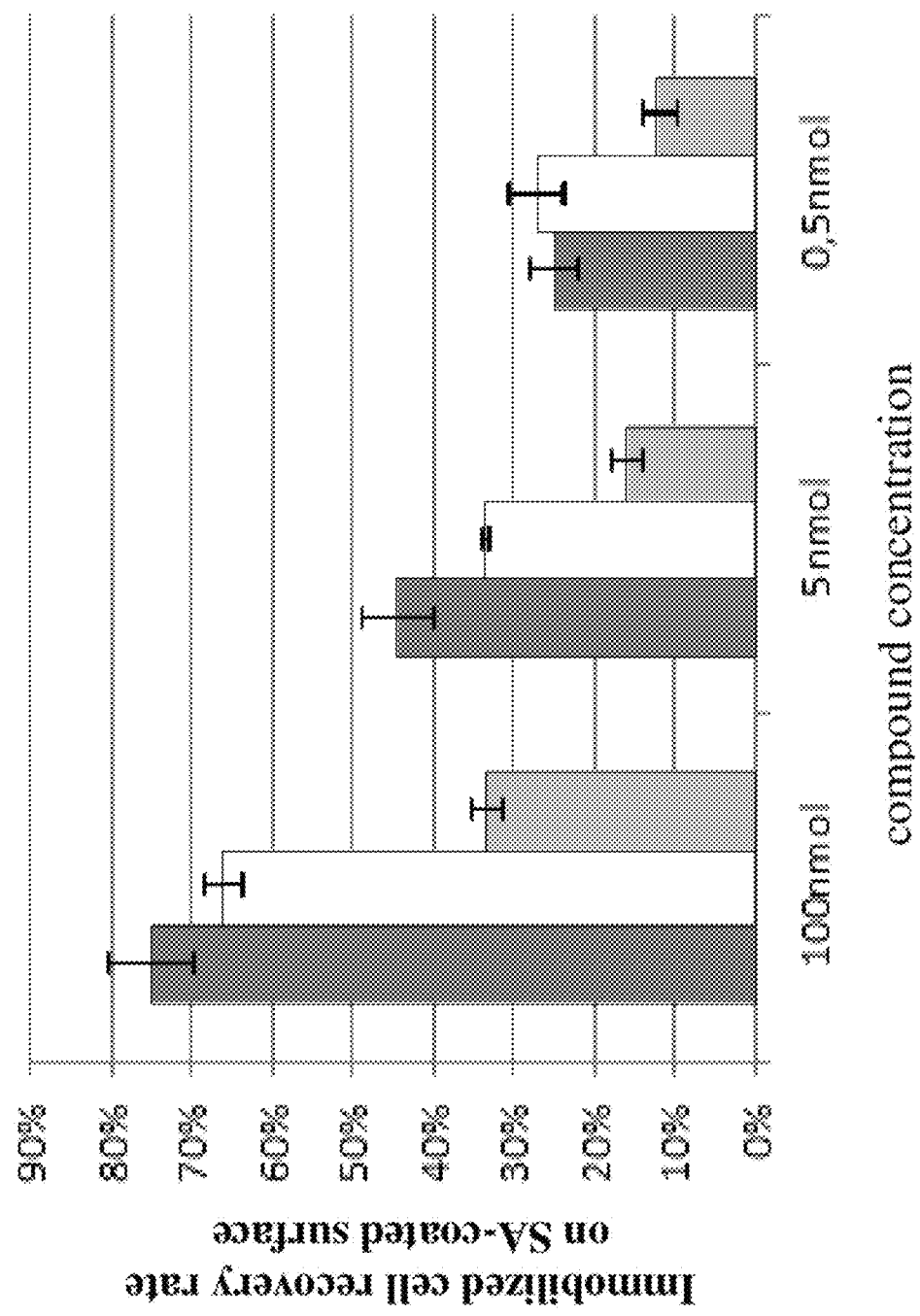
FIG. 14: shows WBC recovery rate after centrifugation and cell immobilization using different molecules. Molecule probes HH1749*, HH1750* and HH1755* show different performance concerning cell immobilization rate at different concentrations. The higher the compound concentration, the higher the cell immobilisation rate.
Figure 15:
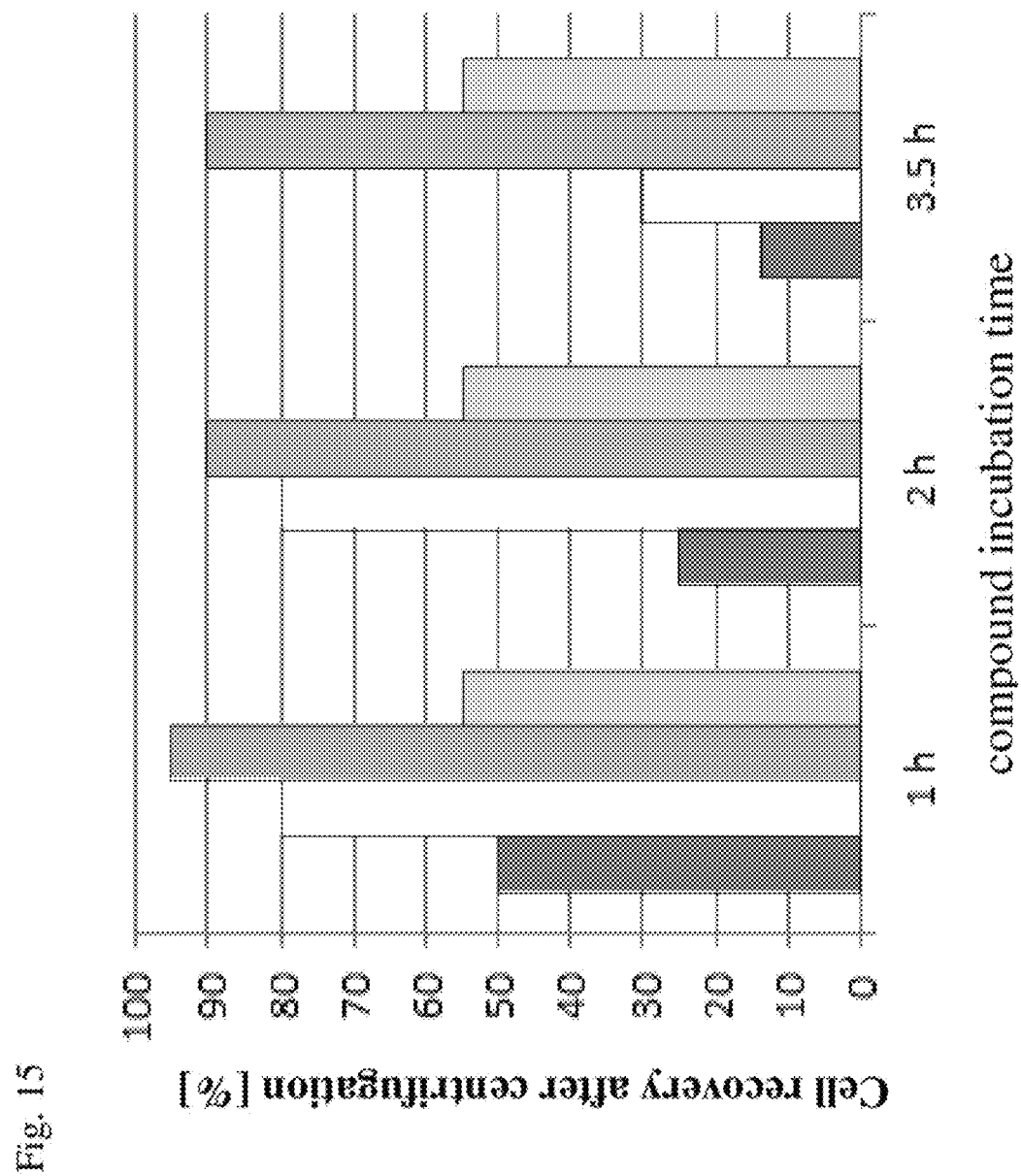
FIG. 15: shows WBC recovery rate after centrifugation using different compounds at different points of time. Molecules A and B (A: Cholesteryl-TEG-Cholesteryl-TEG-(SpacerC18)7-Fluos-Biotin-TEG; B: Biotin-PEG-Lysin-(C18)2) show different performance concerning recovery rate after centrifugation. Respective left column: w/o compound of invention; respective second column from left: 0.35 nmol molecule A; respective third column from left: 100 nmol molecule B; respective right column: 0.5 nmol molecule B. The higher the molecule concentration, the higher the cell recovery rate after centrifugation. Molecule B enables cell immobilization within 3.5 hours. Centrifugation characteristics: 10 min, 300×g.

A) WBC Recovery Rate After Centrifugation and Cell Immobilization Using Different Molecules As shown in FIG. 14, molecule probes HH1749*, HH1750* and HH1755* (* Biotin-PEG-Lysin-(C18)2) show different performance concerning recovery rate after centrifugation: The higher the concentration of the molecule, the higher the cell recovery rate after centrifugation. Centrifugation characteristics: 10 min, 300×g. As can be seen from FIG. 15, molecule probes HH1749*, HH1750* and HH1755* show different performance concerning cell immobilization rate at different concentrations. The higher the linker concentration, the higher the cell immobilisation rate.

Figure 16:
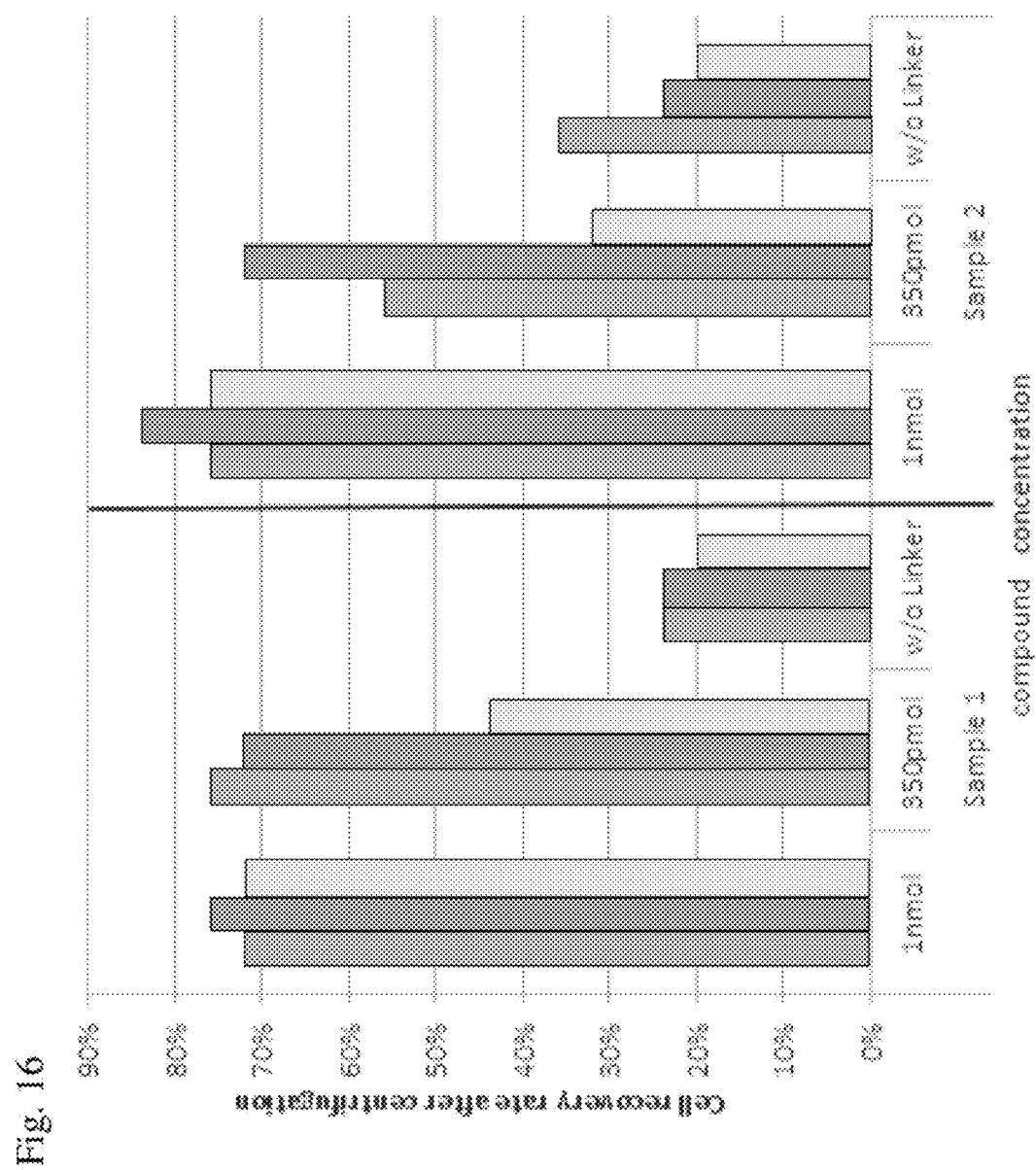
FIG. 16: shows WBC recovery rate after centrifugation with different experimenters. The respective left, middle and right columns per assay represent different Experimenters 1, 2 and 3. The higher the molecule concentration, the higher the cell recovery rate after centrifugation. Moreover, cell stabilization is independent on the experimenter. Centrifugation characteristics: 10 min, 300×g. Molecule: Cholesteryl-TEG-Cholesteryl-TEG-(SpacerC18)7-Fluos-Biotin-TEG.

B) WBC Recovery Rate After Centrifugation Using Different Linkers—Different Points of Time As can be seen from FIG. 16, molecules A and B (A: Cholesteryl-TEG-Cholesteryl-TEG-(SpacerC18)7-Fluos-Biotin-TEG; B: Biotin-PEG-Lysin-(C18)2) show different performance concerning recovery rate after centrifugation. The higher the molecule concentration, the higher the cell recovery rate after centrifugation. Molecule B enables cell immobilization within 3.5 hours. Centrifugation characteristics: 10 min, 300×g. A: Choleseryl-TEG-Cholesteryl-TEG-(SpacerC18)7-Fluos-Biotin-TEG. B: Biotin-PEG-Lysin-(C18)2

C) WBC Recovery Rate After Centrifugation—Fifferent Experimenters

Figure 17:
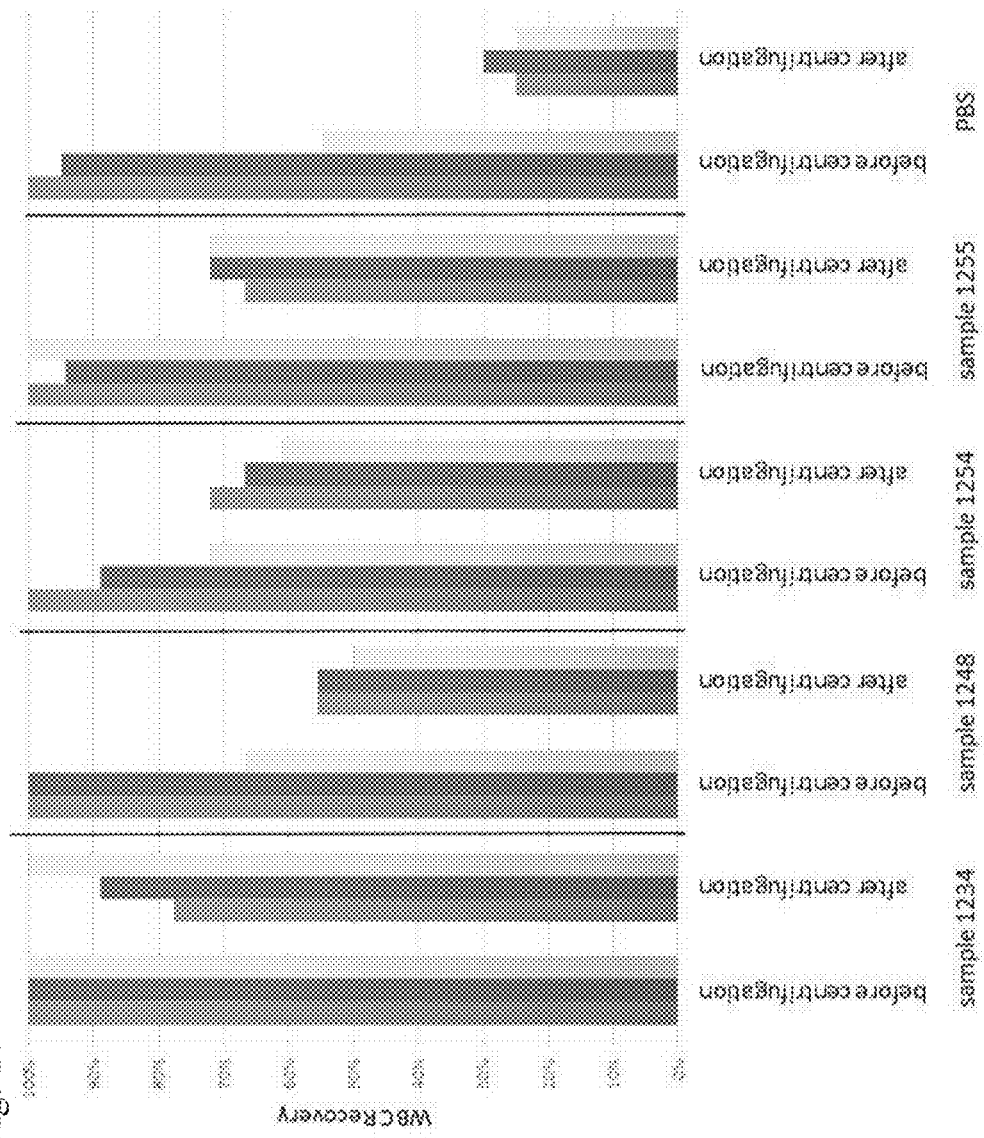
FIG. 17: shows WBC recovery rate after centrifugation at different points of time and centrifugation settings. Following molecules were tested: 1234: 5'-(Cholesteryl-TEG)2-Spacer C18-dT-Biotin-TEG-3'; 1248: 3'-(Cholesteryl-TEG)2-PEG2000-Fluos-Biotin-TEG-5' INVERS; 1254: 3'-(Cholesteryl-TEG)2-SpacerC18-Fluos-Biotin-TEG-5' INVERS; 1255: 3'-(Myristic acid)2-PEG2000-dT-Biotin-TEG-5' INVERS. All molecules enable cell immobilization within 2 hours. WBCs in PBS are damaged during centrifugation at 300×g for 20 min. Molecule1234 shows the best performance followed by compound 1255 and 1254. Centrifugation characteristics: 20 min, 300×g. Respective left column: 10 min incubation with molecule. Respective middle column: 1 h min incubation with molecule. Respective right column: 2 h incubation with molecule.

As can be seen from FIG. 17, the higher the molecule concentration, the higher the cell recovery rate after centrifugation. Moreover, cell stabilization is independent on the experimenter. Centrifugation characteristics: 10 min, 300×g. Molecule: Cholesteryl-TEG-Cholesteryl-TEG-(SpacerC18)7-Fluos-Biotin-TEG.

Figure 18:
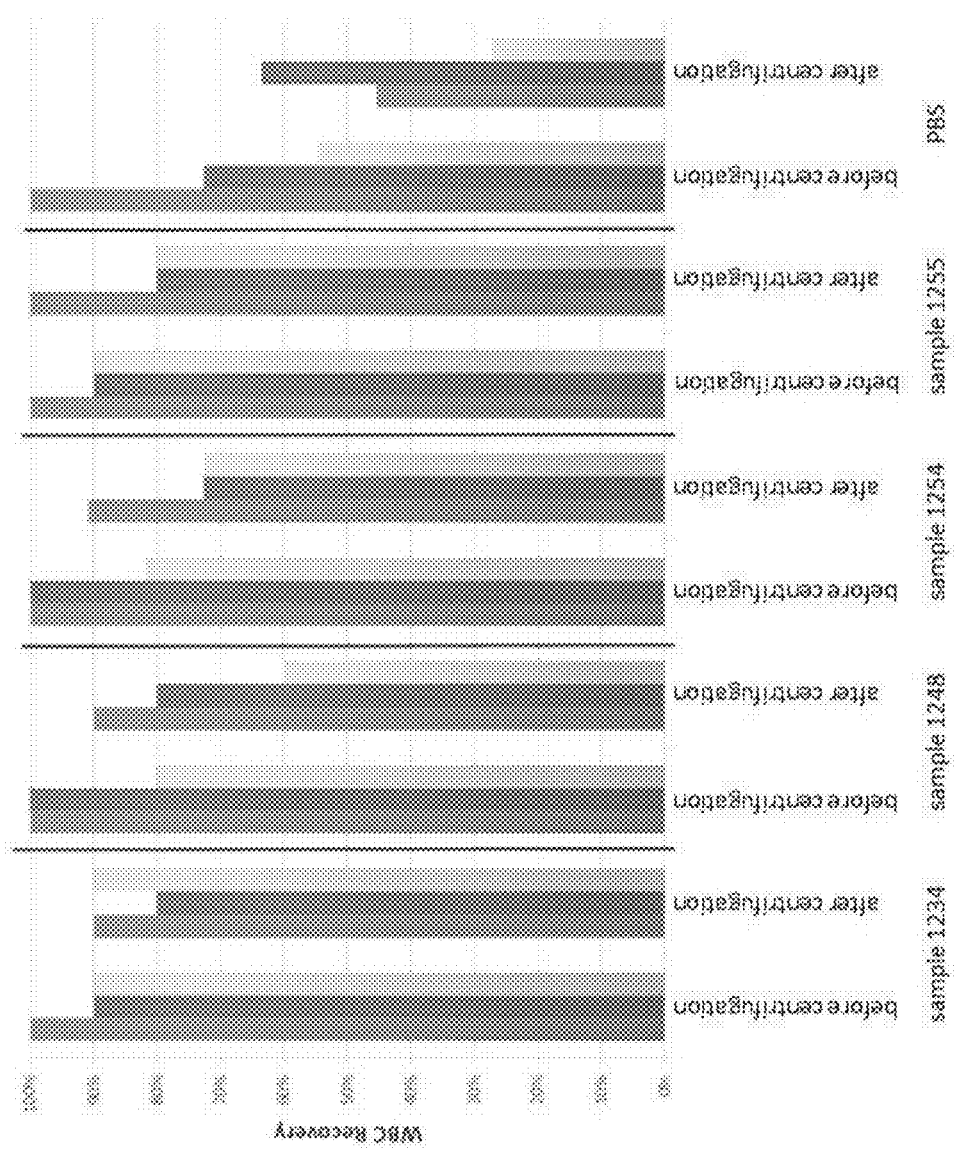
FIG. 18: shows WBC recovery rate after centrifugation at different points of time and centrifugation settings. Following molecules were tested: 1255: 3'-(Myristic acid)2-PEG2000-dT-Biotin-TEG-5' INVERS; 1234: 5'-(Cholesteryl-TEG)2-Spacer C18-dT-Biotin-TEG-3'; 1248: 3'-(Cholesteryl-TEG)2-PEG2000-Fluos-Biotin-TEG-5' INVERS; 1254: 3'-(Cholesteryl-TEG)2-SpacerC18-Fluos-Biotin-TEG-5' INVERS. All molecules enable cell immobilization within 2 hours. WBCs in PBS are damaged during centrifugation at 500×g for 20 min. Molecule 1234 shows the best performance followed by molecule 1255 and 1254. Centrifugation characteristics: 20 min, 500×g. Respective left column: 10 min incubation with molecule. Respective middle column: 1 h min incubation with molecule. Respective right column: 3 h incubation with molecule.

D) WBC Recovery Rate After Centrifugation—Different Points of Time and Centrifugation Settings The results of the first experiment are shown in FIG. 18. Following molecules were tested:

1234: 5'-(Cholesteryl-TEG)2-Spacer C18-dT-Biotin-TEG-3'

1248: 3'-(Cholesteryl-TEG)2-PEG2000-Fluos-Biotin-TEG-5' INVERS 1254: 3'-(Cholesteryl-TEG)2-SpacerC18-Fluos-Biotin-TEG-5' INVERS 1255: 3'-(Myristic acid)2-PEG2000-dT-Biotin-TEG-5' INVERS All molecules enable cell immobilization within 2 hours
WBCs in PBS are damaged during centrifugation at 300×g for 20 min
Molecule1234 shows the best performance followed by compound 1255 and 1254
Centrifugation characteristics: 20 min, 300×g.

Figure 19:
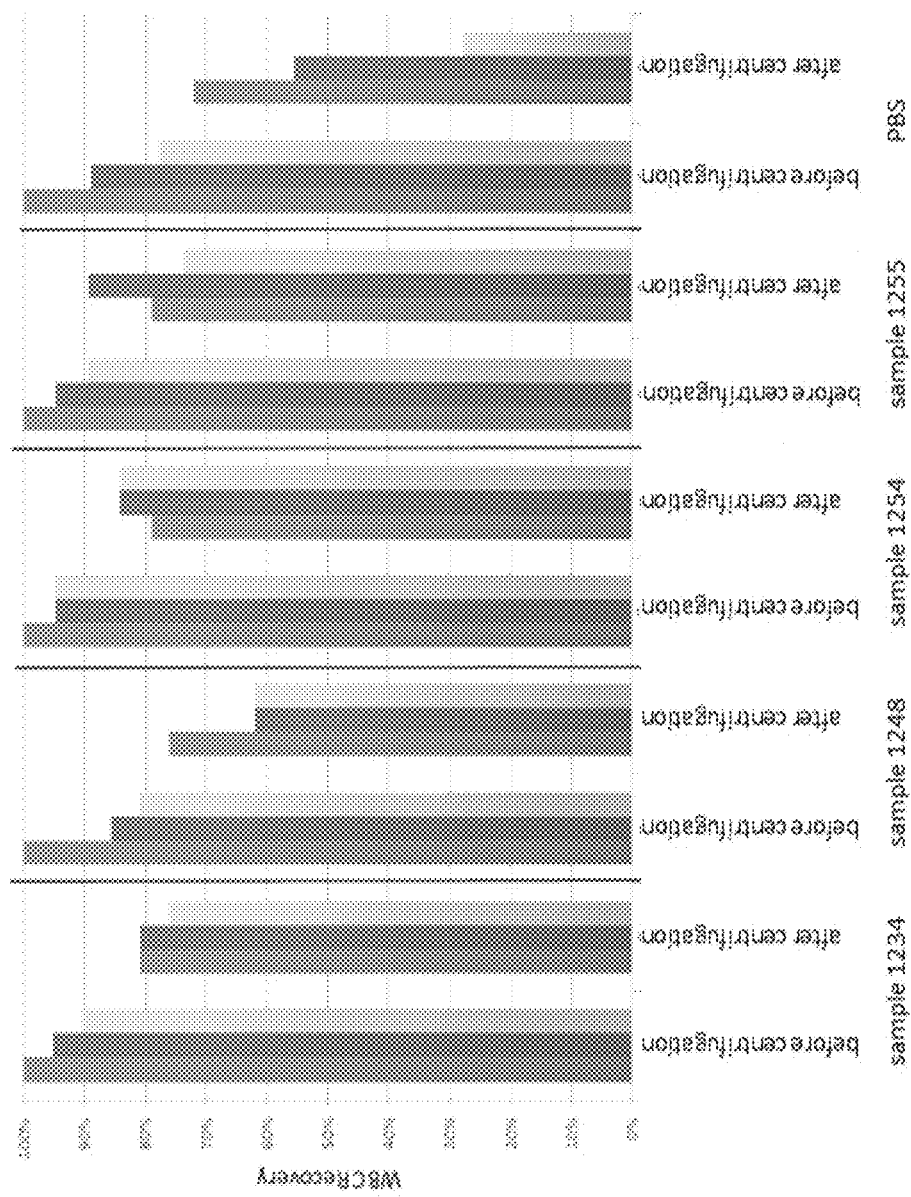
FIG. 19: shows WBC recovery rate after centrifugation at different points of time and centrifugation settings. Following molecules were tested: 1255: 3'-(Myristic acid)2-PEG2000-dT-Biotin-TEG-5' INVERS; 1234: 5'-(Cholesteryl-TEG)2-Spacer C18-dT-Biotin-TEG-3'; 1248: 3'-(Cholesteryl-TEG)2-PEG2000-Fluos-Biotin-TEG-5' INVERS; 1254: 3'-(Cholesteryl-TEG)2-SpacerC18-Fluos-Biotin-TEG-5' INVERS. All molecules enable cell immobilization within 2 hours. WBCs in PBS are damaged during centrifugation at 1000×g for 20 min. Centrifugation characteristics: 20 min, 1000×g. Respective left column: 10 min incubation with molecule. Respective middle column: 1 h min incubation with molecule. Respective right column: 2 h incubation with molecule.

The results of the second experiment in this context are shown in FIG. 19. Following molecules were tested:

1255: 3'-(Myristic acid)2-PEG2000-dT-Biotin-TEG-5' INVERS 1234: 5'-(Cholesteryl-TEG)2-Spacer C18-dT-Biotin-TEG-3'

1248: 3'-(Cholesteryl-TEG)2-PEG2000-Fluos-Biotin-TEG-5' INVERS

1254: 3'-(Cholesteryl-TEG)2-SpacerC18-Fluos-Biotin-TEG-5' INVERS

Figure 20:
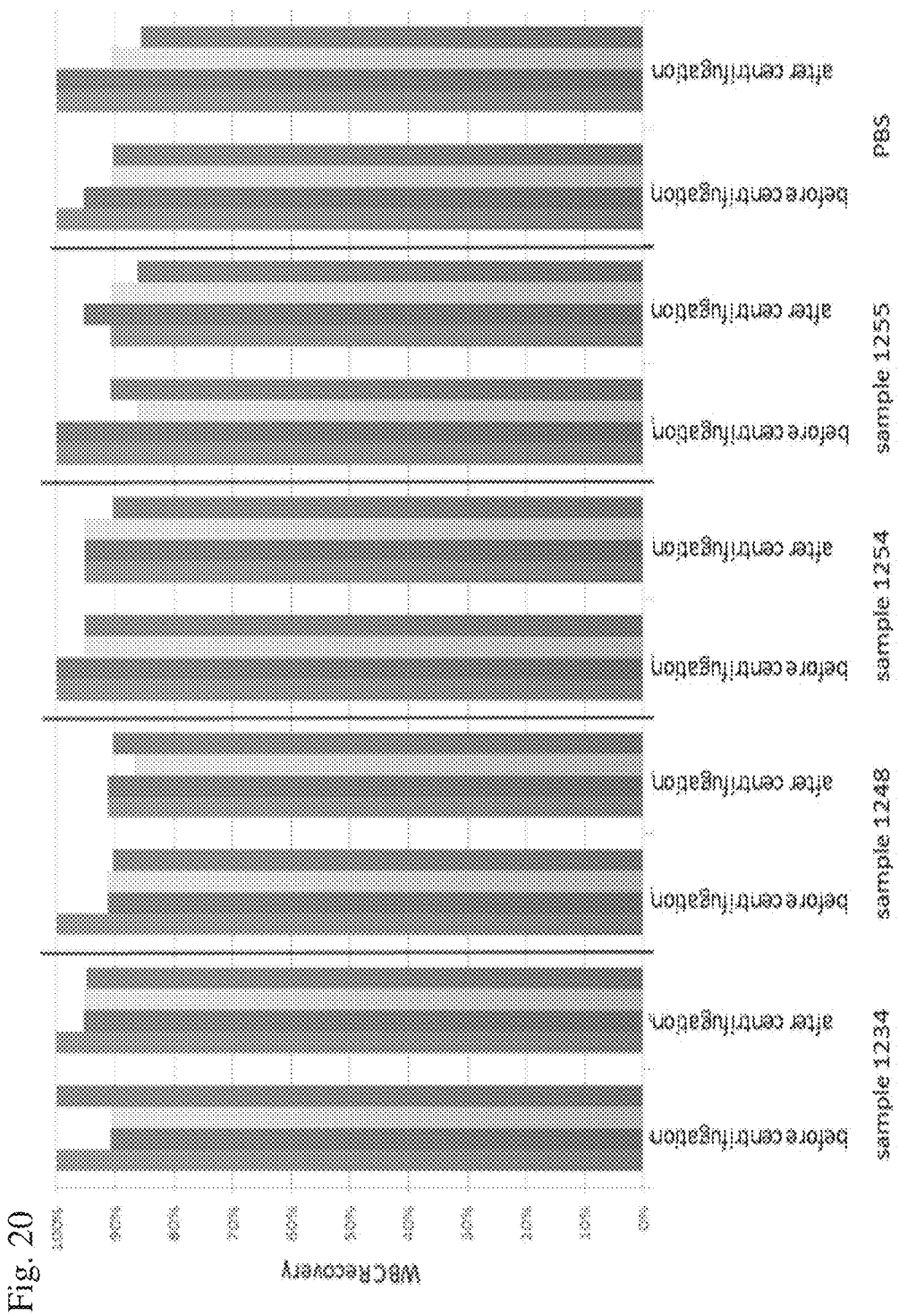
FIG. 20: shows Jurkat cell recovery rate after centrifugation at different points of time. Respective columns from left: 1: 10 min incubation with molecule. 2: 1 h incubation with molecule. 3: 3,5 h incubation with molecule. 4: 5.5 h min incubation with molecule. Following molecules were tested: 1255: 3'-(Myristic acid)2-PEG2000-dT-Biotin-TEG-5' INVERS. 1234: 5'-(Cholesteryl-TEG)2-Spacer C18-dT-Biotin-TEG-3'; 1248: 3'-(Cholesteryl-TEG)2-PEG2000-Fluos-Biotin-TEG-5' INVERS; 1254: 3'-(Cholesteryl-TEG)2-SpacerC18-Fluos-Biotin-TEG-5' INVERS. Jurkat culture cells are stable during centrifugation processes in PBS as well as using different molecules within 5.5 h. Centrifugation characteristics: 20 min, 500×g.

The results are as follows:

All molecules enable cell immobilization within 2 hours
WBCs in PBS are damaged during centrifugation at 500×g for 20 min
Molecule 1234 shows the best performance followed by molecule 1255 and 1254 Centrifugation characteristics: 20 min, 500×g. The results of the third experiment in this context are shown in FIG. 20. Following molecules were tested:

1255: 3'-(Myristic acid)2-PEG2000-dT-Biotin-TEG-5' INVERS

1234: 5'-(Cholesteryl-TEG)2-Spacer C18-dT-Biotin-TEG-3'

1248: 3'-(Cholesteryl-TEG)2-PEG2000-Fluos-Biotin-TEG-5' INVERS

1254: 3'-(Cholesteryl-TEG)2-SpacerC18-Fluos-Biotin-TEG-5' INVERS

The results are as follows:

All molecules enable cell immobilization within 2 hours

WBCs in PBS are damaged during centrifugation at 1000×g for 20 min

Centrifugation characteristics: 20 min, 500×g.

E) Jurkat Recovery Rate After Centrifugation—Different Points of Time

Figure 21A:
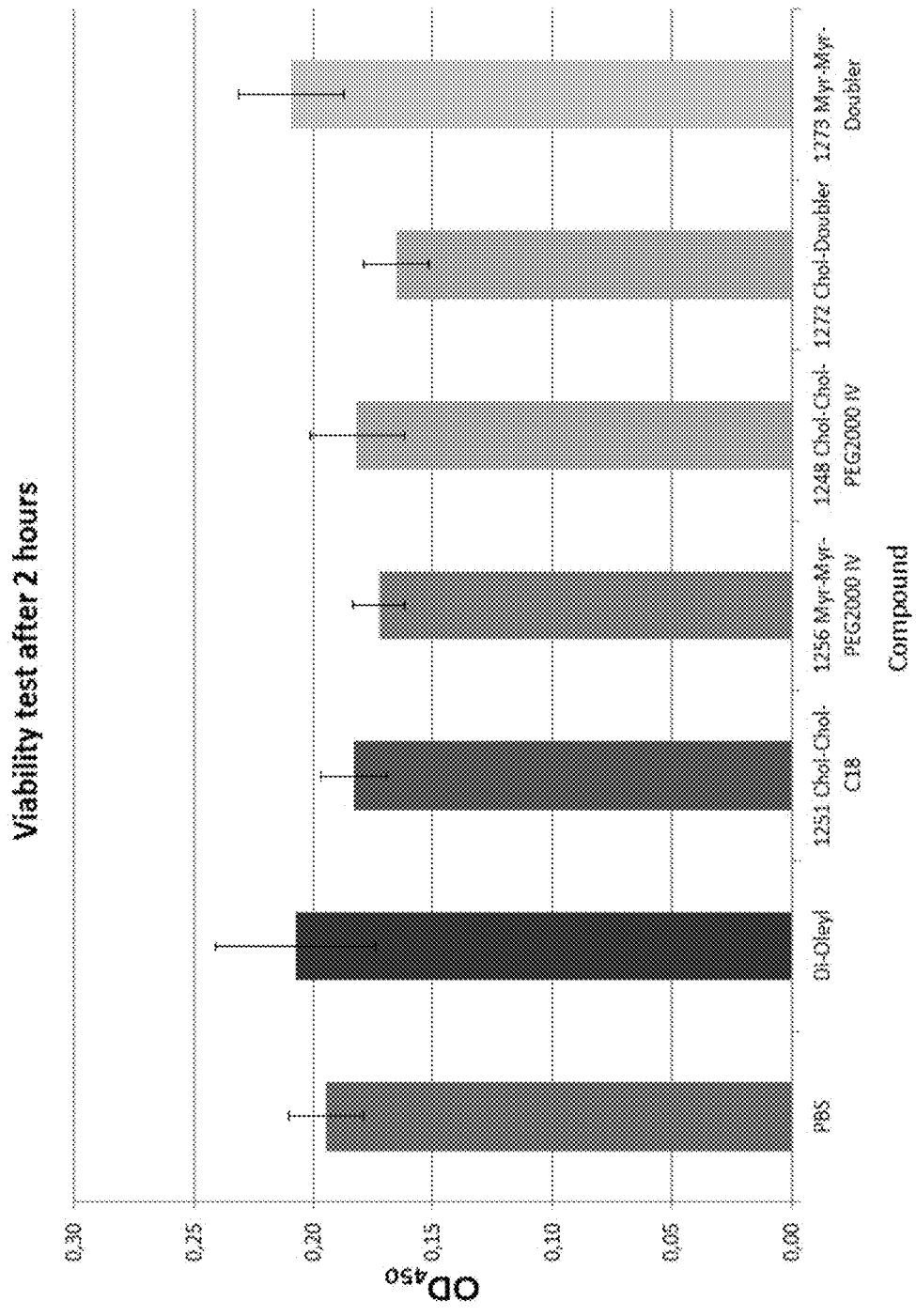
FIG. 21A: shows that tri-functional linker moieties do not influence cell viability. Cell viability test using WST-1 proliferation kit (RAS) was performed, employing different compounds for use according to the invention differing in the trifunctional linker moieties. The different linkers appear not to influence the cell viability during linker incubation time of 4 hours. Viability test after 2 hours.
Figure 21B:
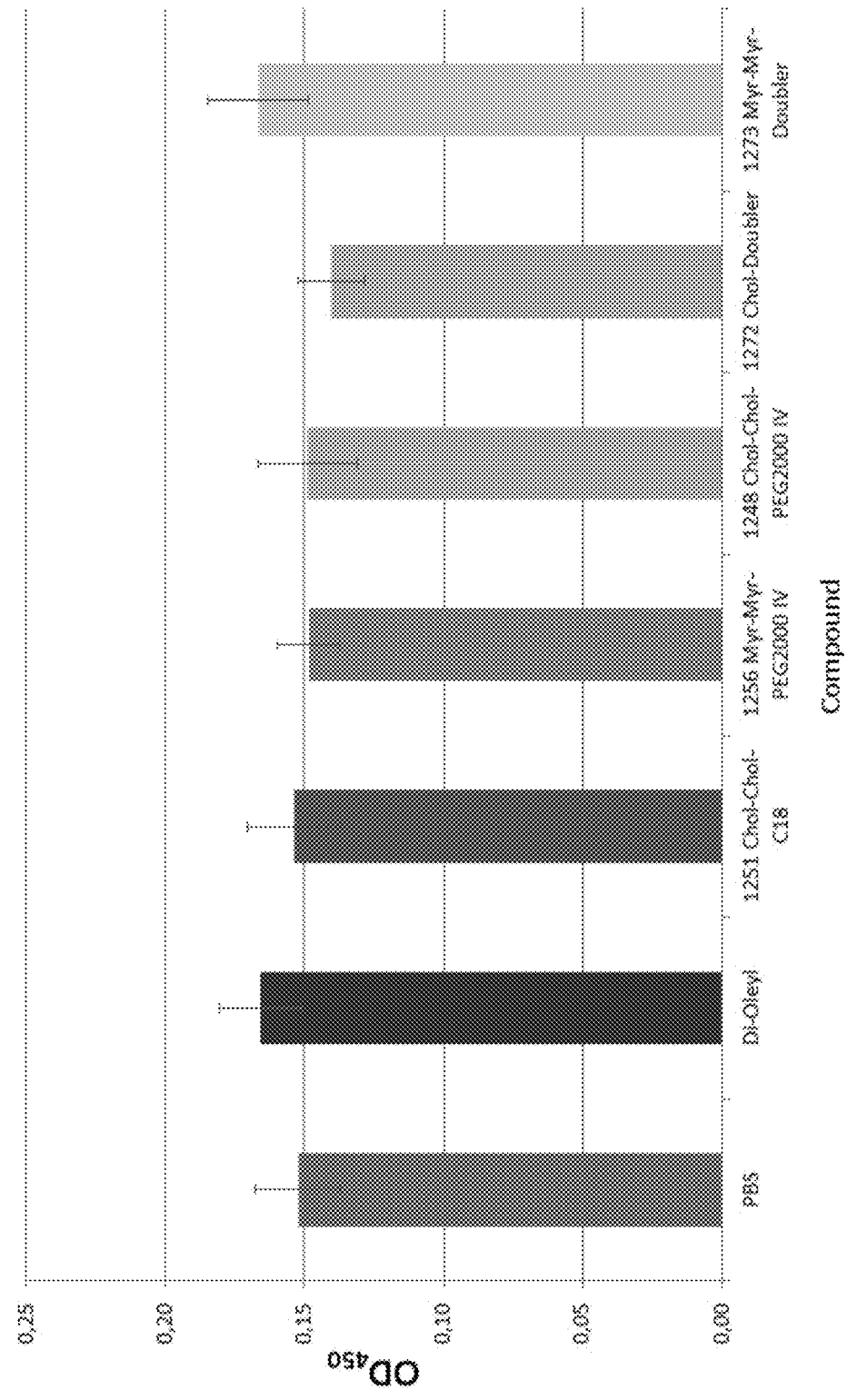
FIG. 21B: shows that tri-functional linker moieties do not influence cell viability. Cell viability test using WST-1 proliferation kit (RAS) was performed, employing different compounds for use according to the invention differing in the trifunctional linker moieties. The different linkers appear not to influence the cell viability during linker incubation time of 4 hours. Viability test after 4 hours.

The results of this experiment are shown in FIG. 21. Following molecules were tested:

1255: 3'-(Myristic acid)2-PEG2000-dT-Biotin-TEG-5' INVERS

1234: 5'-(Cholesteryl-TEG)2-Spacer C18-dT-Biotin-TEG-3'

1248: 3'-(Cholesteryl-TEG)2-PEG2000-Fluos-Biotin-TEG-5' INVERS

1254: 3'-(Cholesteryl-TEG)2-SpacerC18-Fluos-Biotin-TEG-5' INVERS

The results are as follows:

Jurkat culture cells are stable during centrifugation processes in PBS as well as using different molecules within 5.5 h.

Centrifugation characteristics: 20 min, 500×g.

F) Tri-Functional Linker Moieties Do Not Influence Cell Viability

Figure 22A:
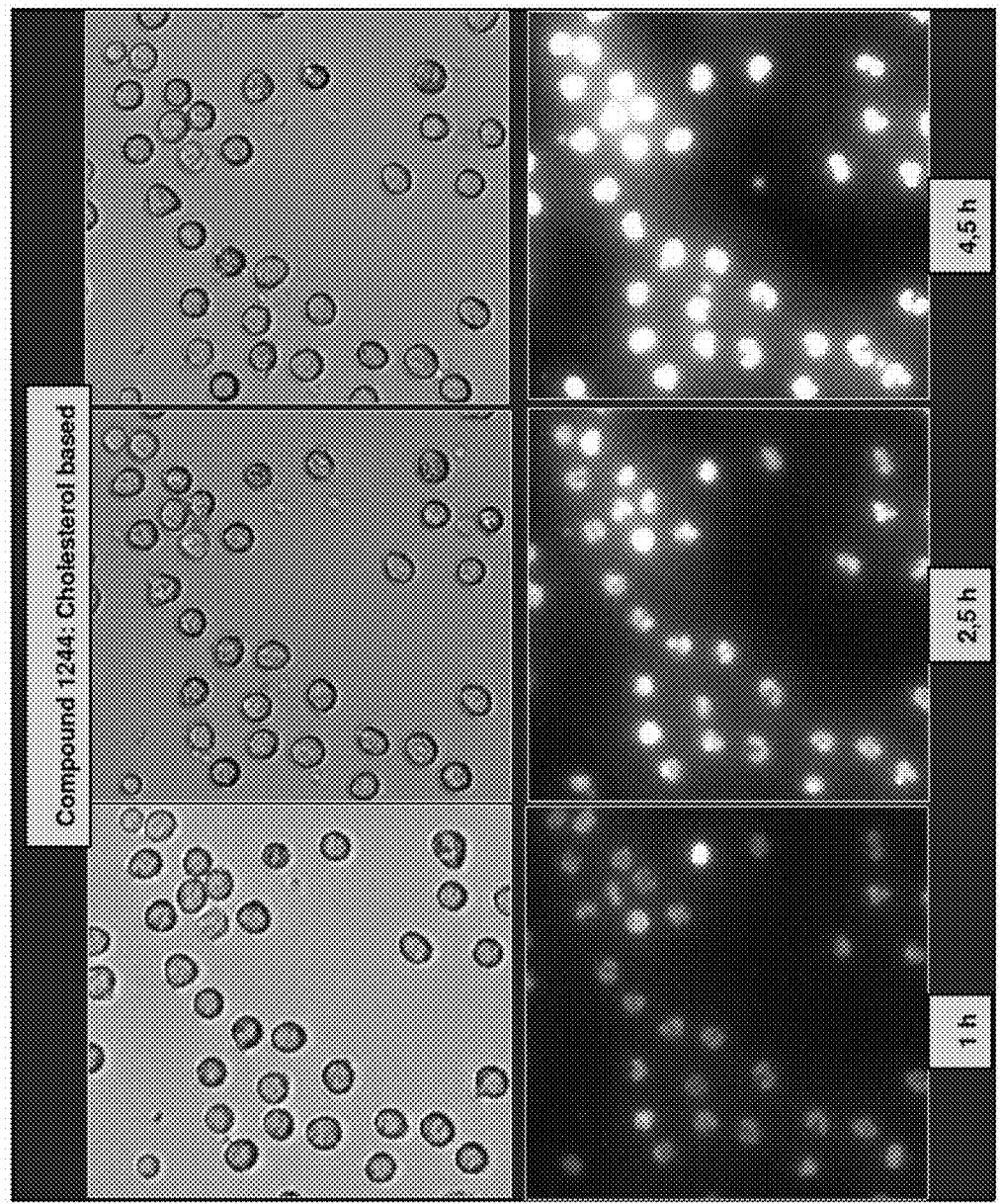
FIG. 22A: shows that tri-functional linker moieties do not influence cell viability. It was found that the tested compounds for use according to the invention, namely No. 1244 as compound with cholesterol-moiety do not influence cell morphology during linker incubation time of 4.5 hours. Left pictures: 1 h incubation. Middle pictures: 2.5 h incubation. Right pictures: 4.5 h incubation. Upper pictures: Brightfield. Lower pictures: DAPI.
Figure 22B:
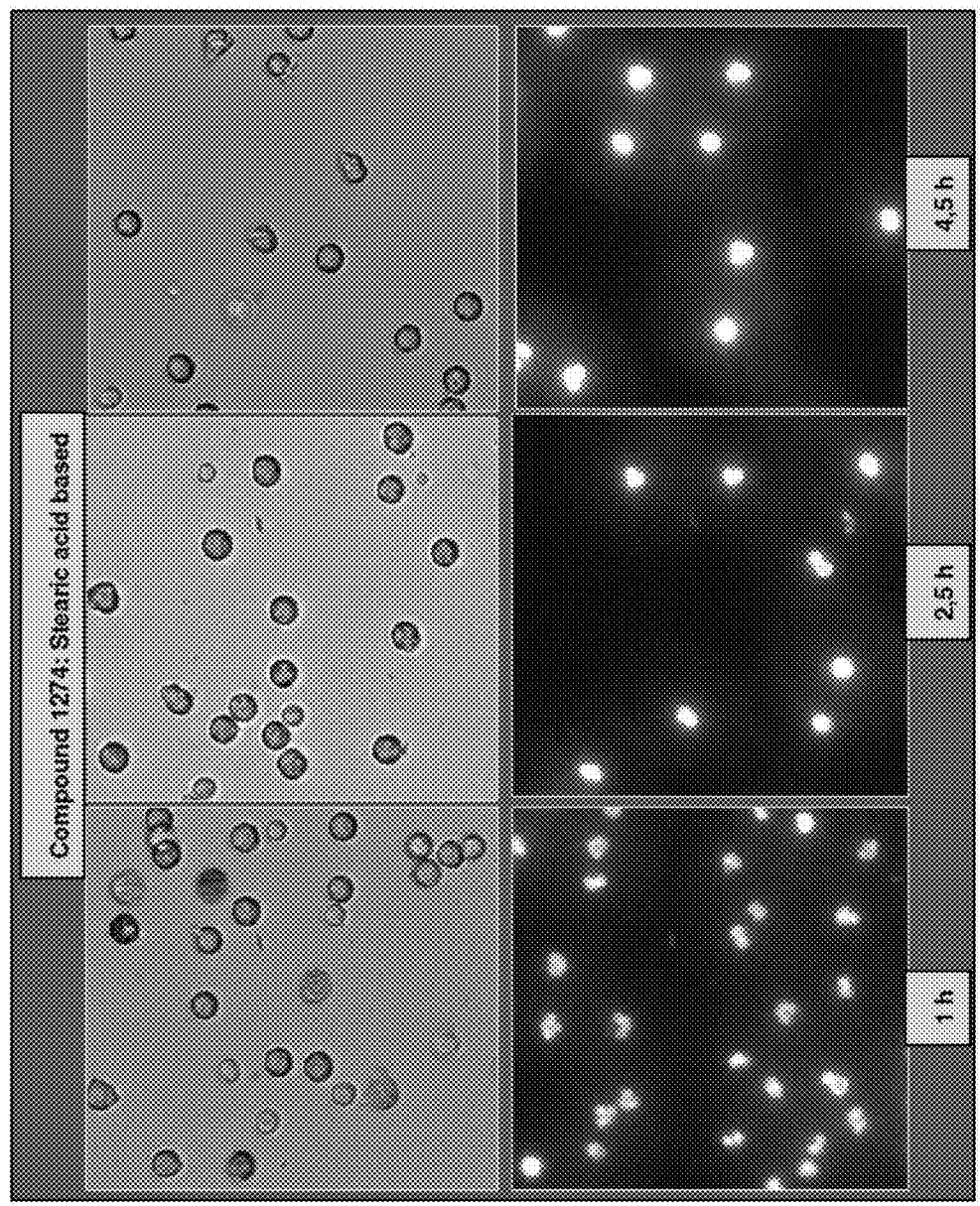
FIG. 22B: shows that tri-functional linker moieties do not influence cell viability. It was found that the tested compounds for use according to the invention, namely No. 1274 as compound with stearic acid-moiety, do not influence cell morphology during linker incubation time of 4.5 hours. Left pictures: 1 h incubation. Middle pictures: 2.5 h incubation. Right pictures: 4.5 h incubation. Upper pictures: Brightfield. Lower pictures: DAPI.

The results of a first experiment in this context are shown in FIGS. 22 A and B.

Cell viability test using WST-1 proliferation kit (RAS) was performed, employing different molecules of the invention differing in the trifunctional linker moieties.

The different linkers do not influence the cell viability during linker incubation time of 4 hours, as can be seen from FIG. 22.

Figure 23:
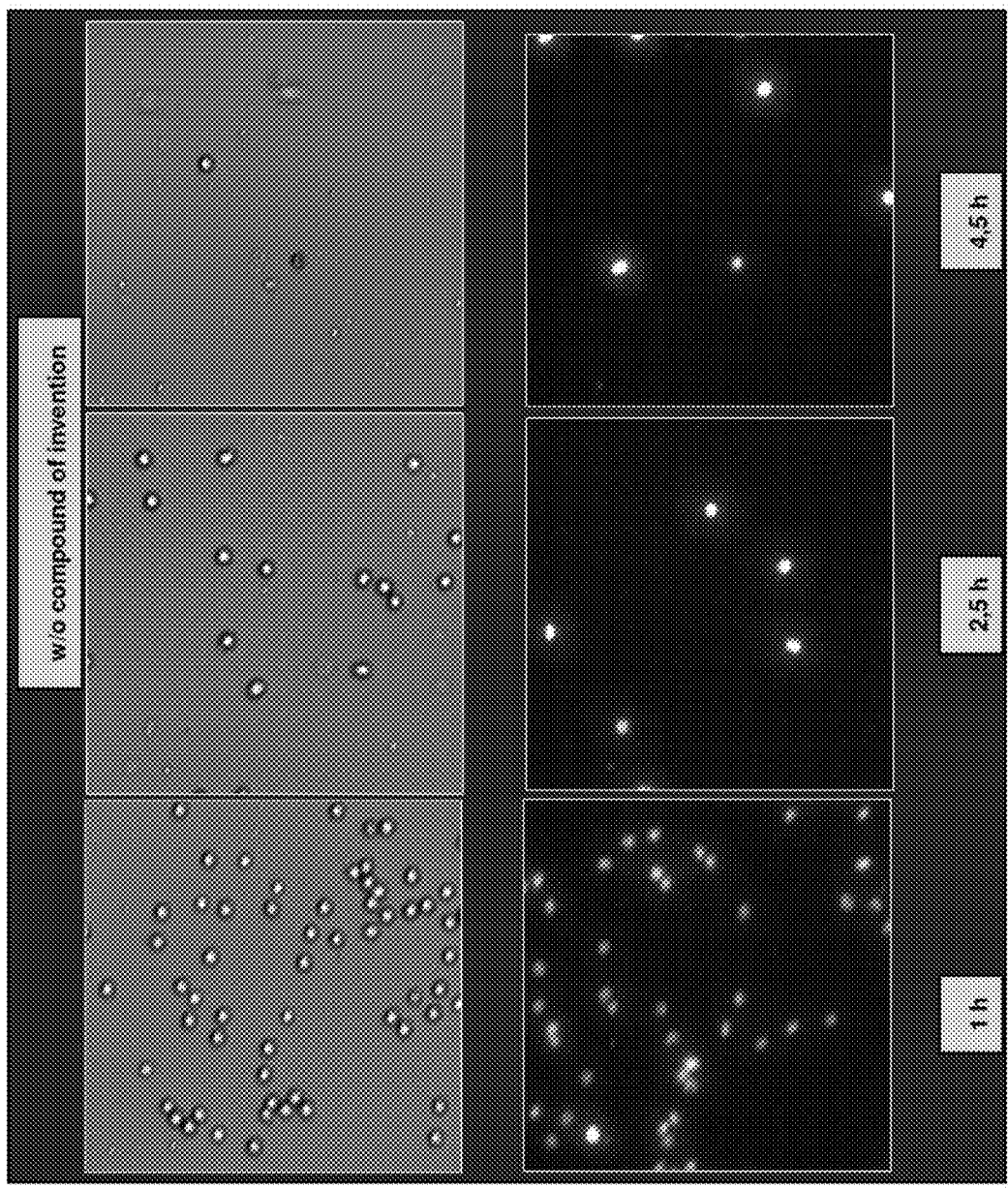
FIG. 23: shows cell morphology without linker incubation at different points of time. Without compound for use according to the invention addition, cells diffuse away during an incubation time of 4.5 hours. Cell morphology is not influenced in left cells during the incubation time. Left pictures: 1 h incubation. Middle pictures: 2.5 h incubation. Right pictures: 4.5 h incubation. Upper pictures: Brightfield. Lower pictures: DAPI.

The results of a second experiment in this context are shown in FIGS. 23A and B. It was found that the tested molecules of the invention (No. 1244 and 1274) do not influence cell morphology during linker incubation time of 4.5 hours.

Figure 24:
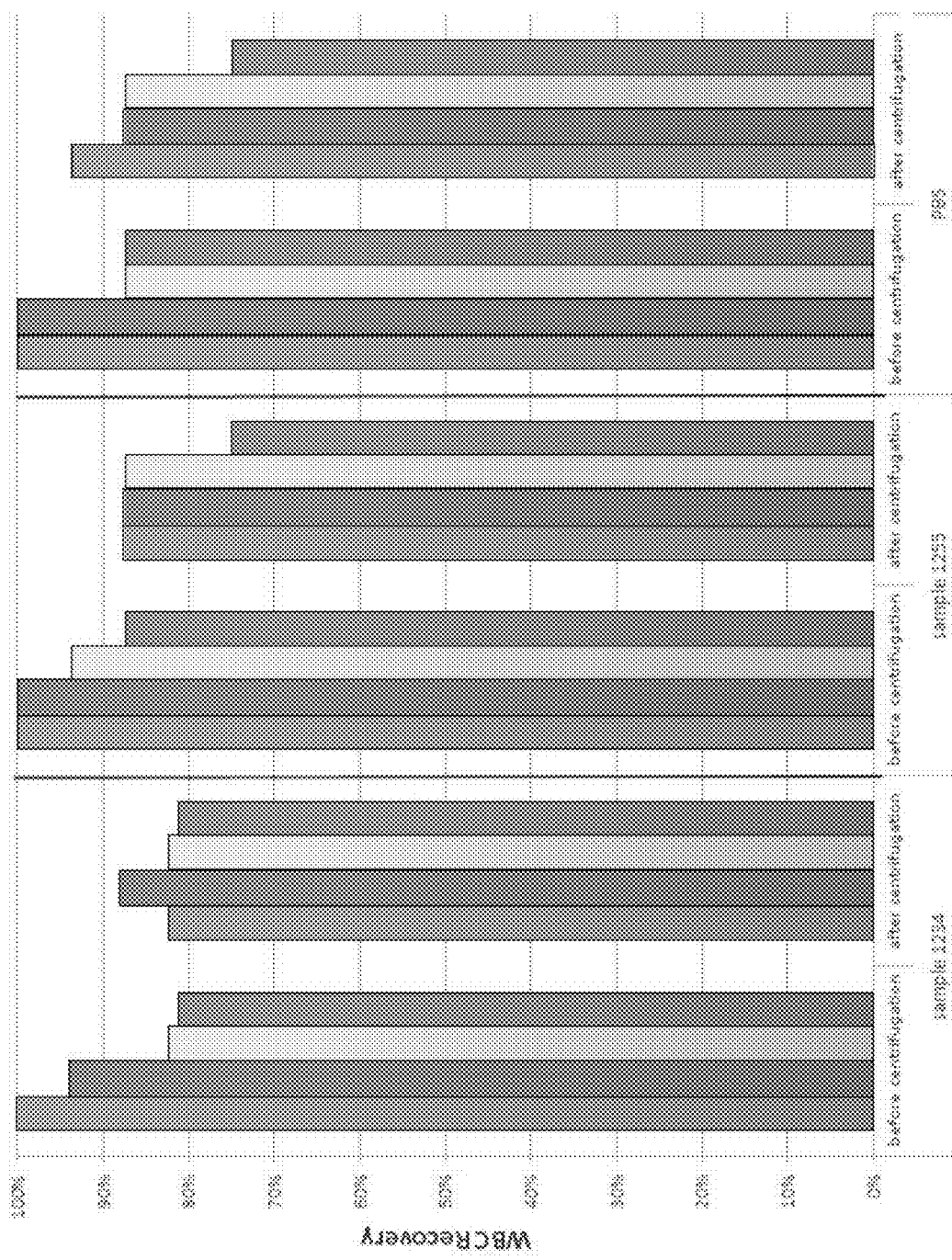
FIG. 24: shows MDA-MB468 cell recovery rate after centrifugation at different points of time. Respective columns from left: 1: 10 min incubation with molecule. 2: 1 h incubation with molecule. 3: 3 h incubation with molecule. 4: 5 h min incubation with molecule. Following compounds for use according to the invention were tested: 1234: 5'-(Cholesteryl-TEG)2-Spacer C18-dT-Biotin-TEG-3'; 1255: 3'-(Myristic acid)2-PEG2000-dT-Biotin-TEG-5' INVERS. MDA-MB468 culture cells are stable during centrifugation processes in PBS as well as using different compounds for use according to the invention within 5 h. Centrifugation characteristics: 20 min, 500×g.

G) Cell Morphology Without Incubation with Molecule of Invention—Different Points of Time The result of this experiment is shown in FIG. 24. Following was found:

Without molecule of the invention addition, cells diffuse away during an incubation time of 4.5 hours Cell morphology is not influenced in left cells during the incubation time.

H) MDA-MB468 Recovery Rate After Centrifugation—Different Points of Time

The result of this experiment is shown in FIG. 25. Following compounds of the invention were tested:

1234: 5'-(Cholesteryl-TEG)2-Spacer C18-dT-Biotin-TEG-3'

1255: 3'-(Myristic acid)2-PEG2000-dT-Biotin-TEG-5' INVERS

Following was found:

MDA-MB468 culture cells are stable during centrifugation processes in PBS as well as using different molecules of the invention within 5 h.

Centrifugation characteristics: 20 min, 500×g.

Example 6: Comparison of SA-Plate (Streptavidin-Plate) Incubated with Compound of the Invention vs WBC (White Blood Cells) Incubated with Compound of the Invention As starting material 5'-(Cholesteryl-TEG)2-PEG2000-Fluos-Biotin_TEG-3' INVERS (14530 pmol/µl) (Internal Reference No.: 29.891250), and a streptavidin treated MTP (Microcoat), 12 Well plate were used.

Erythrocyte lysis was performed as follows:

EDTA-whole blood 59.423 6.400 WBC/µl (Ambulanz Roche)

lysis buffer: 100 mM NH4Cl+5 mM Hepes+0.5 mM KHCO3+0.1 mM EDTA-K

Figure 2:
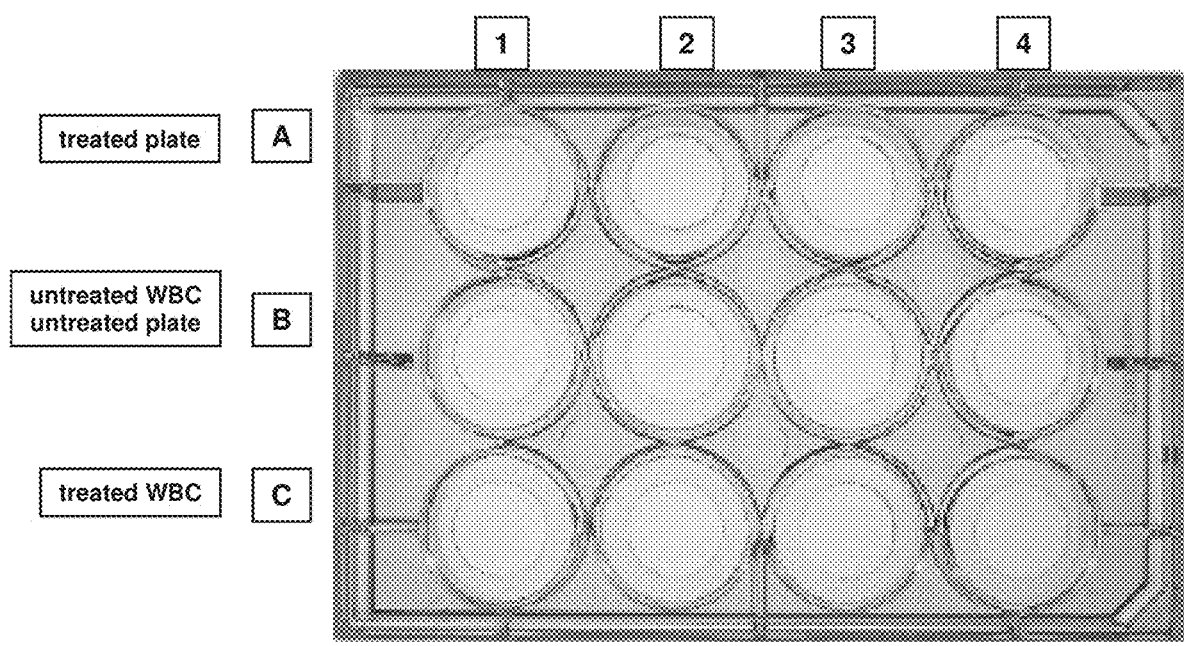
FIG. 2: shows the design of the Experiment of Example 6. 4× determination. Row A: 200 µl PBS introduced, 1 nmol of compound added thereto respectively, mixed, incubated about 30 min, washed 2×PBS, 800 µl PBS introduced, 300.000 WBC (untreated) added. Row B: 800 µl PBS introduced, 300.000 WBC (untreated) added. Row C: 10×10^6 WBC in 1 ml with 10 nmol compound of invention 10 min incubated, 800 µl PBS/Well introduced, 300.000 treated WBC respectively. The first MTP plate washed after 30 min 2× with PBS, overlayed with Höchst and incubated for 15 min.>Cellavista (Operator s9s5) measured. The second plate was measured after 90 min. The third plate was measured after 150 min.

Ca 1×8 ml whole blood filled in 50 ml Falcon tube with lysis buffer, incubate at room temperature for 10 min 15 min at 250 g centrifugated, pellet resuspended by pipetting in and out in lysis buffer; filled to 50 ml with lysis buffer 15 min 250 g centrifugated, pellet resuspended with PBS, filled to 50 ml with PBS, 15 min 250 g centrifugated, filled to 50 ml with PBS WBC measured at Sysmex 1: 37.100 WBC/µl The design of the experiment on the plate is explained below (see FIG. 2):

3×12 Well MTP: Treatment of the WBC with compounds of the invention:

4× determination:

Row A: 200 µl PBS introduced, 1 nmol of compound added thereto respectively, mixed, incubated about 30 min, washed 2×PBS, 800 µl PBS introduced, 300.000 WBC (untreated) added.

Row B: 800 µl PBS introduced, 300.000 WBC (untreated) added.

Row C: 10×10^6 WBC in 1 ml with 10 nmol compound of invention 10 min incubated, 800 µl PBS/Well introduced, 300.000 treated WBC respectively.

The first MTP plate washed after 30 min 2× with PBS, overlaid with Höchst and incubated for 15 min.>Cellavista (Operator s9s5) measured.

The second plate was measured after 90 min.

The third plate was measured after 150 min.

Figure 4:
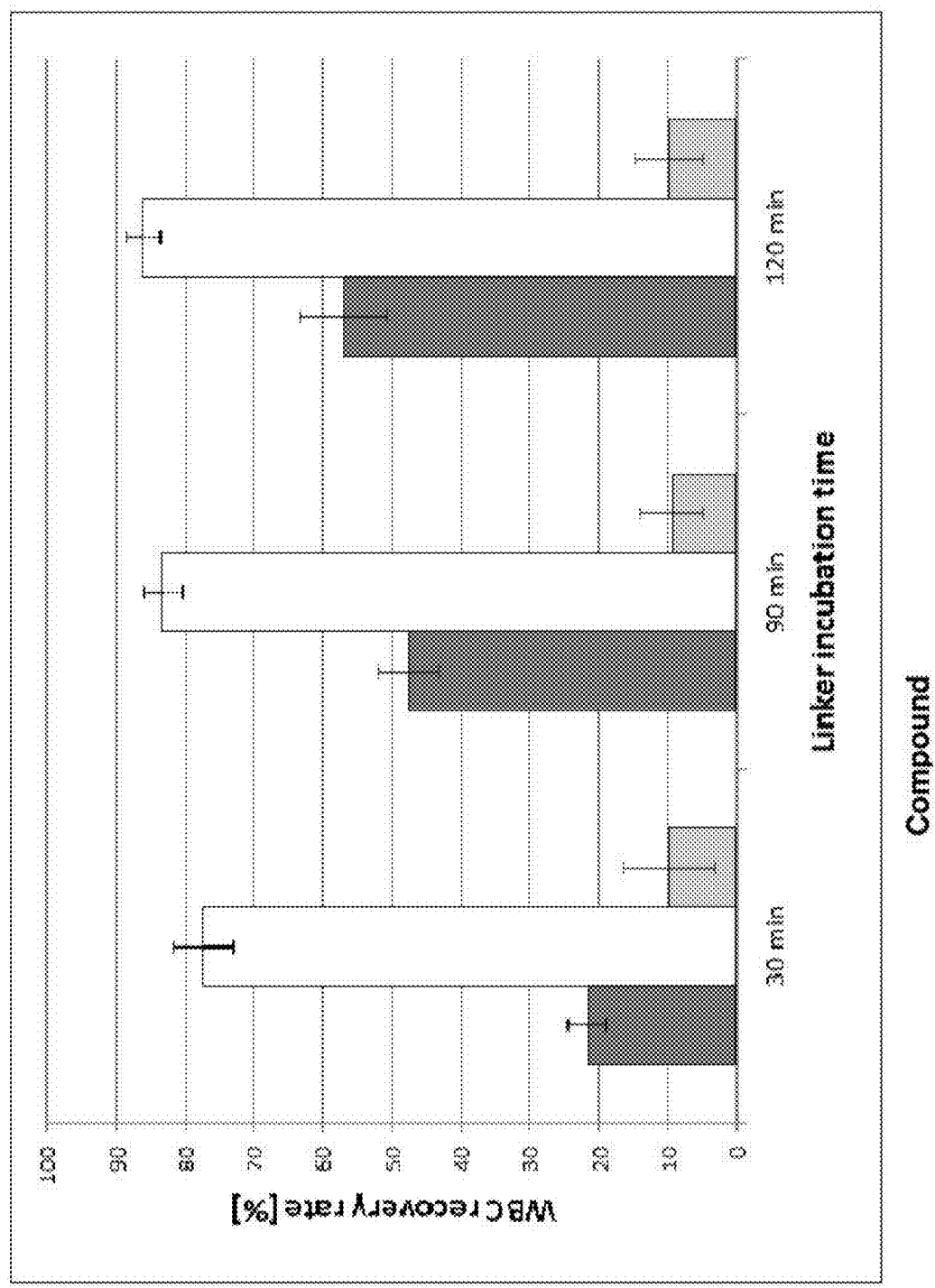
FIG. 4: shows the results of Example 6 after 30, 90 or 120 minutes incubation as a graph.
Figure 5:
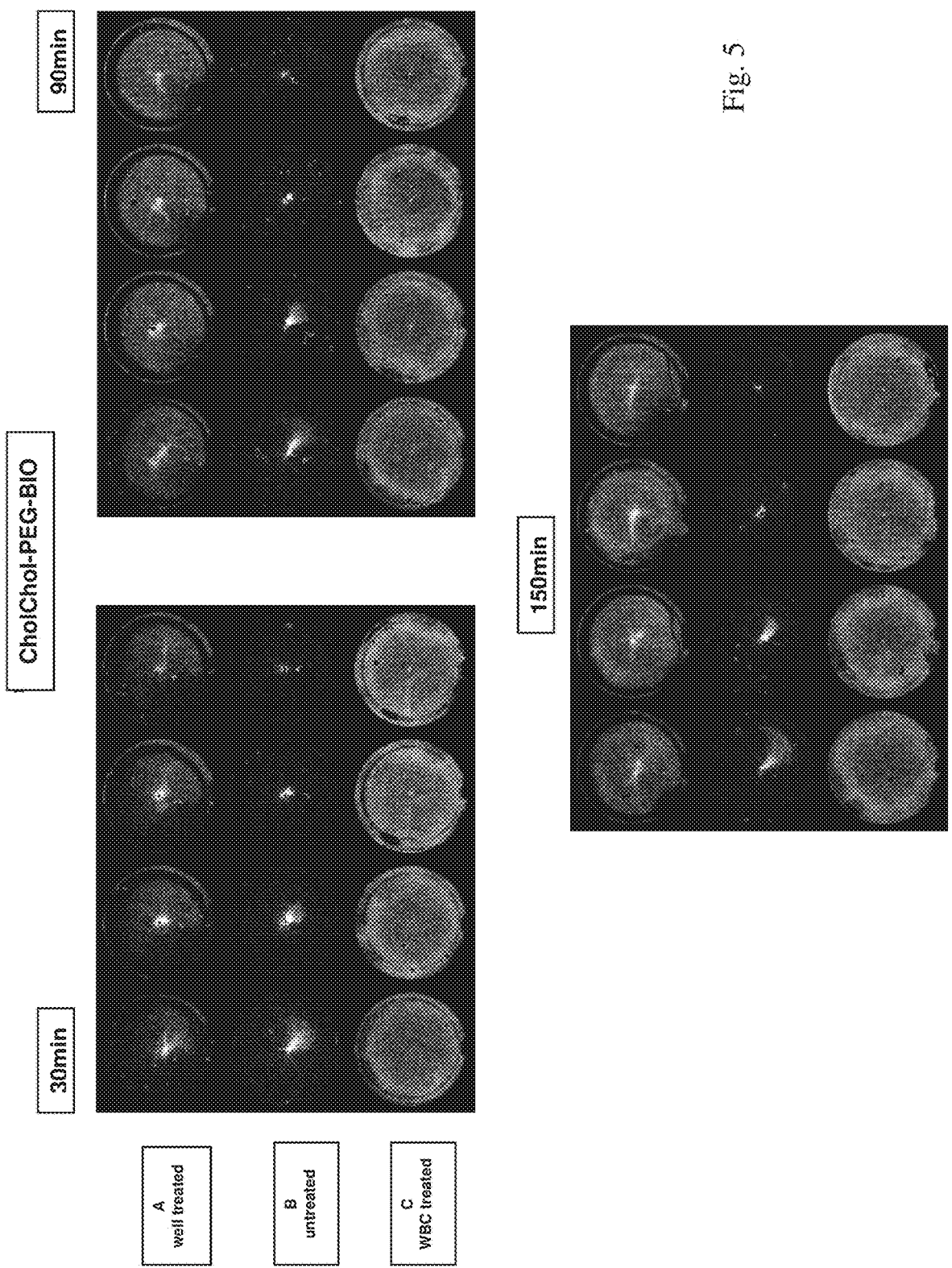
FIG. 5: shows the plates of Example 6 after 30, 90 or 150 minutes incubation.

The calculated results are shown in FIG. 3. A graph representing these results is depicted in FIG. 4. The plates of the experiments are shown in FIG. 5.

The invention claimed is:

1. A compound comprising two, three or four hydrophobic domains and a hydrophilic domain, wherein the two, three or four hydrophobic domains are covalently bound to said hydrophilic domain, and wherein the two, three or four hydrophobic domains each comprise a linear lipid, a steroid or a hydrophobic vitamin, and wherein the hydrophilic domain comprises a compound of Formula (I):

X1-[A1-L1]$_{k1}$-Z-[A2-L1]$_{k2}$-X2        (I), wherein

Z is linear polyethylene glycol (PEG) moiety containing 1 to 100 —O—CH$_2$—CH$_2$— moieties, wherein the polyethylene glycol moiety optionally comprises 1 or more spacer moieties SP connecting two —O—CH$_2$—CH$_2$— moieties, and wherein the linear PEG moiety optionally comprises a linker moiety L3 at one or both ends, each L1 is a phosphate linker moiety, A1 is a trifunctional moiety selected from lysine, serine, serinol, —O—CH$_2$—CH((CH$_2$)$_4$—NH—)—CH$_2$—, glycerol, and a 1,3 diaminoglycerol moiety, wherein each of the two, three or four hydrophobic domains is covalently bound to said hydrophilic domain separately via the two, three or four trifunctional moieties A1 provided by the integer value of the k1, wherein k1 is 2 for 2 hydrophobic domains, k1 is 3 for 3 hydrophobic domains and k1 is 4 for 4 hydrophobic domains, Z is covalently bound to one of the [A1-L1] moieties and to one or the [A2-L1] moieties, A2 is a trifunctional moiety independently selected from lysine, serine, serinol, —O—CH$_2$—CH((CH$_2$)$_4$—NH—)—CH$_2$—, glycerol, and a 1,3 diaminoglycerol moiety, K1 is 2, 3, or 4 and k2 is 1 or 2, X1 and X2 are independently selected from hydrogen or a protecting group, L3 is independently selected from a linear alkyl or alkenyl chain with 1 to 10 C atoms, which is optionally (i) interrupted by 1 to 3 N, O or S atoms, and/or (ii) substituted by 1 to 4 hydroxyl, carbonyl, amino or thiol groups, and wherein the compound further comprises a label moiety and/or a linking group biotin which is suitable for immobilizing the compound to a support, or a salt thereof and wherein Z has the following structure:

-(L3)$_{n2}$[[O—CH$_2$—CH$_2$]$_y$—(SP)$_{n1}$]$_m$—[O—CH$_2$—CH$_2$]$_{y1}$-(L3)$_{n2}$, wherein SP is a spacer moiety which is a phosphate moiety, each n1 is either 0 or 1, selected independently for each m moieties, each n2 is either 0 or 1, selected independently of each other, m is an integer from 1 to 100, y is an integer from 1 to 100, y1 is an integer from 0 to 30, and with the proviso that y*m+y1≤100.

2. The compound according to claim 1, wherein
(a) n1 is identical for the m moieties —[O—CH$_2$—CH$_2$]$_y$—(SP)$_{n1}$]—, and/or
(b) y1 is 0, and/or
(c) y is 4, 5, or 6, and n1 is 1, or
(d) n2 is both 0, or
(e) one or both n2=1, and L3 is an alkyl group with 1 to 10 C atoms which optionally contains an amide group, carbonyl group, carbamate, and/or NH group.

3. The compound of claim 1, wherein X1 or X2 is replaced by a hydrophobic domain.

4. The compound of claim 1, wherein the linear lipid is
(a) a saturated or unsaturated fatty acid, and/or
(b) a fatty acid having from 8 to 26 C atoms, or
the linear lipid is selected from the group consisting of oleic acid, myristic acid, stearic acid and behenic acid.

5. The compound of claim 1, wherein
(a) the steroid is a sterol, or
(b) wherein the steroid is selected from the group consisting of: cholesterol; a steroid hormone; an estrogen; a progestogen; a progestine; a corticosteroid; an ecdysteroid; a brassinosteroid; a hopanoid; and an ergosterol, or
(c) wherein the hydrophobic vitamin is α-tocopherol.

6. The compound of claim 1, wherein the hybrophobic domains
(a) each consist of a linear lipid, a steroid or a hydrophobic vitamin, or
(b) comprise a linear lipid, a steroid or a hydrophobic vitamin each covalently and separately bound to the two, three or four trifunctional moiety A1 via a linker moiety L2, wherein L2 comprises a phosphate group, a moiety —[[O—CH$_2$—CH$_2$]$_{y2}$—(SP)$_n$]m1,
wherein SP and n are as defined in claim 1, y2 is an integer from 1 to 30 and m1 is an integer from 1 to 10, a glycerol moiety, a carbamate group, an amide group, a linear alkyl group having 1 to 10 C atoms, and which alkyl chain contains functional groups at the terminal C-atoms.

7. The compound of claim 6, wherein
the linkers L2 are independently selected from the group consisting of a phosphate, amide, carbamate, an ester group and a moiety —[[O—CH$_2$—CH$_2$]$_{y2}$—(SP)$_n$]$_{m1}$—, wherein
SP and n are as defined in claim 1,
y2 is an integer from 1 to 30, and
m1 is an integer from 1 to 10.

8. The compound of claim 6, wherein L2 is selected from the group consisting of a phosphate, amide, carbamate, an ester group and a moiety —[[O—CH$_2$—CH$_2$]$_{y2}$—(SP)$_n$]$_{m1}$—, wherein
SP and n are as defined in claim 1,
y2 is an integer from 1 to 30, and
m1 is an integer from 1 to 10,
wherein each of the linear lipid, steroid or hydrophobic vitamin is bound to a different trifunctional moiety A1 via the linker moiety tetraethyleneglycol (TEG) or phosphate.

* * * * *